(12) United States Patent
Rana

(10) Patent No.: US 9,878,050 B2
(45) Date of Patent: *Jan. 30, 2018

(54) DELIVERY OF AGENTS USING INTERFERING NANOPARTICLES

(71) Applicant: Sanford-Burnham Medical Research Institute, La Jolla, CA (US)

(72) Inventor: Tariq M. Rana, La Jolla, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/374,679

(22) Filed: Dec. 9, 2016

(65) Prior Publication Data

US 2017/0182177 A1 Jun. 29, 2017

Related U.S. Application Data

(63) Continuation of application No. 13/049,825, filed on Mar. 16, 2011, now Pat. No. 9,526,693.

(60) Provisional application No. 61/314,500, filed on Mar. 16, 2010.

(51) Int. Cl.
*A61K 47/48* (2006.01)
*C12N 15/113* (2010.01)

(52) U.S. Cl.
CPC .. *A61K 47/48323* (2013.01); *A61K 47/48046* (2013.01); *C12N 15/113* (2013.01); *C12N 2310/113* (2013.01); *C12N 2310/321* (2013.01); *C12N 2310/3515* (2013.01)

(58) Field of Classification Search
None
See application file for complete search history.

(56) References Cited

U.S. PATENT DOCUMENTS

| 7,514,099 | B2 | 4/2009 | Chen et al. |
| 9,526,693 | B2 * | 12/2016 | Rana .................. A61K 9/0019 |
| 2005/0020521 | A1 | 2/2005 | Rana |
| 2009/0131360 | A1 | 5/2009 | Woolf et al. |

FOREIGN PATENT DOCUMENTS

| KR | 10-0909786 B1 | | 7/2009 |
| WO | WO 2007/089607 | | 8/2007 |
| WO | WO2007089607 | * | 8/2007 |
| WO | WO 2008/151022 A2 | | 12/2008 |

OTHER PUBLICATIONS

Baigude et al.: "*Design and creation of new nanomaterials for therapeutic RNAi*"; ACS Chem Biol. Apr. 24, 2007; 2(4):237-41.
Baiguide et al.: "*Review Delivery of therapeutic RNAi by nanovehicles*"; Chembiochem. Oct. 12, 2009; 10(15):2449-54.
Chiu et al.: "*Visualizing a correlation between siRNA localization, cellular uptake, and RNAi in living cells*"; Chem Biol. Aug. 2004; 11(8):1165-75.
International Search Report from PCT/US2011/028748.
Karnak and Xu, "*Chemosensitization of prostate cancer by modulating Bcl-2 family proteins*"; Curr. Drug Targets., 11(6):699-707 (2010).
Su et al."Silencing microRNA by interfering nanoparticles in mice"; Nucleic Acids Res. Mar. 2011; 39(6): pp. 1-6, e38.
Qi and Gao: *Emerging application of quantum dots for drug delivery and therapy*; Expert Opin. Drug Deliv. 5(3):263-267, 2008.

* cited by examiner

*Primary Examiner* — Maury Audet
(74) *Attorney, Agent, or Firm* — DLA Piper LLP (US)

(57) ABSTRACT

Provided are compositions and methods for delivery of therapeutic agents, such as chemically stabilized antisense oligonucleotides useful in RNA silencing. The compositions include interfering nanoparticles (iNOPs) associated with one or more agents. Several functional iNOP derivatives are provided which allow for targeted delivery of agents to specific cell types as well as exhibiting reduced cellular toxicity.

21 Claims, 8 Drawing Sheets

DELIVERY OF AGENTS USING INTERFERING NANOPARTICLES

CROSS REFERENCES TO RELATED APPLICATIONS

This application is a continuation application of U.S. application Ser. No. 13/049,825 filed Mar. 16, 2011, now issued as U.S. Pat. No. 9,526,693; which claims the benefit under 35 USC § 119(e) to U.S. Application Ser. No. 61/314,500 filed Mar. 16, 2010. The disclosure of each of the prior applications is considered part of and is incorporated by reference in the disclosure of this application.

STATEMENT REGARDING FEDERALLY SPONSORED RESEARCH OR DEVELOPMENT

This invention was made with government support under Grant Nos. NS060856 and AI41404 awarded by the National Institutes of Health. The government has certain rights in this invention.

BACKGROUND OF THE INVENTION

Field of the Invention

The present invention relates generally to delivery of therapeutic agents, such as chemically modified oligonucleotides, and more specifically to agents associated with nanotransporters to form a delivery complex, and methods of making and using such complexes for targeted delivery of agents to cells.

Background Information

RNA interference (RNAi) is the process whereby double-stranded RNA (dsRNA) induces the sequence-specific degradation of homologous mRNA. Although RNAi was first discovered in *Caenorhabditis elegans*, similar phenomena had been reported in plants (post-transcriptional gene silencing [PTGS]) and in *Neurospora crassa* (quelling). It has become clear that dsRNA-induced silencing phenomena are present in evolutionarily diverse organisms, e.g., nematodes, plants, fungi and trypanosomes. Biochemical studies in *Drosophila* embryo lysates and S2 cell extracts have assisted to unravel the mechanisms by which RNAi works.

Although RNAi has proven to have tremendous potential as a new therapeutic strategy, there remains a need for RNAi agents that are optimized for use in vivo as well as in vitro. Another goal is to efficiently deploy therapeutic RNAi agents to specifically targeted sites or tissues. Accordingly, delivery systems that allow for target delivery to specific cell types and which are non-toxic, non-immunogenic and biodegradable are needed.

MicroRNAs (miRNAs) are small, endogenous, non-coding RNAs that post-transcriptionally regulate gene expression by binding with imperfect complementarity in 3' untranslated regions (3'-UTR) of their target messenger RNAs (mRNAs). MiRNAs are 18-25 nucleotide single-stranded small RNAs associated with a complex of proteins, which are called RNA-induced silencing complex (RISC)-like ribonucleoprotein particle (miRNP). This complex inhibits translation or, depending on the degree of Watson-Crick complementarity, induces degradation of target mRNAs. These small RNAs are usually generated from non-coding regions of many gene transcripts and function to suppress gene expression by translational repression. MiRNAs have been shown to play important roles in development, cell growth, and differentiation. Recent studies have highlighted the role of miRNAs in various disease states and in regulating host-pathogen interactions. For example, mRNAs have been implicated in cardiovascular disease, inflammation, viral infections, and cancers. Hence, disease-associated miRNAs could become potential targets for therapeutic intervention.

SUMMARY OF THE INVENTION

The present invention is based, in part, on the discovery that nanotransporters can be used for delivery of therapeutic agents, such as RNA silencing agents to cells. The nanotransporters of the present invention are referred to as interfering nanoparticles (iNOP) and may be functionalized to provide functionalized iNOP derivatives allowing target delivery of agents.

In certain aspects, the nanotransporters of the invention include a central core with at least one functional surface group attached. In certain embodiments, the core of the nanotransporter is a nanoparticle such as a dendrimer and in various aspects the core is a polylysine dendrimer or alternatively the core may be a single- or multi-walled nanotube. The functional surface groups are chosen for their ability to increase the functionality of the nanotransporter, for example, to increase cell targeting specificity, to increase delivery of the nanotransporter the target cell, and/or to impart a precise biological function.

In one embodiment the functional surface group is at least one of a lipid, cell type specific targeting moiety, fluorescent molecule, and charge controlling molecules. RNA silencing agents of the invention i.e., miRNA silencing agents, as well as other nucleic acid molecules, antisense molecules, ribozymes, etc. and/or pharmaceutical agents (e.g., polynucleotides, proteins, polypeptides, peptides, chemotherapeutic agents, and/or antibiotics), can be operably linked (e.g., conjugated or otherwise associated with) to the core for target specific delivery.

In another embodiment, the invention provides methods for delivering a nucleic acid molecule (e.g., an miRNA silencing agent of the invention) and/or a pharmaceutical agent to a cell. The method includes contacting the cell with a nanotransporter including interfering nanoparticle-7 (iNOP-7) that is operably linked to the nucleic acid molecule and/or pharmaceutical agent, thereby delivering the nucleic acid molecule and/or pharmaceutical agent to the cell. In one aspect, the cell that is contacted is a human cell, for example, a liver cell.

In other aspects, the invention provides improved RNA silencing agents for use in the treatment of diseases and disorders including, but not limited to, metabolic diseases or disorders, atherosclerosis, arteriosclerosis, hepatitis C, cancers, and hypercholesterolemia. In other aspects, the invention provides nanotransporters and use of nanotransporters for the targeted delivery of agents, such as nucleic acid agents in vivo and in vitro.

In another embodiment disclosed herein, is provided A composition comprising a nanotransporter interfering nanoparticle-7 (iNOP-7), wherein the iNOP-7 is optionally functionalized with any of groups A-J:

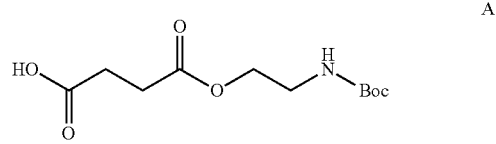

A

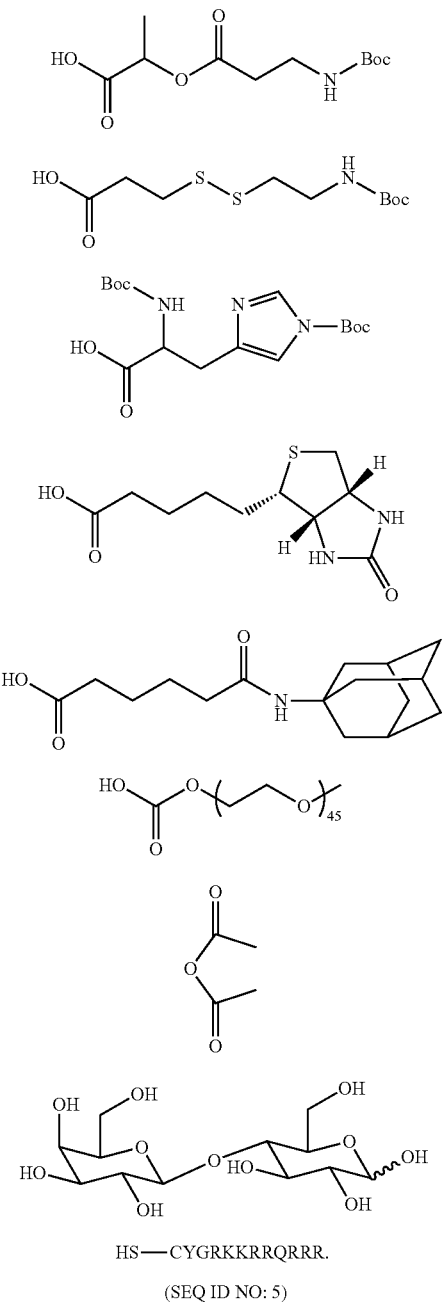

In various embodiments, A forms iNOP-7E; B forms iNOP-7LE; C forms iNOP-7DS; D forms iNOP-7His; E-forms iNOP-7Bio; F forms iNOP-7AD; G forms iNOP-7PEG; H forms iNOP-7A; I forms iNOP-7Lac; and J forms iNOP-7TAT. In some embodiments, the iNOP or derivatized iNOP is associated with a nucleic acid molecule or pharmaceutical agent. In one embodiment, the nucleic acid molecule is an antisense oligonucleotide which may optionally be chemically modified to include, for example, a 2'-O—F, 2'-Ome, 2'MOE, 2'-H, 2'-amino, 4-thioU or 6-thioG modification of one or more nucleotides, introduction of one or more phosphorothioate linkages, introduction of one or more locked nucleotides, or a combination thereof. In various embodiments, the oligonucleotide is RNA and may be microRNA mimic, anti-microRNA, dsRNA, siRNA, stRNA, or shRNA. In some embodiments, the sense strand, anti-sense strand or both may be chemically modified.

In another embodiment disclosed herein, is provided a method of delivering an agent to a cell comprising contacting the cell with a nanotransporter interfering nanoparticle-7 (iNOP-7) associated with an agent, wherein the iNOP-7 is optionally functionalized with any of groups A-J.

In another embodiment disclosed herein, is provided a method of altering gene expression in a cell comprising contacting the cell with a nanotransporter interfering nanoparticle-7 (iNOP-7) associated with an agent that alters gene expression, wherein the iNOP-7 is optionally functionalized with any of groups A-J.

In another embodiment disclosed herein, is provided a composition comprising a nanotransporter interfering nanoparticle-7 (iNOP-7) associated with an antisense oligonucleotide having a sequence modified with more than one chemically modified nucleotide such that in vivo or in vitro stability is enhanced as compared to a corresponding unmodified sequence, wherein the iNOP-7 is optionally functionalized with any of groups A-J.

In another embodiment disclosed herein, is provided a method of treating a disease in a subject comprising administering a nanotransporter interfering nanoparticle-7 (iNOP-7) associated with a therapeutic agent to the subject, wherein the iNOP-7 is optionally functionalized with any of groups A-J.

In another embodiment disclosed herein, is provided a composition including a nanotransporter interfering nanoparticle-7 (iNOP-7) associated or conjugated with an agent that inhibits expression of a microRNA (miRNA), wherein the miRNA is selected from miRNA-122, miRNA-17, miRNA-16, miRNA-130, and miRNA-196.

In another embodiment disclosed herein, an agent that inhibits expression of miRNA-122 is provided. In a yet another embodiment provided herein, the agent that inhibits expression of miRNA-122 is an anti-miRNA oligonucleotide. In a further embodiment, the anti-miRNA oligonucleotide is an antisense oligonucleotide. In a certain embodiment, the anti-miRNA oligonucleotide is chemically modified. In another embodiment, the anti-miRNA oligonucleotide is about 7-25 nucleotides in length.

In other embodiments provided herein, at least three of the nucleotides of the anti-miRNA oligonucleotide are chemically modified. In a further embodiment provided herein, the anti-miRNA oligonucleotide is set forth in SEQ ID NO: 1.

In one embodiment, the invention provides methods for delivering a nucleic acid molecule to a cell in vivo by contacting a cell with iNOP-7 associated or conjugated with an agent that inhibits expression of an miRNA selected from miRNA-122, miRNA-17, miRNA-16, miRNA-130, and miRNA-196, thereby delivering the nucleic acid molecule.

In one embodiment, the invention provides methods for inhibiting expression of an miRNA in a cell in vivo, which includes contacting the cell with iNOP-7 conjugated or associated with an agent that inhibits expression of an miRNA selected from miRNA-122, miRNA-17, miRNA-16, miRNA-130, and miRNA-196.

In other embodiments provided herein, the miRNA inhibitory agent is delivered at a dose of about 0.1 to about 10 mg/kg.

In yet another embodiment provided herein, miRNA inhibitory agent is delivered at a dose of about 2 mg/kg.

In a further embodiment, a nucleic acid molecule is provided wherein the nucleic acid molecule includes a single-stranded 5' antisense sequence. In one embodiment, the nucleic acid molecule has a sequence that is complementary to an miRNA sequence to specifically target and interfere with or inhibit expression of the miRNA. In another embodiment, the nucleic acid molecule has a sequence that has sufficient complementarity to an miRNA sequence to specifically target and interfere with or inhibit expression of the miRNA. In one embodiment, the sequence of the nucleic acid molecule is modified with more than one chemically modified nucleotides such that in vivo stability is enhanced as compared to a corresponding unmodified nucleic acid sequence.

In one embodiment, a nucleic acid is provided that interferes with miRNA expression wherein the nucleic acid molecule comprises at least one mismatch with an miRNA not targeted for inhibition.

In yet another embodiment provided herein, the miRNA that is inhibited is inhibited by a nucleic acid molecule associated with a disease selected from metabolic syndrome, cancer, atherosclerosis, arteriosclerosis, hypercholesterolemia, and hepatitis C. In a further embodiment provided herein, the disease associated with miRNA is hepatocellular carcinoma. In another embodiment provided herein, the disease associated with miRNA is hypercholesterolemia.

In yet another embodiment provided herein, the cholesterol level of the subject decreases by at least 5% as compared to the cholesterol level of the subject prior to administration of the composition.

In certain embodiments provided herein, the cholesterol level of the subject decreases by 10%, 15%, 20%, 25%, or even more, as compared to the cholesterol level of the subject prior to administration of the composition.

In a certain embodiment disclosed herein, a composition including iNOP-7 that is associated or conjugated with a single-stranded 5' antisense sequence is provided. In a certain embodiment, the 5' antisense sequence of the composition is complementary to an miRNA sequence to specifically target and interfere with expression of the miRNA. In another embodiment, the composition has a 5' antisense sequence that has sufficient complementarity to an miRNA sequence to specifically target and interfere with or inhibit expression of the miRNA. In other embodiments, the 5' antisense sequence of the composition is modified with more than one chemically modified nucleotides such that in vivo stability is enhanced as compared to a corresponding unmodified nucleic acid sequence.

In another embodiment disclosed herein, a method of inhibiting miRNA in a cell in vitro including contacting the cell, in an amount sufficient to stimulate miRNA silencing is provided. In one embodiment, the method of miRNA inhibition includes a single-stranded 5' antisense sequence wherein the sequence is complementary to an miRNA sequence to specifically target and interfere with expression of the miRNA. In another embodiment, the method of miRNA inhibition includes a single-stranded 5' antisense sequence that has sufficient complementarity to an miRNA sequence to specifically target and interfere with or inhibit expression of the miRNA. In certain embodiments, the antisense sequence employed in the miRNA inhibition method is modified with more than one chemically modified nucleotides such that in vivo stability is enhanced as compared to a corresponding unmodified nucleic acid sequence.

In another embodiment provided herein, the nanotransporter that is associated or conjugated with the nucleic acid molecule set forth in SEQ ID NO:1 includes either a nanoparticle core or a nanotube core. The nanotube may be a single-walled or multi-walled nanotube. In various embodiments, the nanotransporter is a dendrimer. In other embodiments, the dendrimer is a polylysine dendrimer. In further embodiments, functional surface group conjugated to the nanotransporter core is at least one of a lipid, a cell type specific targeting moiety, a fluorescent molecule, and a charge controlling molecule. In one embodiment, the targeting moiety is a tissue-selective peptide. In another embodiment, the lipid of the functional surface group is an oleoyl lipid, or derivative thereof.

In another embodiment, the invention provides a composition of a nanotransporter interfering nanoparticle-7 (iNOP-7) associated or conjugated with an agent that inhibits expression of a microRNA (miRNA), wherein the miRNA is selected from miRNA-122, miRNA-17, miRNA-16, miRNA-130, and miRNA-196, and wherein the iNOP-7 is functionalized with any of groups A-J.

In another embodiment, the invention provides a composition of a nanotransporter interfering nanoparticle-7 (iNOP-7) associated or conjugated with an agent that inhibits expression of a microRNA (miRNA), wherein the miRNA is selected from miRNA-122, miRNA-17, miRNA-16, miRNA-130, and miRNA-196, and wherein the iNOP-7 is functionalized with group I:

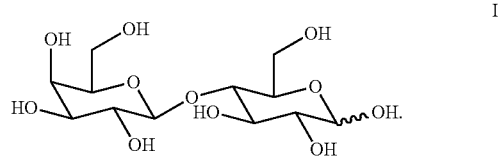 [SMILES: OCC1OC(OC2C(CO)OC(O)C(O)C2O)C(O)C(O)C1O]

In another embodiment, the invention provides methods for tissue specific delivery of RNAi by modified iNOPs by administering a composition of a nanotransporter interfering nanoparticle-7 (iNOP-7) associated with an agent that inhibits gene expression, and wherein the iNOP-7 is functionalized with any of groups A-J. In some embodiments, the modified iNOPs are delivered via targeted delivery to the liver, spleen and/or lung. In one embodiment the iNOP-7 is functionalized with group I:

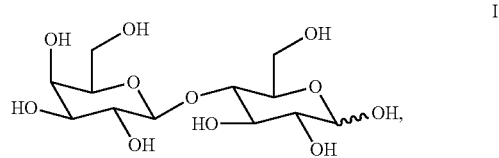 [SMILES: OCC1OC(OC2C(CO)OC(O)C(O)C2O)C(O)C(O)C1O]

wherein the modified iNOP-7Lac is delivered to the liver.

In another embodiment, the invention provides a composition of a nanotransporter interfering nanoparticle-7 (iNOP-7) associated or conjugated with an agent that inhibits expression of a microRNA (miRNA), wherein the iNOP-7 is functionalized with any of groups A-J, wherein A forms iN0P-7E; B forms iN0P-7LE; C forms iN0P-7DS; D forms iNOP-7His; E-forms iN0P-7Bio; F forms iN0P-7AD; G forms iN0P-7PEO; H forms iN0P-7A; I forms iN0P-7Lac; and J forms iN0P-7TAT, and wherein the agent inhibits expression of miR-122.

In another embodiment, the invention provides a composition of a nanotransporter interfering nanoparticle-7 (iNOP-7) associated or conjugated with an agent that inhibits expression of a microRNA (miRNA), wherein the iNOP-7 is functionalized with any of groups A-J, wherein the agent is an anti-miRNA oligonucleotide, and wherein the oligonucleotide is set forth in SEQ ID NO:1.

In another embodiment, the invention provides methods for delivering a nucleic acid molecule to a cell in vivo or in vitro by contacting a cell with iNOP-7 associated or conjugated with an agent that inhibits expression of an miRNA (miRNA), wherein the iNOP-7 is functionalized with any of groups A-J, and wherein A forms iNOP-7E; B forms iNOP-7LE; C forms iNOP-7DS; D forms iNOP-7His; E-forms iNOP-7Bio; F forms iNOP-7AD; G forms iNOP-7PEG; H forms iNOP-7A; I forms iNOP-7Lac; and J forms iNOP-7TAT, thereby delivering the nucleic acid molecule.

In another embodiment, the invention provides a composition of an iNOP-7 that is associated or conjugated with: (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the iNOP-7 is functionalized with any of groups A-J, wherein A forms iNOP-7E; B forms iNOP-7LE; C forms iNOP-7DS; D forms iNOP-7His; E-forms iNOP-7Bio; F forms iNOP-7AD; G forms iNOP-7PEG; H forms iNOP-7A; I forms iNOP-7Lac; and J forms iNOP-7TAT, thereby inhibiting expression of an miRNA.

In another embodiment, the invention provides methods for inhibiting miRNA in a cell in vitro or in vivo by contacting the cell, in an amount sufficient to stimulate miRNA silencing, with: (a) a single-stranded 5' antisense sequence wherein the sequence is complementary to an miRNA sequence to specifically target and interfere with expression of the miRNA; and (b) the sequence is modified with more than one chemically modified nucleotides such that in vivo or in vitro stability is enhanced as compared to a corresponding unmodified nucleic acid sequence, wherein the miRNA inhibition is stimulated in the cell by contacting the cell with a composition of an miRNA inhibitory agent which is associated or conjugated to iNOP-7, wherein the iNOP-7 is functionalized with any of groups A-J, and wherein A forms iNOP-7E; B forms iNOP-7LE; C forms iNOP-7DS; D forms iNOP-7His; E-forms iNOP-7Bio; F forms iNOP-7AD; G forms iNOP-7PEG; H forms iNOP-7A; I forms iNOP-7Lac; and J forms iNOP-7TAT, thereby inhibiting expression of an miRNA.

In another embodiment, the invention provides a nucleic acid molecule, wherein the nucleic acid is set forth in SEQ ID NO:1, wherein the nucleic acid molecule is associated or conjugated with an iNOP-7, wherein the iNOP-7 is functionalized with any of groups A-J, and wherein A forms iNOP-7E; B forms iNOP-7LE; C forms iNOP-7DS; D forms iNOP-7His; E-forms iNOP-7Bio; F forms iNOP-7AD; G forms iNOP-7PEG; H forms iNOP-7A; I forms iNOP-7Lac; and J forms iNOP-7TAT.

DETAILED DESCRIPTION OF THE INVENTION

Figure 1A:
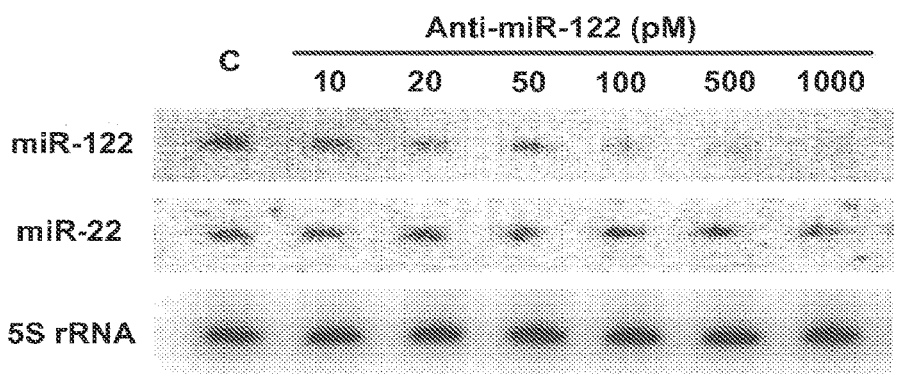
FIGS. 1A and 1B illustrate the specific silencing of miRNA-122 in a dose-dependent manner by iNOP-7 in vitro. Quantification of reduced miR-122 levels in Huh-7 cells after transfected with iNOP-7 containing anti-miR-122 is also depicted. (A) Huh-7 cells were transfected by iNOP-7 containing anti-miR-122 at varying concentrations as indicated for 4 hours. Total RNA was isolated from cells 24 hours after transfection and separated on 14% polyacrylamide gels. Membrane was probed for miR-122 and miR-22, respectively. 5S rRNA is shown as a loading control. (B) Quantification of reduced miR-122 levels in Huh-7 cells after transfected with iNOP-7 containing anti-miR-122. Northern blots of miR-122 and miR-22 (panel a) were analyzed by densitometry and normalized to 5S rRNA.

The present invention is based on the discovery that nanoparticles can be used to deliver agents, such as therapeutic and pharmaceutical agents, including both duplex RNA molecules (e.g., siRNA, microRNA mimics) and single-stranded RNA molecules (shRNA and anti-miRNA) in a target fashion while exhibiting reduced cellular toxicity. In certain aspects agents may be delivered to silence disease-related endogenous genes or miRNA. Novel oligonucleotides associated or conjugated to iNOP-7 or functionalized derivatives thereof, have been discovered, together with methods of synthesizing and using the compositions to target specific cells and provide methods for the treatment of diseases in a subject by administering the composition.

In one aspect, upon administration of iNOP-7 containing chemically modified anti-miRNA into animals, miRNA was specifically silenced and the expression of target genes were subsequently altered in liver, total plasma cholesterol was lowered. In addition, iNOP-7 treatment was nontoxic and did not induce an immune response. Moreover, iNOP-7 can be modified to target specific tissues and to modulate pharmacological properties to develop tissue-specific RNAi-based therapies. A key aspect of the discovery is the utility of nanoparticles to deliver chemically modified anti-miR to liver tissues to silence endogenous miRNA in mice at clinical feasible doses.

In another aspect, functionalized derivatives of iNOP-7 were discovered that provide for targeted delivery of agents to specific cell or tissue types, such as liver, spleen and lung. The functionalized iNOPs may be associated with a variety of agents, such as oligonucleotides optionally containing chemically modified sequences. The delivery vehicles were determined to be both non-toxic and cell specific.

In other aspects, the present invention features nanotransporters which include at least one chemically modified RNA silencing agents (e.g., antisense miRNA silencing agents, RNAi agents such small interfering RNA molecules (siRNA)) and methods (e.g., research and/or therapeutic methods) for using the RNA silencing agents. The present invention includes RNA silencing agents (e.g., RNAi agents) which have been chemically modified at both the 3' end and the 5' end of the sense strand, the antisense strand or both. In other aspects, the present invention includes an RNA silencing agent such as an miRNA silencing agent or an RNA-induced silencing complex (RISC)-like ribonucleoprotein particle (miRNP). The miRNA silencing agents have been chemically modified, anywhere along the antisense strand. Such RNA silencing agents, and nanotransporters which incorporate them, are useful, for example, in the treatment of cancers, hypercholesterolemia, atherosclerosis, arteriosclerosis, and metabolic disorders e.g., high cholesterol, diabetes and obesity.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

Thus, in one embodiment, is provided A composition comprising a nanotransporter interfering nanoparticle-7 (iNOP-7), wherein the iNOP-7 is optionally functionalized with any of groups A-J:

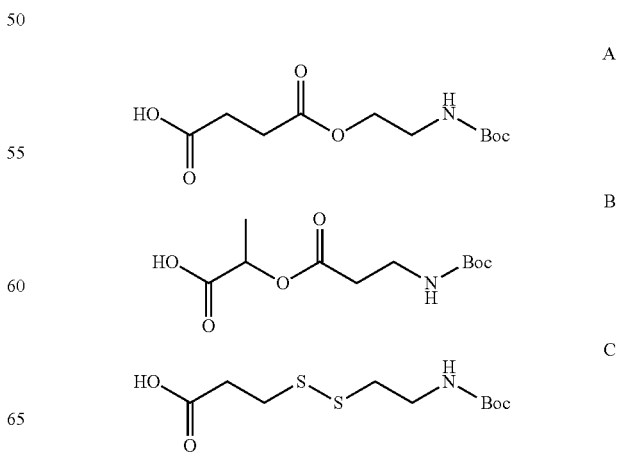

-continued

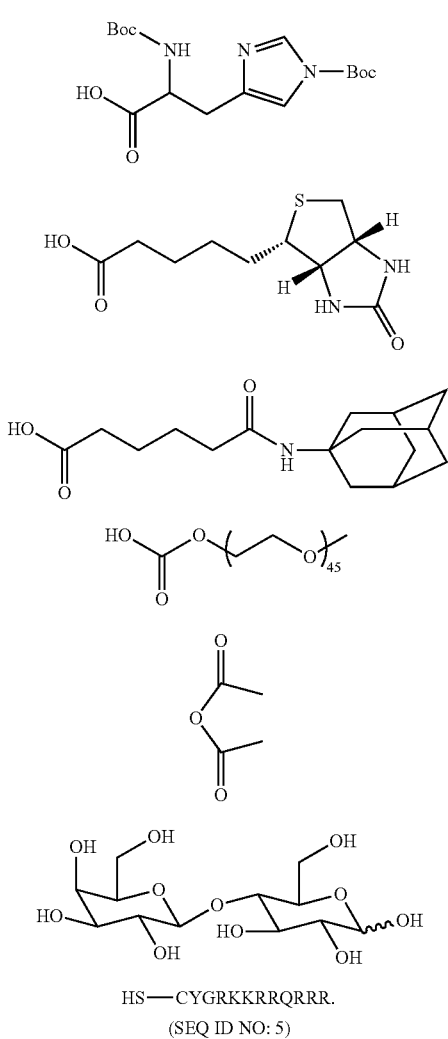

HS—CYGRKKRRQRRR.
(SEQ ID NO: 5)

In various embodiments, A forms iNOP-7E; B forms iNOP-7LE; C forms iNOP-7DS; D forms iNOP-7His; E-forms iNOP-7Bio; F forms iNOP-7AD; G forms iNOP-7PEG; H forms iNOP-7A; I forms iNOP-7Lac; and J forms iNOP-7TAT. In some embodiments, the iNOP or derivatized iNOP is associated with a nucleic acid molecule or pharmaceutical agent. In one embodiment, the nucleic acid molecule is an antisense oligonucleotide which may optionally be chemically modified to include, for example, a 2'-O-F, 2'-Ome, 2'MOE, 2'-H, 2'-amino, 4-thioU or 6-thioG modification of one or more nucleotides, introduction of one or more phosphorothioate linkages, introduction of one or more locked nucleotides, or a combination thereof. In various embodiments, the oligonucleotide is RNA and may be microRNA mimic, anti-microRNA, dsRNA, siRNA, stRNA, or shRNA. In some embodiments, the sense strand, anti-sense strand or both may be chemically modified.

In another embodiment disclosed herein, is provided a method of delivering an agent to a cell comprising contacting the cell with a nanotransporter interfering nanoparticle-7 (iNOP-7) associated with an agent, wherein the iNOP-7 is optionally functionalized with any of groups A-J.

In another embodiment disclosed herein, is provided a method of altering gene expression in a cell comprising contacting the cell with a nanotransporter interfering nanoparticle-7 (iNOP-7) associated with an agent that alters gene expression, wherein the iNOP-7 is optionally functionalized with any of groups A-J.

In another embodiment disclosed herein, is provided a composition comprising a nanotransporter interfering nanoparticle-7 (iNOP-7) associated with an antisense oligonucleotide having a sequence modified with more than one chemically modified nucleotide such that in vive or in vitro stability is enhanced as compared to a corresponding unmodified sequence, wherein the iNOP-7 is optionally functionalized with any of groups A-J.

In another embodiment disclosed herein, is provided a method of treating a disease in a subject comprising administering a nanotransporter interfering nanoparticle-7 (iNOP-7) associated with a therapeutic agent to the subject, wherein the iNOP-7 is optionally functionalized with any of groups A-J.

In another embodiment, the invention provides a composition of a nanotransporter interfering nanoparticle-7 (iNOP-7) associated or conjugated with an agent that inhibits expression of a microRNA (miRNA), wherein the miRNA is selected from miRNA-122, miRNA-17, miRNA-16, miRNA-130, and miRNA-196.

In another embodiment, the invention provides a composition of a nanotransporter interfering nanoparticle-7 (iNOP-7) associated or conjugated with an agent that inhibits expression of a microRNA (miRNA), wherein the miRNA is selected from miRNA-122, miRNA-17, miRNA-16, miRNA-130, and miRNA-196, and wherein the agent inhibits expression of miR-122.

In another embodiment, the invention provides a composition of a nanotransporter interfering nanoparticle-7 (iNOP-7) associated or conjugated with an agent that inhibits expression of a microRNA (miRNA), wherein the miRNA is selected from miRNA-122, miRNA-17, miRNA-16, miRNA-130, and miRNA-196, and wherein the agent is an anti-miRNA oligonucleotide.

In another embodiment, the invention provides a composition of a nanotransporter interfering nanoparticle-7 (iNOP-7) associated or conjugated with an agent that inhibits expression of a microRNA (miRNA), wherein the miRNA is selected from miRNA-122, miRNA-17, miRNA-16, miRNA-130, and miRNA-196, and wherein the agent is an anti-miRNA oligonucleotide, and wherein the anti-miRNA oligonucleotide is an antisense oligonucleotide.

In another embodiment, the invention provides a composition of a nanotransporter interfering nanoparticle-7 (iNOP-7) associated or conjugated with an agent that inhibits expression of a microRNA (miRNA), wherein the miRNA is selected from miRNA-122, miRNA-17, miRNA-16, miRNA-130, miRNA-196, and wherein the agent is an anti-miRNA oligonucleotide, wherein the anti-miRNA oligonucleotide is an antisense oligonucleotides, and wherein the anti-miRNA oligonucleotide is chemically modified.

In another embodiment, the invention provides a composition of a nanotransporter interfering nanoparticle-7 (iNOP-7) associated or conjugated with an agent that inhibits expression of a microRNA (miRNA), wherein the miRNA is selected from miRNA-122, miRNA-17, miRNA-16, miRNA-130, miRNA-196, and wherein the agent is an anti-miRNA oligonucleotide, wherein the anti-miRNA oligonucleotide is an antisense oligonucleotides, wherein the anti-miRNA oligonucleotide is chemically modified, and wherein the anti-miRNA oligonucleotide is about 7-25 nucleotides in length.

In another embodiment, the invention provides a composition of a nanotransporter interfering nanoparticle-7 (iNOP- 7) associated or conjugated with an agent that inhibits expression of a microRNA (miRNA), wherein the miRNA is selected from miRNA-122, miRNA-17, miRNA-16, miRNA-130, miRNA-196, and wherein the agent is an anti-miRNA oligonucleotide, wherein the anti-miRNA oligonucleotide is an antisense oligonucleotides, wherein the anti-miRNA oligonucleotide is chemically modified, and wherein at least three of the nucleotides of the anti-miRNA oligonucleotide are chemically modified.

In another embodiment, the invention provides a composition of a nanotransporter interfering nanoparticle-7 (iNOP-7) associated or conjugated with an agent that inhibits expression of a microRNA (miRNA), wherein the miRNA is selected from miRNA-122, miRNA-17, miRNA-16, miRNA-130, and miRNA-196, and wherein the agent is an anti-miRNA oligonucleotide, and wherein the oligonucleotide is set forth in SEQ ID NO:1.

In another embodiment, the invention provides methods for delivering a nucleic acid molecule to a cell in vivo by contacting a cell with iNOP-7 associated or conjugated with an agent that inhibits expression of an miRNA selected from miRNA-122, miRNA-17, miRNA-16, miRNA-130, and miRNA-196, thereby delivering the nucleic acid molecule.

In another embodiment, the invention provides methods for inhibiting expression of an miRNA in a cell in vivo by contacting the cell with iNOP-7 conjugated or associated with an agent that inhibits expression of an miRNA selected from miRNA-122, miRNA-17, miRNA-16, miRNA-130, and miRNA-196.

In another embodiment, the invention provides methods for inhibiting expression of an miRNA in a cell in vivo by contacting the cell with iNOP-7 conjugated or associated with an agent that inhibits expression of an miRNA selected from miRNA-122, miRNA-17, miRNA-16, miRNA-130, and miRNA-196, wherein the cell is a human cell.

In another embodiment, the invention provides methods for inhibiting expression of an miRNA in a cell in vivo by contacting the cell with iNOP-7 conjugated or associated with an agent that inhibits expression of an miRNA selected from miRNA-122, miRNA-17, miRNA-16, miRNA-130, and miRNA-196, wherein the cell is a human cell, and wherein the cell is a liver cell.

In another embodiment, the invention provides methods for inhibiting expression of an miRNA in a cell in vivo by contacting the cell with iNOP-7 conjugated or associated with an agent that inhibits expression of an miRNA selected from miRNA-122, miRNA-17, miRNA-16, miRNA-130, and miRNA-196, wherein the cell is a human cell, wherein the cell is a liver cell, and wherein the miRNA inhibitory agent is delivered at a dose of about 0.1 to about 10 mg/kg.

In another embodiment, the invention provides a nucleic acid molecule of (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence.

In another embodiment, the invention provides a nucleic acid molecule of (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the miRNA is associated with a disease selected from metabolic syndrome, cancer, atherosclerosis, arteriosclerosis, hypercholesterolemia, and hepatitis C.

In another embodiment, the invention provides a nucleic acid molecule of (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein at least 3 of the nucleotides of the molecule are chemically modified.

In another embodiment, the invention provides a nucleic acid molecule of (a) a single-stranded 5' antisense sequence wherein the sequence is complementary to an miRNA sequence to specifically target and interfere with expression of the miRNA; and (b) the sequence is modified with more than one chemically modified nucleotides such that in vive stability is enhanced as compared to a corresponding unmodified nucleic acid sequence, wherein the chemically modified nucleotides are 2'-fluoro modified nucleotides.

In another embodiment, the invention provides a nucleic acid molecule of (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the nucleic acid is about 7-25 nucleotides in length.

In another embodiment, the invention provides a nucleic acid molecule of (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the miRNA is associated with a disease selected from metabolic syndrome, cancer, atherosclerosis, arteriosclerosis, hypercholesterolemia, and hepatitis C, and wherein the disease is hepatocellular carcinoma.

In another embodiment, the invention provides a nucleic acid molecule of (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the miRNA is associated with a disease selected from metabolic syndrome, cancer, atherosclerosis, arteriosclerosis, hypercholesterolemia, and hepatitis C, and wherein the disease hypercholesterolemia.

In another embodiment, the invention provides a nucleic acid molecule of (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein at least 3 of the nucleotides of the molecule are chemically modified, and wherein the molecule comprises at least one mismatch with a non-target miRNA.

In another embodiment, the invention provides a nucleic acid molecule of (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the nucleic acid is about 7-25 nucleotides in length, wherein the nucleic acid is set forth in SEQ ID NO: 1.

In another embodiment, the invention provides a nucleic acid molecule of (a) a single-stranded 5' antisense sequence wherein the sequence is complementary to an miRNA sequence to specifically target and interfere with expression of the miRNA; and (b) the sequence is modified with more than one chemically modified nucleotides such that in vive stability is enhanced as compared to a corresponding unmodified nucleic acid sequence, wherein the nucleic acid is about 7-25 nucleotides in length, wherein the nucleic acid is set forth in SEQ ID NO: 1, and wherein the molecule is an anti-miRNA-122.

In another embodiment, the invention provides a composition of iNOP-7 that is associated or conjugated with: (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence.

In another embodiment, the invention provides methods for inhibiting miRNA in a cell in vitro by contacting the cell, in an amount sufficient to stimulate miRNA silencing, with: (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence.

In another embodiment, the invention provides methods for inhibiting miRNA in a cell in vitro by contacting the cell, in an amount sufficient to stimulate miRNA silencing, with: (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the miRNA inhibition is stimulated in the cell by contacting the cell with a composition of an miRNA inhibitory agent which is associated or conjugated to iNOP-7.

In another embodiment, the invention provides methods for inhibiting miRNA in a cell in vitro by contacting the cell, in an amount sufficient to stimulate miRNA silencing, with: (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the miRNA inhibition is stimulated in the cell by contacting the cell with a composition of an miRNA inhibitory agent which is associated or conjugated to iNOP-7, and wherein the target miRNA is associated with a disease selected from metabolic syndrome, cancer, atherosclerosis, arteriosclerosis, hypercholesterolemia, and hepatitis C.

In another embodiment, the invention provides methods for inhibiting miRNA in a cell in vitro by contacting the cell, in an amount sufficient to stimulate miRNA silencing, with: (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the miRNA inhibition is stimulated in the cell by contacting the cell with a composition of an miRNA inhibitory agent which is associated or conjugated to iNOP-7, and wherein the target miRNA is associated with hypercholesterolemia.

In another embodiment, the invention provides methods for inhibiting miRNA in a cell in vitro by contacting the cell, in an amount sufficient to stimulate miRNA silencing, with: (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the miRNA inhibition is stimulated in the cell by contacting the cell with a composition of an miRNA inhibitory agent which is associated or conjugated to iNOP-7, and wherein the target miRNA is associated with hypercholesterolemia, wherein the cholesterol level of the subject decreases by at least 5% as compared to the cholesterol level of the subject prior to administration of the composition.

In another embodiment, the invention provides methods for inhibiting miRNA in a cell in vitro by contacting the cell, in an amount sufficient to stimulate miRNA silencing, with: (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the miRNA inhibition is stimulated in the cell by contacting the cell with a composition of an miRNA inhibitory agent which is associated or conjugated to iNOP-7, and wherein the target miRNA is associated with hypercholesterolemia, wherein the cholesterol level of the subject decreases by at least 5% as compared to the cholesterol level of the subject prior to administration of the composition, and wherein the nucleic acid is set forth in SEQ ID NO: 1.

In another embodiment, the invention provides a nucleic acid molecule, wherein the nucleic acid is set forth in SEQ ID NO: 1.

In another embodiment, the invention provides a nucleic acid molecule, wherein the nucleic acid is set forth in SEQ ID NO: 1, wherein the nucleic acid molecule is associated or conjugated with nanotransporter of a core conjugated with at least one functional surface group.

In another embodiment, the invention provides a nucleic acid molecule, wherein the nucleic acid is set forth in SEQ ID NO: 1, wherein the nucleic acid molecule is associated or conjugated with nanotransporter of a core conjugated with at least one functional surface group, and wherein the core is a nanoparticle.

In another embodiment, the invention provides a nucleic acid molecule, wherein the nucleic acid is set forth in SEQ ID NO: 1, wherein the nucleic acid molecule is associated or conjugated with nanotransporter of a core conjugated with at least one functional surface group, and wherein the core is a nanoparticle, wherein the nanoparticle is a dendrimer.

In another embodiment, the invention provides a nucleic acid molecule, wherein the nucleic acid is set forth in SEQ ID NO: 1, wherein the nucleic acid molecule is associated or conjugated with nanotransporter of a core conjugated with at least one functional surface group, wherein the core is a nanoparticle, wherein the nanoparticle is a dendrimer, and wherein the dendrimer is a polylysine dendrimer.

In another embodiment, the invention provides a nucleic acid molecule, wherein the nucleic acid is set forth in SEQ ID NO: 1, wherein the nucleic acid molecule is associated or conjugated with nanotransporter of a core conjugated with at least one functional surface group, and wherein the core is a nanoparticle, wherein the core is a nanotube.

In another embodiment, the invention provides a nucleic acid molecule, wherein the nucleic acid is set forth in SEQ ID NO: 1, wherein the nucleic acid molecule is associated or conjugated with nanotransporter of a core conjugated with at least one functional surface group, and wherein the core is a nanoparticle, wherein the core is a nanotube, and wherein the nanotube is a single-walled nanotube.

In another embodiment, the invention provides a nucleic acid molecule, wherein the nucleic acid is set forth in SEQ ID NO: 1, wherein the nucleic acid molecule is associated or conjugated with nanotransporter of a core conjugated with at least one functional surface group, and wherein the core is a nanoparticle, wherein the core is a nanotube, and wherein the nanotube is a multi-walled nanotube.

In another embodiment, the invention provides a nucleic acid molecule, wherein the nucleic acid is set forth in SEQ ID NO: 1, wherein the functional surface group is at least one of a lipid, a cell type specific targeting moiety, a fluorescent molecule, and a charge controlling molecule.

In another embodiment, the invention provides a nucleic acid molecule, wherein the nucleic acid is set forth in SEQ ID NO: 1, wherein the functional surface group is at least one of a lipid, a cell type specific targeting moiety, a fluorescent molecule, and a charge controlling molecule, and wherein the targeting moiety is a tissue-selective peptide.

In another embodiment, the invention provides a nucleic acid molecule, wherein the nucleic acid is set forth in SEQ ID NO: 1, wherein the functional surface group is at least one of a lipid, a cell type specific targeting moiety, a fluorescent molecule, and a charge controlling molecule, wherein the targeting moiety is a tissue-selective peptide, and wherein the lipid is an oleoyl lipid or derivative thereof.

In another embodiment, the invention provides a composition of a nanotransporter interfering nanoparticle-7 (iNOP-7) associated or conjugated with an agent that inhibits expression of a microRNA (miRNA), wherein the miRNA is selected from miRNA-122, miRNA-17, miRNA-16, miRNA-130, and miRNA-196, wherein the iNOP-7 is functionalized with any of groups A-J:

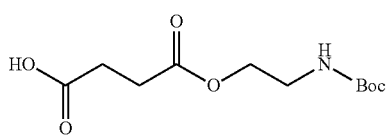

A

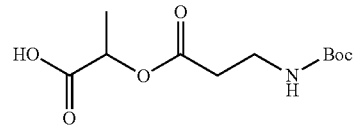

B

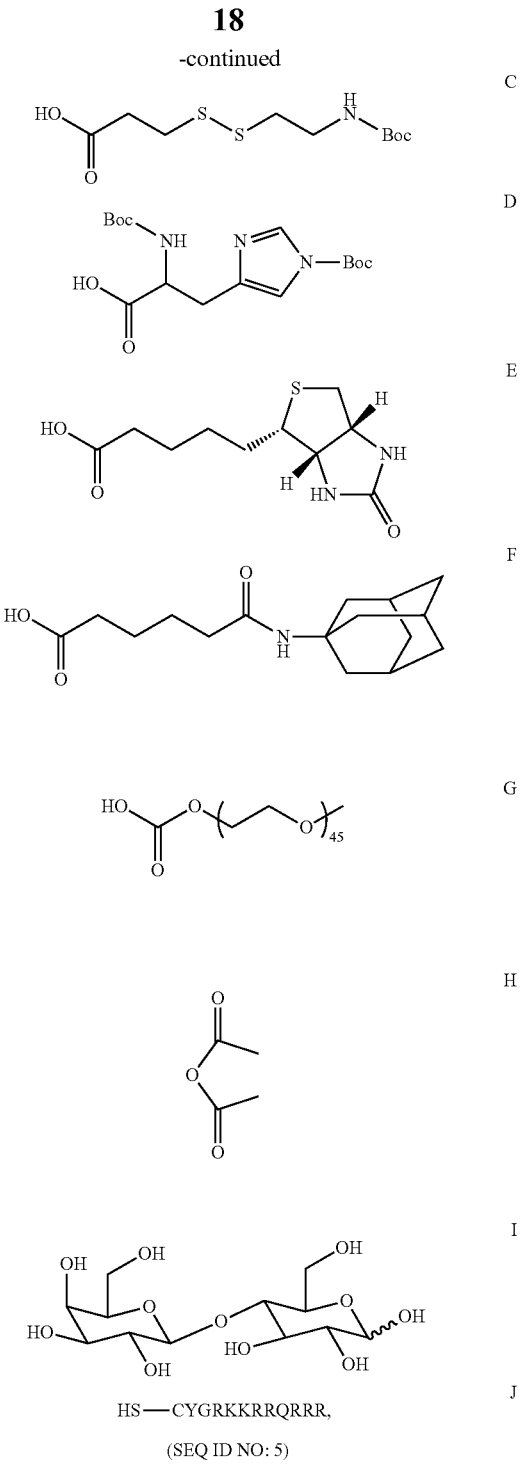

wherein A forms iNOP-7E; B forms iNOP-7LE; C forms iNOP-7DS; D forms iNOP-7His; E-forms iNOP-7Bio; F forms iNOP-7AD; G forms iNOP-7PEG; H forms iNOP-7A; I forms iNOP-7Lac; and J forms iNOP-7TAT.

In another embodiment, the invention provides a composition of a nanotransporter interfering nanoparticle-7 (iNOP-7) associated or conjugated with an agent that inhibits expression of a microRNA (miRNA), wherein the miRNA is selected from miRNA-122, miRNA-17, miRNA-16, miRNA-130, and miRNA-196, and wherein the iNOP-7 is functionalized with group I:

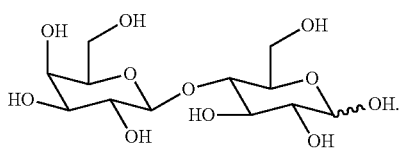

I

In another embodiment, the invention provides methods for tissue specific delivery of RNAi by modified iNOPs, by administering the modified iNOP composition of a nanotransporter interfering nanoparticle-7 (iNOP-7) associated or conjugated with an agent that inhibits expression of a microRNA (miRNA), wherein the miRNA is selected from miRNA-122, miRNA-17, miRNA-16, miRNA-130, and miRNA-196, wherein the iNOP-7 is functionalized with any of groups A-J, wherein A forms iN0P-7E; B forms iN0P-7LE; C forms iN0P-7DS; D forms iN0P-7His; E-forms iN0P-7Bio; F forms iN0P-7AD; G forms iN0P-7PEG; H forms iN0P-7A; I forms iN0P-7Lac; and J forms iN0P-7TAT.

In another embodiment, the invention provides methods for tissue specific delivery of RNAi by modified iNOPs, by administering the modified iNOP composition of a nanotransporter interfering nanoparticle-7 (iNOP-7) associated or conjugated with an agent that inhibits expression of a microRNA (miRNA), wherein the miRNA is selected from miRNA-122, miRNA-17, miRNA-16, miRNA-130, and miRNA-196, wherein the iNOP-7 is functionalized with any of groups A-J, wherein A forms iN0P-7E; B forms iN0P-7LE; C forms iN0P-7DS; D forms iN0P-7His; E-forms iN0P-7Bio; F forms iN0P-7AD; G forms iN0P-7PEG; H forms iN0P-7A; I forms iN0P-7Lac; and J forms iN0P-7TA, and wherein the modified iNOPs are delivered to the liver, spleen and/or lung.

In another embodiment, the invention provides methods for tissue specific delivery of RNAi by modified iNOPs, by administering the modified iNOP composition of a nanotransporter interfering nanoparticle-7 (iNOP-7) associated or conjugated with an agent that inhibits expression of a microRNA (miRNA), wherein the miRNA is selected from miRNA-122, miRNA-17, miRNA-16, miRNA-130, and miRNA-196, wherein the iNOP-7 is functionalized with group I:

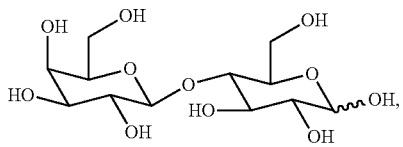

I and wherein the modified iNOP-7Lac is delivered to the liver.

In another embodiment, the invention provides a composition of a nanotransporter interfering nanoparticle-7 (iNOP-7) associated or conjugated with an agent that inhibits expression of a microRNA (miRNA), wherein the iNOP-7 is functionalized with any of groups A-J:

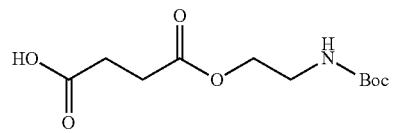

A

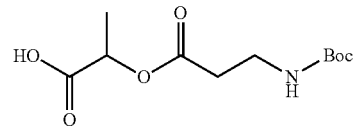

B

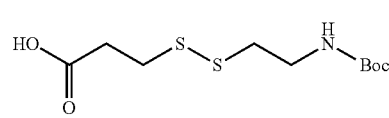

C

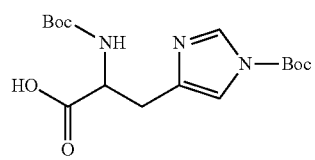

D

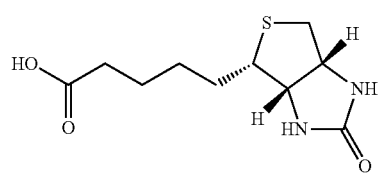

E

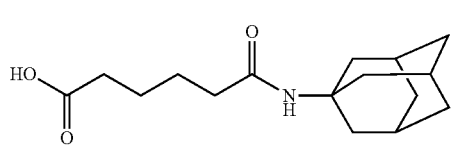

F

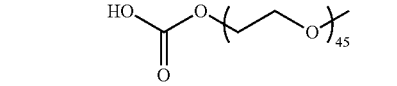

G

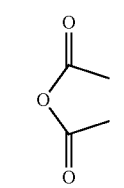

H

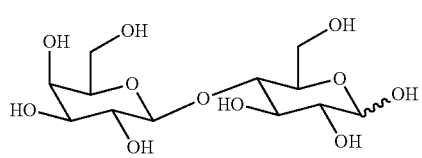

I

HS—CYGRKKRRQRRR, (SEQ ID NO: 5)

J wherein A forms iN0P-7E; B forms iN0P-7LE; C forms iN0P-7DS; D forms iN0P-7His; E-forms iN0P-7Bio; F forms iN0P-7AD; G forms iN0P-7PEG; H forms iN0P-7A; I forms iN0P-7Lac; and J forms iN0P-7TAT, and wherein the agent inhibits expression of miR-122.

In another embodiment, the invention provides a composition of a nanotransporter interfering nanoparticle-7 (iNOP-7) associated or conjugated with an agent that inhibits expression of a microRNA (miRNA), wherein the iNOP-7 is functionalized with any of groups A-J, and wherein the agent is an anti-miRNA oligonucleotide.

In another embodiment, the invention provides a composition of a nanotransporter interfering nanoparticle-7 (iNOP-7) associated or conjugated with an agent that inhibits expression of a microRNA (miRNA), wherein the iNOP-7 is functionalized with any of groups A-J, wherein the agent is an anti-miRNA oligonucleotide, and wherein the anti-miRNA oligonucleotide is an antisense oligonucleotide.

In another embodiment, the invention provides a composition of a nanotransporter interfering nanoparticle-7 (iNOP-7) associated or conjugated with an agent that inhibits expression of a microRNA (miRNA), wherein the iNOP-7 is functionalized with any of groups A-J, wherein the agent is an anti-miRNA oligonucleotide, wherein the anti-miRNA oligonucleotide is an antisense oligonucleotide, and wherein the anti-miRNA oligonucleotide is chemically modified.

In another embodiment, the invention provides a composition of a nanotransporter interfering nanoparticle-7 (iNOP-7) associated or conjugated with an agent that inhibits expression of a microRNA (miRNA), wherein the iNOP-7 is functionalized with any of groups A-J, wherein the agent is an anti-miRNA oligonucleotide, wherein the anti-miRNA oligonucleotide is an antisense oligonucleotide, wherein the anti-miRNA oligonucleotide is chemically modified, and wherein the anti-miRNA oligonucleotide is about 7-25 nucleotides in length.

In another embodiment, the invention provides a composition of a nanotransporter interfering nanoparticle-7 (iNOP-7) associated or conjugated with an agent that inhibits expression of a microRNA (miRNA), wherein the iNOP-7 is functionalized with any of groups A-J, wherein the agent is an anti-miRNA oligonucleotide, wherein the anti-miRNA oligonucleotide is an antisense oligonucleotide, wherein the anti-miRNA oligonucleotide is chemically modified, and wherein at least three of the nucleotides of the anti-miRNA oligonucleotide are chemically modified.

In another embodiment, the invention provides a composition of a nanotransporter interfering nanoparticle-7 (iNOP-7) associated or conjugated with an agent that inhibits expression of a microRNA (miRNA), wherein the iNOP-7 is functionalized with any of groups A-J, wherein the agent is an anti-miRNA oligonucleotide, and wherein the oligonucleotide is set forth in SEQ ID NO:1.

In another embodiment, the invention provides methods for delivering a nucleic acid molecule to a cell in vive by contacting a cell with iNOP-7 associated or conjugated with an agent that inhibits expression of an miRNA (miRNA), wherein the iNOP-7 is functionalized with any of groups A-J, wherein A forms iNOP-7E; B forms iNOP-7LE; C forms iNOP-7DS; D forms iNOP-7His; E-forms iNOP-7Bio; F forms iNOP-7AD; G forms iNOP-7PEO; H forms iNOP-7A; I forms iNOP-7Lac; and J forms iNOP-7TAT, thereby delivering the nucleic acid molecule.

In another embodiment, the invention provides methods for delivering a nucleic acid molecule to a cell in vivo by contacting a cell with iNOP-7 associated or conjugated with an agent that inhibits expression of an miRNA (miRNA), wherein the iNOP-7 is functionalized with any of groups A-J, and wherein the modified iNOPs are delivered to the liver, spleen and/or lung.

In another embodiment, the invention provides methods for delivering a nucleic acid molecule to a cell in vivo by contacting a cell with iNOP-7 associated or conjugated with an agent that inhibits expression of an miRNA (miRNA), wherein the iNOP-7 is functionalized with group I:

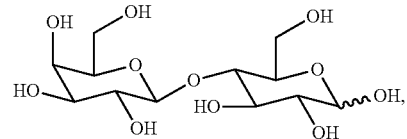

and
wherein the modified iNOP-7Lac is delivered to the liver.

In another embodiment, the invention provides methods for inhibiting expression of an miRNA in a cell in vivo by contacting the cell with iNOP-7 conjugated or associated with an agent that inhibits expression of an miRNA (miRNA), wherein the iNOP-7 is functionalized with any of groups A-J, wherein A forms iNOP-7E; B forms iNOP-7LE; C forms iNOP-7DS; D forms iNOP-7His; E-forms iNOP-7Bio; F forms iNOP-7AD; G forms iNOP-7PEG; H forms iNOP-7A; I forms iNOP-7Lac; and J forms iNOP-7TAT, thereby inhibiting expression of an miRNA.

In another embodiment, the invention provides methods for inhibiting expression of an miRNA in a cell in vivo by contacting the cell with iNOP-7 conjugated or associated with an agent that inhibits expression of an miRNA (miRNA), wherein the iNOP-7 is functionalized with any of groups A-J, and wherein the cell is a human cell.

In another embodiment, the invention provides methods for inhibiting expression of an miRNA in a cell in vivo by contacting the cell with iNOP-7 conjugated or associated with an agent that inhibits expression of an miRNA (miRNA), wherein the iNOP-7 is functionalized with any of groups A-J, and wherein the cell is a liver cell.

In another embodiment, the invention provides methods for inhibiting expression of an miRNA in a cell in viva by contacting the cell with iNOP-7 conjugated or associated with an agent that inhibits expression of an miRNA (miRNA), wherein the iNOP-7 is functionalized with any of groups A-J, and wherein the miRNA inhibitory agent is delivered at a dose of about 0.1 to about 10 mg/kg.

In another embodiment, the invention provides methods for inhibiting expression of an miRNA in a cell in vivo by contacting the cell with iNOP-7 conjugated or associated with an agent that inhibits expression of an miRNA (miRNA), wherein the iNOP-7 is functionalized with any of groups A-J, and wherein the modified iNOPs are delivered to the liver, spleen and/or lung.

In another embodiment, the invention provides methods for inhibiting expression of an miRNA in a cell in vivo by contacting the cell with iNOP-7 conjugated or associated with an agent that inhibits expression of an miRNA (miRNA), wherein the iNOP-7 is functionalized with group I:

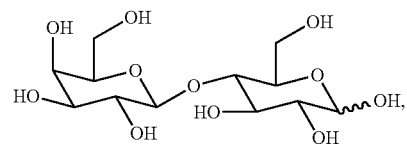

and
wherein the modified iNOP-7Lac is delivered to the liver.

In another embodiment, the invention provides a composition of an iNOP-7 that is associated or conjugated with: (a)

a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the iNOP-7 is functionalized with any of groups A-J, wherein A forms iN0P-7E; B forms iN0P-7LE; C forms iN0P-7DS; D forms iN0P-7His; E-forms iN0P-7Bio; F forms iN0P-7AD; G forms iN0P-7PEG; H forms iN0P-7A; I forms iN0P-7Lac; and J forms iN0P-7TAT, thereby inhibiting expression of an miRNA.

In another embodiment, the invention provides methods for inhibiting miRNA in a cell in vitro by contacting the cell, in an amount sufficient to stimulate miRNA silencing, with (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the miRNA inhibition is stimulated in the cell by contacting the cell with a composition of an miRNA inhibitory agent which is associated or conjugated to iNOP-7, wherein the iNOP-7 is functionalized with any of groups A-J, wherein A forms iN0P-7E; B forms iN0P-7LE; C forms iN0P-7DS; D forms iN0P-7His; E-forms iN0P-7Bio; F forms iN0P-7AD; G forms iN0P-7PEO; H forms iN0P-7A; I forms iN0P-7Lac; and J forms iN0P-7TAT, thereby inhibiting expression of an miRNA.

In another embodiment, the invention provides methods for inhibiting miRNA in a cell in vitro by contacting the cell, in an amount sufficient to stimulate miRNA silencing, with (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the miRNA inhibition is stimulated in the cell by contacting the cell with a composition of an miRNA inhibitory agent which is associated or conjugated to iNOP-7, wherein the iNOP-7 is functionalized with any of groups A-J, and wherein the target miRNA is associated with a disease selected from metabolic syndrome, cancer, atherosclerosis, arteriosclerosis, hypercholesterolemia, and hepatitis C.

In another embodiment, the invention provides methods for inhibiting miRNA in a cell in vitro by contacting the cell, in an amount sufficient to stimulate miRNA silencing, with (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the miRNA inhibition is stimulated in the cell by contacting the cell with a composition of an miRNA inhibitory agent which is associated or conjugated to iNOP-7, wherein the iNOP-7 is functionalized with any of groups A-J, and wherein the target miRNA is associated with hypercholesterolenia.

In another embodiment, the invention provides methods for inhibiting miRNA in a cell in vitro by contacting the cell, in an amount sufficient to stimulate miRNA silencing, with (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the miRNA inhibition is stimulated in the cell by contacting the cell with a composition of an miRNA inhibitory agent which is associated or conjugated to iNOP-7, wherein the iNOP-7 is functionalized with any of groups A-J, wherein the target miRNA is associated with hypercholesterolemia, and wherein the cholesterol level of the subject decreases by at least 5% as compared to the cholesterol level of the subject prior to administration of the composition.

In another embodiment, the invention provides methods for inhibiting miRNA in a cell in vitro by contacting the cell, in an amount sufficient to stimulate miRNA silencing, with (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the miRNA inhibition is stimulated in the cell by contacting the cell with a composition of an miRNA inhibitory agent which is associated or conjugated to iNOP-7, wherein the iNOP-7 is functionalized with any of groups A-J, wherein the target miRNA is associated with hypcrcholesterolemia, and wherein the nucleic acid is set forth in SEQ ID NO:1.

In another embodiment, the invention provides methods for inhibiting miRNA in a cell in vitro by contacting the cell, in an amount sufficient to stimulate miRNA silencing, with (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the miRNA inhibition is stimulated in the cell by contacting the cell with a composition of an miRNA inhibitory agent which is associated or conjugated to iNOP-7, wherein the iNOP-7 is functionalized with any of groups A-J, wherein A forms iN0P-7E; B forms iN0P-7LE; C forms iN0P-7DS; D forms iN0P-7His; E-forms iN0P-7Bio; F forms iN0P-7AD; G forms iN0P-7PEG; H forms iN0P-7A; I forms iN0P-7Lac; and J forms iN0P-7TAT, thereby inhibiting expression of an miRNA, and wherein the modified iNOPs are delivered to the liver, spleen and/or lung.

In another embodiment, the invention provides methods for inhibiting miRNA in a cell in vitro by contacting the cell, in an amount sufficient to stimulate miRNA silencing, with (a) a single-stranded 5' antisense sequence wherein the sequence is complementary to an miRNA sequence to specifically target and interfere with expression of the miRNA; and (b) the sequence is modified with more than one chemically modified nucleotides such that in vivo stability is enhanced as compared to a corresponding unmodified nucleic acid sequence, wherein the miRNA inhibition is stimulated in the cell by contacting the cell with a composition of an miRNA inhibitory agent which is associated or conjugated to iNOP-7, wherein the iNOP-7 is functionalized with group I:

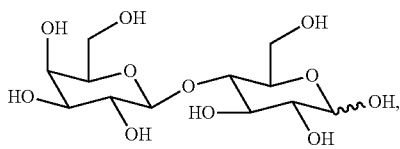

I and wherein the modified iNOP-7Lac is delivered to the liver.

In another embodiment, the invention provides a nucleic acid molecule, wherein the nucleic acid is set forth in SEQ ID NO: 1, wherein the nucleic acid molecule is associated or conjugated with an iNOP-7, wherein the iNOP-7 is functionalized with any of groups A-J, wherein A forms iN0P-7E; B forms iN0P-7LE; C forms iN0P-7DS; D forms iN0P-7His; E-forms iN0P-7Bio; F forms iN0P-7AD; G forms iN0P-7PEG; H forms iN0P-7A; I forms iN0P-7Lac; and J forms iN0P-7TAT.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this invention and so forth.

Unless defined otherwise, all technical and scientific terms used herein have the same meaning as commonly understood by one of ordinary skill in the art to which this invention pertains. Although any methods and materials similar or equivalent to those described herein can be used in the practice of testing the invention, the methods and materials are now described.

As used herein, the term "nanoparticle" refers to a particle with controlled dimensions on the order of nanometers, e.g., on the order of about 1 to about 500 nanometers, for example about 10 to about 100 nanometers. In certain embodiments, nanoparticles are dendrimers.

As used herein, the term "dendrimer" refers to a highly branched polymer with a well-defined structure. The dendrimers of the invention include but are not limited to the following: polylysine dendrimers; Polyamidoamine (PAMAM) PAMAM: Amine terminated and/or PAMAM: Carboxylic Acid terminated (available, e.g., from Dendritech, Inc., Midland, Mich.); Diaminobutane (DAB)-DAB: Amine terminated and/or DAB: Carboxylic Acid terminated; PEGs: OH terminated (Frechet et al. JACS 123:5908 (2001)), among others.

The term "nanotube" as used herein, refers to a hollow cylindrical structure with an outside diameter of about 1 to about 5 nanometers. Exemplary nanotubes are carbon nanotubes. In certain embodiments, the nanotube is a single-walled nanotube, i.e., a single tube. In other embodiments, the nanotube is a multi-walled nanotube, i.e., a tube with at least one other tube embedded within it.

As used herein, the term "nanotransporter" refers to a multi-component complex with controlled dimensions, e.g., a diameter or radius on the order of about 1 to about 1000 nanometers. In one embodiment, the nanotransporter is about 1 to about 100 nanometers in diameter. In another embodiment, the nanotransporter is about 1 to about 75 nanometers in diameter. In another embodiment, the nanotransporter is about 10, 20, 30, 40, 50, 60, 70, 80, 90, or 100 nanometers in diameter. In certain embodiments, nanotransporters comprise a nanoparticle, as defined herein, and at least one functional surface group as described herein. In one embodiment, the nanotransporters comprise about 1 to about 50 functional surface groups. In another embodiment, the nanotransporters comprise about 1 to about 25 functional surface groups. In another embodiment, the nanotransporters comprise about 1 to about 10 functional surface groups (e.g., 1, 2, 3, 4, 5, 6, 7, 8, 9, or 10 functional surface groups). In certain embodiments, the functional surface groups are the same. In other embodiments, different combinations of functional surface groups are used (e.g., 2, 3, 4, 5, or 6 types of functional surface groups are used, e.g., an oleoyl lipid and a cholesterol).

As used herein, the term "delivery complex" (also referred to as a interfering nanoparticle or "iNOP") refers to a complex formed by association of a nanotransporter and an agent, such as a nucleic acid, for example an RNA silencing agent and/or pharmaceutical agent. Delivery complexes have two portions or subunits: (1) a nanotransporter (e.g., a core conjugated with at least one functional group); and (2) an agent, such as an RNA silencing agent, for example, a chemically-modified or unmodified RNA silencing agent, including chemically modified or unmodified miRNA. In one embodiment, the delivery complex is about 1 to about 5000 nanometers in diameter. In another embodiment, the delivery complex is about 1 to about 1000 nanometers in diameter. In another embodiment, the delivery complex is about 100, 200, 300, 400, 500, 600, 700, 800, 900, or 1000 nanometers in diameter.

As used herein, the term "RNA silencing" refers to a group of sequence-specific regulatory mechanisms (e.g., RNA interference (RNAi), transcriptional gene silencing (TOS), post-transcriptional gene silencing (PTGS), quelling, co-suppression, and translational repression) mediated by RNA molecules which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence", e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g., promoter or enhancer elements) of a target gene. In other embodiments, the target polynucleotide sequence is a target mRNA encoded by a target gene.

As used herein, the term "target gene" is a gene whose expression is to be substantially inhibited or "silenced." This silencing can be achieved by RNA silencing, for example by cleaving the mRNA of the target gene or by translational repression of the target gene. The term "non-target gene" is a gene whose expression is not to be substantially inhibited. In one embodiment, the polynucleotide sequences of the target and non-target gene (e.g., mRNA encoded by the target and non-target genes) can differ by one or more nucleotides. In another embodiment, the target and non-target genes can differ by one or more polymorphisms. In another embodiment, the target and non-target genes can share less than 100% sequence identity. In another embodiment, the non-target gene may be a homolog (e.g., an ortholog or paralog) of the target gene.

A "target allele" is an allele whose expression is to be selectively inhibited or "silenced." This silencing can be achieved by RNA silencing, such as, for example, by cleaving the mRNA of the target gene or target allele by an siRNA. The term "non-target allele" is a allele whose expression is not to be substantially inhibited. In certain embodiments, the target and non-target alleles can correspond to the same target gene. In other embodiments, the target allele corresponds to a target gene, and the non-target allele corresponds to a non-target gene. In one embodiment, the polynucleotide sequences of the target and non-target alleles can differ by one or more nucleotides. In another embodiment, the target and non-target alleles can differ by one or more allelic polymorphisms. In another embodiment, the target and non-target alleles can share less than 100% sequence identity.

The term "polymorphism" as used herein, refers to a variation (e.g., a deletion, insertion, or substitution) in a gene sequence that is identified or detected when the same gene sequence from different sources or subjects (but from the same organism) are compared. For example, a polymorphism can be identified when the same gene sequence from different subjects (but from the same organism) are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to the polymorphic region. Alternatively, the polymorphism can be identified when two alleles of the same gene are compared.

A variation in sequence between two alleles of the same gene within an organism is referred to herein as an "allelic polymorphism". The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene.

As used herein, the term "RNA silencing agent" refers to an RNA which is capable of inhibiting or "silencing" the expression of a target gene. In certain embodiments, the RNA silencing agent is capable of preventing complete processing (e.g., the full translation and/or expression) of a mRNA molecule through a post-transcriptional silencing mechanism. RNA silencing agents include small (<50 b.p.), noncoding RNA molecules, for example RNA duplexes comprising paired strands, as well as precursor RNAs from which such small non-coding RNAs can be generated. Exemplary RNA silencing agents include siRNAs, miRNAs, siRNA-like duplexes, and dual-function oligonucleotides as well as precursors thereof. In a certain embodiment, the RNA silencing agent is capable of silencing miRNA either by an RNA-induced silencing complex (RISC)-like ribonucleoprotein particle (miRNP) which inhibits translations or, depending on the degree of Watson-Crick complementarity, induces degradation of target mRNAs. In another embodiment, the RNA silencing agent is capable of inducing RNA interference (RNAi). In yet another embodiment, the RNA silencing agent is capable of mediating translational repression.

As used herein, the term "microRNA inhibitor" or "anti-microRNA" is synonymous with the term "microRNA antagonist". Additionally, the term "microRNA mimic" is synonymous with the term "microRNA agonist".

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, $^2$N-methylguanosine and $^{2,2}$N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, i-methyl inosine, pseudouridine, 5,6-dihydrouridine, ribothymidine, 2N-methylguanosine and $^{2,2}$N,N-dimethylguanosine.

The term "nucleotide analog" or "altered nucleotide" or "modified nucleotide" refers to a non-standard nucleotide, including non-naturally occurring ribonucleotides or deoxyribonucleotides. Nucleotide analogs may be modified at any position so as to alter certain chemical properties of the nucleotide yet retain the ability of the nucleotideanalog to perform its intended function. Examples of modified nucleotides include, but are not limited to, 2-amino-guanosine, 2-amino-adenosine, 2,6-diamino-guanosine and 2,6-di-amino-adenosine. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, and the like.

Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, *Antisense Nucleic Acid Drug Dev.*, 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted C1-C6 alkyl, alkenyl, alkynyl, aryl, and the like. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, *Antisense Nucleic Acid Drug Dev.* 2000 Apr. 10(2): 117-21, Rusckowski et al. *Antisense Nucleic Acid Drug Dev.* 2000 Oct. 10(5):333-45, Stein, *Antisense Nucleic Acid Drug Dev.* 2001 Oct. 11(5): 317-25, Vorobjev et al. *Antisense Nucleic Acid Drug Dev.* 2001 Apr. 11(2): 77-85, and U.S. Pat. No. 5,684,143. Certain of the above-referenced modifications (e.g., phosphate group modifications) decrease the rate of hydrolysis of, for example, polynucleotides comprising the analogs in vivo or in vitro.

The term "oligonucleotide" refers to a short polymer of nucleotides and/or nucleotide analogs. The term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. The oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, and/or phosphorothioate linkages. Exemplary RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA silencing (e.g., RNA interference). In an exemplary embodiment, oligonucleotides comprise Locked Nucleic Acids (LNAs) or Peptide Nucleic Acids (PNAs).

As used herein, the term "bond strength" or "base pair strength" refers to the strength of the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, Van der Waals interactions, and the like between the nucleotides (or nucleotide analogs).

As used here, the term "melting temperature" or "Tm" refers to the temperature at which half of a population of double-stranded polynucleotide molecules becomes dissociated into single strands.

As used herein, the terms "sufficient complementarity" or "sufficient degree of complementarity" mean that the RNA silencing agent has a sequence (e.g., in the antisense strand, mRNA targeting moiety or miRNA recruiting moiety) which is sufficient to bind the desired target RNA respectively, and to trigger the RNA silencing of the target mRNA.

As used herein, the term "translational repression" refers to a selective inhibition of mRNA translation. Natural translational repression proceeds via miRNAs cleaved from shRNA precursors. Both RNAi and translational repression are mediated by RISC. Both RNAi and translational repression occur naturally or can be initiated by the hand of man, for example, to silence the expression of target genes.

As used herein, the term "small interfering RNA" ("siRNA") (also referred to in the art as "short interfering RNAs") refers to an RNA (or RNA analog) comprising between about 5-60 nucleotides (or nucleotide analogs) which is capable of directing or mediating RNA silencing (e.g., RNA interference or translational repression). A siRNA may comprise between about 15-30 nucleotides or nucleotide analogs, between about 16-25 nucieotides (or nucleotide analogs), between about 18-23 nucleotides (or nucleotide analogs), and between about 19-22 nucleotides (or nucleotide analogs) (e.g., 19, 20, 21 or 22 nucleotides or nucleotide analogs). The term "short" siRNA refers to a siRNA comprising 5-23 nucleotides, ~21 nucleotides (or nucleotide analogs), for example, 19, 20, 21 or 22 nucleotides. The term "long" siRNA refers to a siRNA comprising 24-60 nucleotides, ~24-25 nucleotides, for example, 23, 24, 25 or 26 nucleotides. Short siRNAs may, in some instances, include fewer than 19 nucleotides, e.g., 16, 17 or 18 nucleotides, or as few as 5 nucleotides, provided that the shorter siRNA retains the ability to mediate RNAi. Likewise, long siRNAs may, in some instances, include more than 26 nucleotides, e.g., 27, 28, 29, 30, 35, 40, 45, 50, 55, or even 60 nucleotides, provided that the longer siRNA retains the ability to mediate RNAi or translational repression absent further processing, e.g., enzymatic processing, to a short siRNA.

As used herein, the term "microRNA" ("miRNA"), also referred to in the art as "small temporal RNAs" ("stRNAs"), refers to a small (10-50 nucleotide) RNA which are genetically encoded (e.g., by viral, mammalian, or plant genomes) and are capable of directing or mediating RNA silencing. An "miRNA disorder" shall refer to a disease or disorder characterized by an aberrant expression or activity of an miRNA.

As used herein, the term "antisense strand" of an RNA silencing agent, e.g., an siRNA or RNAi agent, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g., an siRNA or RNAi agent, refers to a strand that is complementary to the antisense strand or first strand. Antisense and sense strands can also be referred to as first or second strands, the first or second strand having complementarity to the target sequence and the respective second or first strand having complementarity to the first or second strand. miRNA duplex intermediates or siRNA-like duplexes include a miRNA strand having sufficient complementarity to a section of about 10-50 nucleotides of the mRNA of the gene targeted for silencing and a miRNA strand having sufficient complementarity to form a duplex with the miRNA strand.

As used herein, the term "guide strand" refers to a strand of an RNAi agent, e.g., an antisense strand of an siRNA duplex or siRNA sequence, that enters into the RISC complex and directs cleavage of the target mRNA.

The term "engineered," as in an engineered RNA precursor, or an engineered nucleic acid molecule, indicates that the precursor or molecule is not found in nature, in that all or a portion of the nucleic acid sequence of the precursor or molecule is created or selected by man. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

An "isolated nucleic acid molecule or sequence" is a nucleic acid molecule or sequence that is not immediately contiguous with both of the coding sequences with which it is immediately contiguous (one on the 5' end and one on the 3' end) in the naturally occurring genome of the organism from which it is derived. The term therefore includes, for example, a recombinant DNA or RNA that is incorporated into a vector, into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide sequence.

As used herein, the term "isolated RNA" (e.g., "isolated shRNA", "isolated siRNA", "isolated siRNA-like duplex", "isolated miRNA", "isolated gene silencing agent", or "isolated RNAi agent") refers to RNA molecules which are substantially free of other cellular material, or culture medium when produced by recombinant techniques, or substantially free of chemical precursors or other chemicals when chemically synthesized.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, I.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

A gene "involved" in a disease or disorder includes a gene, the normal or aberrant expression or function of which effects or causes the disease or disorder or at least one symptom of the disease or disorder.

"Allele specific inhibition of expression" refers to the ability to significantly inhibit expression of one allele of a gone over another, e.g., when both alleles are present in the same cell. For example, the alleles can differ by one, two, three or more nucleotides. In some cases, one allele is associated with disease causation, e.g., a disease correlated to a dominant gain-of-function mutation.

As used herein, the term "metabolic disorder", refers to any disease or disorder that affects how the body processes substances needed to carry out physiological functions. A number of metabolic disorders share certain characteristics, i.e., they are associated the insulin resistance, lack of ability to regulate blood sugar, weight gain, and increase in body mass index. Examples of metabolic disorders include diabetes and obesity, as well as increased serum cholesterol levels (e.g., hypercholesterolemia).

The term "gain-of-function mutation" as used herein, refers to any mutation in a gene in which the protein encoded by the gene (i.e., the mutant protein) acquires a function not normally associated with the protein (i.e., the wild type protein) causes or contributes to a disease or disorder. The gain-of-function mutation can be a deletion, addition, or substitution of a nucleotide or nucleotides in the gene which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with the normal, wild-type protein.

The phrase "examining the function of a gene in a cell or organism" refers to examining or studying the expression, activity, function or phenotype arising therefrom.

Various methodologies of the instant invention include step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNAi agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

"Treatment", or "treating" as used herein, is defined as the application or administration of a therapeutic agent (e.g., a RNA silencing agent or a vector or transgene encoding same) to a patient, or application or administration of a therapeutic agent to an isolated tissue or cell line from a patient, who has a disorder with the purpose to cure, heal, alleviate, delay, relieve, alter, remedy, ameliorate, improve or affect the disease or disorder, or symptoms of the disease or disorder. The term "treatment" or "treating" is also used herein in the context of administering agents prophylactically. The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. The term "patient" includes human and other mammalian subjects that receive either prophylactic or therapeutic treatment.

The present invention provides for compositions, e.g., pharmaceutical compositions, of nanotransporters wherein the nanotransporter comprises a core with various functional surface groups attached. In some embodiments, the nucleic acid molecules, e.g., miRNA, are then delivered to the target site via the nanotransporter.

In another embodiment, pharmaceutical agents can be conjugate to the core of the nanotransporter. In some embodiments, pharmaceutical agents are then delivered to the target site via a nanotransporter.

In exemplary embodiments, the core of the nanotransporter is a nanoparticle or a nanotube. Nanotubes may be single walled ("SWNTs") or multi-walled ("MWNTs"). See, e.g., S. Iijima et al., *Nature,* 363, 603 (1993); S. Iijima, *Nature,* 354, 56 (1991). A SWNT is a single tube that is about 1 nanometer in diameter and about 1 to about 100 microns in length. MWNTs are tubes with at least one other tube embedded within it.

In some embodiments, nanotubes can have one end capped with the hemisphere of a fullerene like structure. Nanotubes have attracted increasing attention because of their unique geometry and electronic, mechanical, chemical, and thermal properties. Nanotubes for use in the present invention may be single walled or multi-walled.

In other embodiments, the nanotransporter core is a nanoparticle. Nanoparticles of the present invention include, but are not limited to dendrimers. Dendrimers are highly branched polymers with well-defined architecture. Dendrimers comprise several layers or "generations" of repeating units that all contain one or more branch points.

Dendrimers are generally prepared by condensation reactions of monomeric units having at least two reactive groups, for example by convergent or divergent synthesis. Divergent synthesis of dendrimers routinely occurs in two steps: (1) activation of the end groups on the surface of the molecule, and (2) the addition of branching monomer units. The reaction starts at a core molecule, which contains several reactive sites. Monomer units react readily with the core molecule forming the first generation of the dendrimer. The end groups of the monomer are protected however, and may be activated before addition of another monomer unit. Thus, the passive end groups are removed by a secondary reaction, and additional monomer units are then added. The resulting dendrimer contains an ordered arrangement of layered branches.

Convergent synthesis of dendrimers involves a growth process that begins from what will become the surface of the dendrimer. Similar to divergent synthesis, convergent synthesis routinely involves two steps: (1) the attachment of the outermost groups to an inner generation and (2) the attachment of the inner generations to the core molecule. In one embodiment, dendrimers of the invention are synthesized by divergent synthesis. In another embodiment, dendrimers of the invention are synthesized by convergent synthesis.

Each dendrimer includes a core molecule or "core dendron," one or more layers of internal dendrons, and an outer layer of surface dendrons. As used herein, "dendrons" are the branched molecules used to construct a dendrimer generation. The dendrons can be the same or different in chemical structure and branching functionality. The branches of dendrons can contain either chemically reactive or passive functional groups. When the surface contains chemically reactive groups, those groups may be used for further extension of dendritic growth or for modification of dendritic molecular surfaces, for example by attachment of various functional surface groups. The chemically passive groups can be used to physically modify dendritic surfaces, such as to adjust the ratio of hydrophobic to hydrophilic terminals, or to improve the solubility of the dendrimer for a particular environment.

Dendrimers of the invention are described by reference to their "generation". As used herein, "generation" refers to the number of synthetic rounds that the dendrimer has undergone. For example, the starting or "core" dendron is generation zero. The first addition of dendrons onto the core dendron is the first generation. The second addition of dendrons onto the core dendron is the second generation, etc. Reference to the generation can provide information about the number of end groups available for conjugation with other moieties, for example with various functional surface groups. In other embodiments, the dendrimers comprise one or more (e.g., 2, 3, 4, 5, 6, 7, 8, 9, or 10) branches radially terminating from the core dendron.

In certain embodiments, the dendrimers of the invention comprise natural amino acids (e.g., histidine, lysine, etc.) or synthetic derivatives thereof. In one embodiment, the dendrimers of the invention comprise about 10 to about 100 amino acid subunits. In another embodiment, the dendrimers of the invention comprise about 10 to about 75 amino acid subunits. In another embodiment, the dendrimers of the invention comprise about 10 to about 50 amino acid subunits (e.g., 10, 11, 12, 13, 14, 15, 16, 17, 18, 19, 20, 30, 40, or 50 subunits).

In certain embodiments, the dendrimer is a sulfur-containing dendrimer (i.e., comprises one or more sulfur atoms). For example, the sulfur-containing dendrimer may comprise branches which terminate at a terminal thiol group. In one embodiment, the dendrimer comprise one or more terminal thiols. The dendrimer comprises 1-20 terminal thiols (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30 terminal thiols). The dendrimer may comprise 16 terminal thiols. See, for example, PCT Application Number PCT/US2007/002210, incorporated herein by reference. In other embodiments, the dendrimers comprise branches which terminate at a free amine group (e.g., a primary amine or secondary amine). In one embodiment, the dendrimer comprise one or more terminal primary amines. In a certain embodiment, the dendrimer comprises 1-20 terminal primary amines (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100 or more terminal primary amines). In another embodiment, the dendrimer comprises 16 terminal primary amines. In yet another embodiment, the dendrimer comprises 60 or more terminal primary amines.

In a further embodiment, the dendrimer comprise one or more terminal secondary amines. In one aspect, the dendrimer comprises 1-20 terminal secondary amines (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30 terminal secondary amines). In another embodiment, the dendrimer comprises 32 terminal secondary amines. In another embodiment, the dendrimer comprises 64 terminal secondary amines.

In another embodiment, the dendrimer comprise one or more terminal carboxylates. The dendrimer may comprise 1-20 terminal carboxylates (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30 terminal carboxylates). In another embodiment, the dendrimer comprises 8 terminal carboxylates.

Many dendrimers are commercially available. The dendrimers of the invention include but are not limited to the following: polylysine dendrimers; Polyamidoamine (PAMAM); PAMAM: Amine terminated and/or PAMAM: Carboxylic Acid terminated (available, e.g., from Dendritech, Inc., Midland, Mi); Diaminobutane (DAB)-DAB: Amine terminated and/or DAB: Carboxylic Acid terminated; PEGs: OH terminated (Frechet et al. JACS 123:5908 (2001)), among others. In one embodiment, polylysine dendrimers or a variant thereof are used.

In one embodiment, the core of the nanotransporter is a polylysine generation 1 ("LDG1"). In another embodiment, the core of the nanotransporter is a polylysine generation 2 ("LDG2"). An exemplary synthesis of LDG2 is shown in PCT Application Number PCT/US2007/002210. In yet other embodiments, the dendrimer is a high molecular weight dendrimer. For example, in another embodiment, the core of the nanotransporter is a polylysine generation 1 ("LDG3"). In yet another embodiment, the core of the nanotransporter is polylysine dendrimer generation 4 ("LDG4").

In another embodiment, the core of the nanotransporter is a nanoparticle of a low molecular weight polylysine dendrimer.

In one aspect of the present invention, various functional surface groups can be conjugated to the core of the nanotransporter. As used herein, the term "functional surface group" refers to molecules that upon binding to the core increase the functionality of the nanotransporter, for example, to increase cell targeting specificity, to increase delivery of the nanotransporter to the target cell, and/or to impart a precise biological function. Examples of functional surface groups of the invention include, but are not limited to, carbohydrates, lipids, fatty acids and derivatives, fluorescent and charge controlling molecules, and cell type specific targeting moieties. In the present invention, a single type of functional surface group or multiple types of functional surface groups may be present on the surface of the core of the nanotransporter. Moreover, multiple functional surface groups (e.g., lipids) of the same or different type may be present on the core of the nanotransporter (e.g., 2, 3, 4, 5, 6, 7, 8, 9, 10, 15, 20, 25, 30, 35, 40, 50, 60, 70, 80, 90, 100, or more functional surface groups). In certain embodiments, 6 or 7 functional surface groups (e.g., 6 or 7 oleoyl lipids) are employed.

In one embodiment, the functional surface group is a lipid. Lipids are a major class of biomolecules that include fatty acids, waxes, glycerol and triacylglycerols, phospholipids and cholesterols. Without wishing to be bound by any particular theory, it is believed that the addition of a lipid to the core of the nanotransporter increases the ability of the nanotransporter to deliver the nucleic acid molecule or pharmaceutical agent to the target cell. In one embodiment, the lipid is a long chain fatty acid (e.g., an oleoyl derivative or an oleolyic acid derivative). In another embodiment, the lipid is a polyethylene glycol (PEG) derivative. In another embodiment, the lipid is a cholesterol for use as a lipid functional surface group. For example, a nanotransporter of the invention may comprise 1, 2, 3, or 4 cholesterol groups or 1, 2, 3, or 4 cholesterol groups combined with 1, 2, 3, 4, 5, 6, 7, or 8 lipid groups. In another exemplary embodiment, a nanotransporter may comprise 1-10 PEG groups, for example, 4 lipid groups together with 1-10, for example 7, lipids, and 1-50, for example 24, terminal primary amines. In another exemplary embodiment, a nanotransporter may comprise 1-10 lipid groups, for example 7 lipid groups, together with 1-10, for example 8, terminal carboxylates, and 1-50, for example 17, terminal primary amines.

The present invention is also directed to the synthesis of various lipid functional surface groups. Lipid functional surface groups of the invention can be prepared according to methods generally known in the art. In one embodiment, lipid functional surface groups are prepared according to the methods in PCT Application Number PCT/US2007/002210, which also shows the synthesis of an oleoylic acid derivative, another lipid functional surface group for use in the present invention. In one embodiment, this chain is attached directly to the core of the nanotransporter. This chain may also be attached directly to a nucleic acid molecule or pharmaceutical agent.

The lipid functional surface group can be conjugated to a low molecular weight nanoparticle such as a dendrimer.

It is understood that any lipid known in the art can be used to make lipid functional surface groups. For example, cationic lipids, neutral phospholipids or negatively charged lipids may be used. Suitable cationic lipid species which can be combined with the compounds of the invention include, but are not limited to, 1,2-bis(oleoyloxy)-3-(trimethylammonio)propane (DOTAP); N-[1,-(2,3-dioleoyloxy) propyl]-N,N,N-trimethyl ammonium chloride (DOTMA) or other N—(N,N-1-dialkoxy)-alkyl-N,N,N-trisubstituted ammonium surfactants; 1,2 dioleoyl-3-(4'-trimethylammonio) butanoyl-sn-glycerol (DOBT) or cholesterol (4'-trimethylammonia) butanoate (ChOTB) where the trimethylammonium group is connected via a butanoyl spacer arm to either the double chain (for DOTB) or cholesterol group (for ChOTB); DORI (DL-1,2-dioleoyl-3-dimethylaminopropyl-β-hydroxyethylammonium) or DORIE (DL-1,2-O-dioleoyl-3-dimethylaminopropyl-β-hydroxyethylammonium) (DORIE) or analogs thereof as disclosed in WO 93/03709; 1,2-dioleoyl-3-succinyl-sn-glycerol choline ester (DOSC); cholesterol hemisuccinate ester (ChOSC); lipopolyamines such as doctadecylamidoglycylspermine (DOGS) and dipalmitoyl phosphatidyesthanolamidospermine (DPPES), or the cationic lipids disclosed in U.S. Pat. No. 5,283,185, cholesterol-3β-carboxyamido-ethylenetrimethylammonium iodide, 1-dimethylamino-3-trimethylammonio-DL-2-propyl-cholesterol carboxylate iodide, cholesterol-3β-carboxyamidoethyleneamine, cholesterol-3β-oxysuccinamido-ethylenetrimethylammonium iodide, 1-dimethylamino-3-trimethylammonio-DL-2-propyl-cholesterol-3 β-oxysuccinate iodide, 2-[(2-trimethylammonio)-ethylmethylamino] ethyl-cholesterol-3β-oxysuccinate iodide, 3β-[N—(N',N'-dimethylaminoethane)-carbamoyl]-cholesterol (DC-chol), and 3β-[N-(polyethyleneimine)-carbamoyl]cholesterol.

Other exemplary cationic lipids include cholesterol-3β-carboxyamido-ethylenetrimethylammonium iodide, 1-dimethylamino-3-trimethylammonio-DL-2-propyl-cholesterol carboxylate iodide, cholesterol-3β-carboxyamidoethyl-eneamine, cholesterol-3β-oxysuccinamidoethylenetrimethyl-ammonium iodide, 1-dimethylamino-3-trimethyl-ammonio-DL-2-propyl-cholesterol-3β-oxysuccinate iodide, 2-[(2-trimethylammonio)ethyl-methylamino]-ethyl-cholesterol-3β-oxysuccinate iodide, 3β-[N—(N',N'dimethyl-amino-ethane)carbamoyl]-cholesterol (DC-chol), and 3β-[N—(N',N'-dimethylaminoethane)-carbamoyl]-cholesterol.

In addition to cationic lipids, other lipids may be employed. These lipids include, but are not limited to, lyso lipids of which lysophosphatidylcholine (1-oleoyllysophosphatidycholine) is an example, cholesterol, or neutral phospholipids including dioleoyl phosphatidyl ethanolamine (DOPE) or dioleoyl phosphatidylcholine (DOPC). Suitable negatively charged lipid species include, but are not limited to, phosphatidyl glycerol and phosphatidic acid or a similar phospholipid analog.

In another embodiment of the invention, the functional surface group attached to the nanotransporter core is a dye. According to one embodiment, the dye acts as a label so as to provide for easy detection of the location at which the nanotransporter binds. Dyes for use in the present invention are generally known in the art. Dyes include, but are not limited to, Fluorescein, Texas Red, Rhodamine Red, and Oregon Green 514. Examples of fluorescent dyes are found in the Molecular Probes Catalog, 6th Ed., Richard Haugland, Ed. The dyes of the invention may be conjugated to the core alone, or in combination with one or more other functional surface group.

In one embodiment, a lipid functional surface group and a dye are conjugated to the core of the nanotransporter. The lipid functional surface group and the dye can be conjugated to the core of the nanotransporter at the same time. In another embodiment, the lipid functional surface group and the dye are added to the core of the nanotransporter consecutively, e.g., either the lipid functional surface group or the dye is first conjugated, and the other is conjugated to the core of the nanotransporter.

PCT Application Number PCT/US2007/002210 shows an exemplary nanotransporter, wherein both a lipid functional surface group and a dye are conjugated to the nanoparticle core, as well as two other exemplary nanotransporters of a nanoparticle core, a lipid functional surface group and a dye.

In another embodiment, the functional surface group is comprised of a cell type specific targeting moiety. Use of cell type specific targeting moieties allows the nanotransporter complex to discriminate among distinct cell types. The addition of a cell type specific targeting moiety to the nanotransporter therefore allows the nanotransporter to impart a precise biological function.

Numerous cell type specific targeting moieties are known in the art. The targeting moiety may be a protein, peptide, carbohydrate, glycoprotein, small molecule, metal, etc. The targeting moiety may be used to target specific cells or tissues. Examples of targeting moieties include, but are not limited to, lung carcinoma cell specific peptide TP H1299.1 (Zhao, X, et al., *J. Am. Chem. Soc.* 2004, 126, 15656), lung adenocarcinoma cell specific peptide TP H2009.1 (Oyama, T., et al., *Cancer Lett.,* 2003, 202, 219), and endothelial cell targeting peptide CNGRC (SEQ ID NO: 6) (Arap, et. al., *Science* 1998, 279:377). Such targeting moieties can be synthesized using methods known in the art, for example, by using a MBHA resin.

The cell specific targeting moiety can then be conjugated directly with a nucleic acid molecule, e.g., siRNA, or a pharmaceutical agent. Similarly, this method can be used to conjugate the peptide to the core of the nanotransporter.

For example, a cyclic CNGRC (SEQ ID NO: 6) can be conjugated to the core of the nanotransporter, e.g., LDG4. Additionally, a lipid functional group, e.g., an oleoyl derivative, is conjugated to the core of the nanotransporter. The nucleic acid molecule conjugates to the nanotransporter for delivery to the target cells, e.g., endothelial cells. The nanotransporters of the present invention further can be used to deliver nucleic acid molecules, e.g., siRNA, and/or pharmaceutical agents to cancer cells.

In one embodiment, the cell-type specific targeting moiety is specific for tumor cells or virally infected cells (e.g., Transportan, Penetratin, or Tat peptide). An exemplary nanotransporter of the invention including a LDG4 core functionalized with Tat peptide is shown in PCT Application Number PCT/US2007/002210.

In another embodiment, the functional surface group is comprised of a charge controlling molecule. A "charge controlling molecule," as used herein, refers to a molecule which contributes to the overall ionic environment or net charge of a nanotransporter. In one embodiment, the addition of a charge controlling molecule facilitates the association between the nanotransporter and a siRNA molecule and the formation of a delivery complex. In another embodiment, the addition of a charge controlling molecule facilitates improved cellular uptake of the delivery complex into the cell. In certain embodiments, charge controlling molecules can be attached to a nanotransporter thereby forming a modified nanotransporter. Exemplary charge controlling molecules for use with a nanotransporter of the present invention are shown in PCT Application Number PCT/US2007/002210. In certain embodiments, the charge controlling molecules are the same chemical structure or class. In other embodiments where m is greater than 1, any combination of charge controlling molecules of different chemical structures or classes may be used. A charge controlling molecule is H-Lys-OMe. Exemplary modification of a nanotransporter with H-Lys-OMe is depicted in PCT Application Number PCT/US2007/002210.

The net charge (m) and/or the number of lipid groups (n) of the modified nanotransporter may be varied depending on the tissue that is targeted. In one embodiment, m results in a positive net charge. In another embodiment, m is a positive negative charge. In other embodiment, m is a neutral net charge. In another embodiment, m is a positive integer less than 50 (e.g., 40, 30, 20, 10, 9, 8, 7, 6, 5, 4, 3, 2, or 1). In another embodiment, n is a positive integer less than 50 (e.g., 40, 30, 20, 10, 9, 8, 7, 6, 5, 4, 3, 2, or 1). It is recognized that any combination of lipids described supra may be employed together with any combination of charge controlling molecules.

In another embodiment, the functional surface group is comprised of carbohydrate. In one embodiment, the carbohydrate is a monosaccharide (e.g., an aldose, a ketose, a triose, a tetrose, a pentose, a hexose, a heptose, an aldohexose, a ketopentose, a allose, a glucose, a mannose, a galactose, a xylose, an erythrulose, a fructose, a glucoasamine, a ribose, a rhamnose, a galactosamine, N-acetylmuramic acid, N-acetylmuramic acid, fucose, and the like). In another embodiment, the carbohydrate is a polysaccharide (e.g., a homopolysaccharide, such as cellulose, or a heteropolysaccharide). In another embodiment, the carbohydrate is a disaccharide (e.g., sucrose, lactose, maltose, cellobiose, and the like). Any epimer or other stereoisomer (e.g., L or D isomer) of a monosaccharide may be employed. Synthesis of exemplary carbohydrate-containing nanotransporters may comprise 9 disaccharides or 26 disaccharides.

In one embodiment nucleic acid molecules are delivered to a target cell via a nanotransporter. As used herein the term "nucleic acid molecule" refers to a polymer of nucleotides joined together by a phosphodiester linkage between 5' and 3' carbon atoms. Nucleic acid molecules are generally known in the art, and include, but are not limited to RNA silencing agents (e.g., siRNAs, chemically modified siRNAs, RNAi agents, miRNAs, and shRNAs), antisense molecules, ribozymes, and the like.

In certain embodiments, the present invention features RNA silencing agents (e.g., siRNA and shRNAs). The RNA silencing agents of the invention are duplex molecules (or molecules having duplex-like structure) including a sense strand and a complementary antisense strand (or portions thereof), wherein the antisense strand has sufficient complementary to a target sequence (e.g., target mRNA) to mediate an RNA silencing mechanism (e.g., RNAi or translational repression).

An siRNA molecule is a duplex consisting of a sense strand and complementary antisense strand, the antisense strand having sufficient complementary to a target mRNA sequence to direct target-specific RNA interference (RNAi), as defined herein, i.e., the siRNA has a sequence sufficient to trigger the destruction of the target mRNA by the RNAi machinery or process. In alternative embodiments, the antisense strand of the siRNA has sufficient complementarity to a target mRNA sequence to direct translation repression of the target mRNA.

The siRNA molecule may have a length from about 5-60 (e.g., about 10-50) or more nucleotides, i.e., each strand comprises 5-60 (e.g., 10-50) nucleotides (or nucleotide analogs). The siRNA molecule may have a length from about 16-30, e.g., 16, 17, 18, 19, 20, 21, 22, 23, 24, 25, 26, 27, 28, 29, or 30 nucleotides (or nucleotide analogs) in each strand, wherein one of the strands is sufficiently complementary to a target region. In other embodiments, siRNAs may have shorter or longer lengths. In one embodiment, the siRNA has a length of about 5-15 nucleotides or nucleotide analogs (e.g., 5, 6, 7, 8, 9, 10, 11, 12, 13, 14, or 15 nucleotides) in each strand, wherein one of the strands is sufficiently complementary to a target region. In another embodiment, the siRNA has a length of about 30-60 nucleotides or nucleotide analogs (e.g., 35, 40, 45, 50, 55, or 60 nucleotides in each strand, wherein one of the strands is sufficiently complementary to a target region). The strands may be aligned such that there are at least 1, 2, or 3 bases (e.g., 1-5 bases) at the end of the strands which do not align (i.e., for which no complementary bases occur in the opposing strand) such that an overhang of 1, 2 or 3 residues occurs at one or both ends of the duplex when strands are annealed. In certain embodiments, at least one or both ends of the duplex comprise a 2-nucleotide overhang (e.g., dTdT overhangs).

Generally, siRNAs can be designed by using any method known in the art, for instance, by using the following protocol.

1. A target mRNA is selected and one or more target sites are identified within the target mRNA. Cleavage of mRNA at these sites results in mRNA degradation, preventing production of the corresponding protein. Polymorphisms from other regions of the mutant gene are also suitable for targeting.

In certain embodiments, the target sequence comprises AA dinucleotide sequences; each AA and the 3' adjacent 16 or more nucleotides are potential siRNA targets. In another embodiment, the nucleic acid molecules are selected from a region of the target mRNA sequence beginning at least 50 to 100 nt downstream of the start codon, e.g., of the sequence of the target mRNA. Further, siRNAs with lower G/C content (35-55%) may be more active than those with G/C content higher than 55%. Thus in one embodiment, the invention includes target sequences having 35-55% G/C content, although the invention is not limited in this respect.

2. The sense strand of the siRNA is designed based on the sequence of the selected target site. In one embodiment the sense strand includes about 19 to 25 nucleotides, e.g. 19, 20, 21, 22, 23, 24 or 25 nucleotides. In another embodiment, the sense strand includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNAi agents have been demonstrated to elicit an interferon or PKR response in certain mammalian cells which may be undesirable. The RNAi agents of the invention may not elicit a PKR response (i.e., are of a sufficiently short length). However, longer RNAi agents may be useful, for example, in cell types incapable of generating a PRK response or in situations where the PKR response has been downregulated or dampened by alternative means.

The siRNA molecules of the invention have sufficient complementarity with the target site such that the siRNA can mediate RNAi. In general, siRNA containing nucleotide sequences sufficiently identical to a portion of the target gene to effect RISC-mediated cleavage of the target gene.

Accordingly, in a certain embodiment, the sense strand of the siRNA is designed have to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 9, 91%, 92%, 93%, 94%, 95%, 96%, 97%, 98%, 99% or even 100% identity, between the sense strand and the target RNA sequence is sufficient. The invention has the advantage of being able to tolerate certain sequence variations to enhance efficiency and specificity of RNAi. In one embodiment, the sense strand has 4, 3, 2, 1, or 0 mismatched nucleotide(s) with a target region, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, the molecules are identical at that position. The percent identity between the two sequences is a function of the number of identical positions shared by the sequences (i.e., % homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A non-limiting example of a local alignment algorithm utilized for the comparison of sequences is the algorithm of Karlin and Altschul (1990) *Proc. Natl. Acad Sci. USA* 87:2264-68, modified as in Karlin and Altschul (1993) *Proc. Natl. Acad Sci. USA* 90:5873-77. Such an algorithm is incorporated into the BLAST programs (version 2.0) of Altschul, et al. (1990) *J. Mol. Biol.* 215:403-10.

In another embodiment, the alignment is optimized by introducing appropriate gaps and percent identity is determined over the length of the aligned sequences (I.e., a gapped alignment). To obtain gapped alignments for comparison purposes, Gapped BLAST can be utilized as described in Altschul et al. (1997) *Nucleic Acids Res.* 25(17):3389-3402. In another embodiment, the alignment is optimized by introducing appropriate gaps and percent identity is determined over the entire length of the sequences aligned (i.e., a global alignment). A non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense strand sequence is designed such that nucleotides corresponding to the desired target cleavage site are essentially in the middle of the strand. For example, if a 21-nucleotide siRNA is chosen, nucleotides corresponding to the target cleavage site are at, for example, nucleotide 6, 7, 8, 9, 10, 11, 12, 13, 14, 15 or 16 (i.e., 6, 7, 8, 9, 10, 11, 12, 13, 14, 15 or 16 nucleotides from the 5' end of the sense strand. For a 22-nucleotide siRNA, nucleotides corresponding to the target cleavage site are at, for example, nucleotide 7, 8, 9, 10, 11, 12, 13, 14, 15 or 16. For a 23-nucleotide siRNA, nucleotides corresponding to the target cleavage site are at, for example, 7, 8, 9, 10, 11, 12, 13, 14, 15 or 16. For a 24-nucleotide siRNA, nucleotides corresponding to the target cleavage site are at, for example, 9, 10, 11, 12, 13, 14 or 16. For a 25-nucleotide siRNA, nucleotides corresponding to the target cleavage site are at, for example, 9, 10, 11, 12, 13, 14, 15, 16 or 17. Moving nucleotides corresponding to an off-center position may, in some instances, reduce efficiency of cleavage by the siRNA. Such compositions, i.e., less efficient compositions, may be desirable for use if off-silencing of a second (non-target) mRNA is detected.

The sense strand is designed such that complementarity exists between the antisense strand of the siRNA and the sense strand. In exemplary embodiments, the siRNA is designed such that the strands have overhanging ends, e.g., overhangs of 1, 2, 3, 4, 5 or more nucleotide at one, or both, ends of the siRNA. Exemplary overhangs are deoxynucleotide overhangs, for example, a dTdT tail.

4. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 4, e.g., 2, nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus in another embodiment, the nucleic acid molecules may have a 3' overhang of 2 nucleotides, such as TT. The overhanging nucleotides may be either RNA or DNA.

5. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

6. Select one or more sequences that meet your criteria for evaluation. Further general information about the design and use of siRNA may be found in "The siRNA User Guide," available at The Max-Plank-Institut fur Biophysikalishe Chemie website.

Alternatively, the siRNA may be defined functionally as including an antisense or guide strand having a nucleotide sequence (or oligonucleotide sequence) that is capable of hybridizing with the target sequence (e.g., 400 mM NaC, 40 mM PIPES pH 6.4, 1 mM EDTA, 50° C. or 70° C. hybridization for 12-16 hours; followed by washing). Additional hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm (° C.)=2(number of A+T bases)+4(number of G+C bases). For hybrids between 18 and 49 base pairs in length, Tm (° C.)=81.5+16.6(log 10[Na$^+$])+0.41(% G+C)−(600/N), where N is the number of bases in the hybrid, and [Na$^+$] is the concentration of sodium ions in the hybridization buffer ([Na$^+$] for 1×SSC=0.165 M). Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA; a homology search can be performed to ensure that the negative control lacks homology to any other gene in the appropriate genome. In addition, negative control siRNAs can be designed by introducing a significant number of base mismatches into the sequence.

7. To validate the effectiveness by which siRNAs destroy mutant mRNAs (e.g., mutant huntingtin mRNA), the siRNA may be incubated with mutant cDNA (e.g., mutant huntingtin cDNA) in a *Drosophila*-based in vitro mRNA expression system. Radiolabeled with $^{32}$P, newly synthesized mutant mRNAs (e.g., mutant huntingtin mRNA) are detected autoradiographically on an agarose gel. The presence of cleaved mutant mRNA indicates mRNA nuclease activity. Suitable controls include omission of siRNA. Alternatively, control siRNAs as described above are utilized.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof.

The miRNA sequence can be similar or identical to that of any naturally occurring miRNA (see e.g., The miRNA Registry; Griffiths-Jones S, Nuc. Acids Res., 2004). Over one thousand natural miRNAs have been identified to date and together they are thought to comprise ~1% of all predicted genes in the genome. Many natural miRNAs are clustered together in the introns of pre-mRNAs and can be identified in silico using homology-based searches (Pasquinclli et al., 2000; Lagos-Quintana et al., 2001; Lau et al., 2001; Lee and Ambros, 2001) or computer algorithms (e.g., MiRScan, MiRSeeker) that predict the capability of a candidate miRNA gene to form the stem loop structure of a pri-mRNA (Grad et al., *Mol. Cell*, 2003; Lim et al, *Genes Dev.*, 2003; Lim et al., *Science*, 2003; Lai E C et al., *Genome Bio.*, 2003). An online registry provides a searchable database of all published miRNA sequences (The miRNA Registry at the Sanger Institute website; Griffiths-Jones S, *Nuc. Acids Res.*, 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melemogaster, Caenorhabditis elegans*, zebrafish, *Arabidopsis thalania*, mouse, and rat as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., *Science*, 2001; Lau et al., *Science*, 2001; Lee and Ambros, *Science*, 2001; Lagos-Quintana et al., *Curr. Biol.*, 2002; Mourelatos et al., *Genes Dev.*, 2002; Reinhart et al., *Science*, 2002; Ambros et al., *Curr. Biol.*, 2003; Brennecke et al., 2003; Lagos-Quintana et al., RNA, 2003; Lim et al., *Genes Dev.*, 2003; Lim et al., *Science*, 2003). miRNAs can exist transiently in vivo as a double-stranded duplex but only one strand is taken up by the RISC complex to direct gene silencing. Certain miRNAs, e.g., plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between an miRNA and its target mRNA is believed to determine its mechanism of action. For example, perfect or near-perfect complementarity between a miRNA and its target mRNA is predictive of a cleavage mechanism (Yekta et al., *Science*, 2004), whereas less than perfect complementarity is predictive of a translational repression mechanism. In particular embodiments, the miRNA sequence is that of a naturally-occurring miRNA sequence, the aberrant expression or activity of which is correlated with a miRNA disorder.

Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the invention are artificial constructs based on these naturally occurring pre-miRNAs, but which are engineered to deliver desired RNAi agents (e.g., siRNAs of the invention). By substituting the stem sequences of the pre-miRNA with sequence complementary to the target mRNA, a shRNA is formed. The shRNA is processed by the entire gene silencing pathway of the cell, thereby efficiently mediating RNAi.

MicroRNAs (miRNAs) are small endogenous non-coding RNAs that post-transcriptionally regulate gene expression by binding with imperfect complementarity in 3' untranslated regions (3'-UTR) of their target messenger RNAs (mRNAs). MiRNAs are 18-25 nucleotide single-stranded small RNAs associated with a complex of proteins which is called RNA-induced silencing complex (RISC)-like ribonucleoprotein particle (miRNP). This complex inhibits translation or, depending on the degree of Watson-Crick complementarity, induces degradation of target mRNAs. These small RNAs are usually generated from non-coding regions of many gene transcripts and function to suppress gene expression by translational repression. MiRNAs have been shown to play important roles in development, cell growth, and differentiation. Recent studies have highlighted the role of miRNAs in various disease states and in regulating host-pathogen interactions. For example, mRNAs have been implicated in cardiovascular disease, inflammation, viral infections, and cancers. Hence, disease-associated miRNAs could become potential targets for therapeutic intervention.

MicroRNA-122 (miR-122) is a liver-specific miRNA, with suggested roles in cholesterol, fatty acid, and lipid metabolism. MiR-122 interacts with the hepatitis C virus genome, facilitating viral replication in a host cell. In vivo silencing of miR-122 has been achieved by systemic administration of a novel class of chemically engineered oligonucleotides, known as antagomirs (modified antisense oligonucleotides) in mice or non-human primates. These studies were very encouraging in providing proof of concept for silencing miRNA by its anti-miR sequences in vivo. Recently, therapeutic silencing of miR-122 in primates with chronic hepatitis C virus infection has been reported by using locked nucleic acid (LNA) modified oligonucleotide (SPC3649) complementary to miR-122. Remarkably, SPC3649 treatment caused long lasting suppression of HCV viremia in primates with no apparent evidence of side effects or viral resistance; this is strongly indicative that the anti-miR therapeutic strategy could lead to the development of new drugs for viral infections. The successful silencing of apoB mRNA by iNOP-7 after systemic administration of 1 mg $kg^{-1}$ of siRNA in mice has recently been reported. It could reasonably be conjectured that a chemically stabilized anti-miR could be assembled with iNOP-7 and could inhibit miRNA sequences in vivo. In this study, we tested this concept and determined the silencing efficiency of miR-122 using iNOP-7 in mice.

In embodiments, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g., within the 3'-UTR of the target mRNA) (Hutvagner and Zamore, *Science*, 2002; Zeng et al., *Mol. Cell*, 2002; Zeng et al., RNA, 2003; Doench et al., *Genes Dev.*, 2003). Since the mechanism of translational repression is cooperative, multiple complementarity sites (e.g., 2, 3, 4, 5 or 6) may be targeted in certain embodiments.

siRNA-like molecules of the invention have a sequence (i.e., have a strand having a sequence) that is "sufficiently complementary" to a target mRNA sequence to direct gene silencing either by RNAi or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNAi is increased.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementary site so that duplex formed by the guide strand and the target mRNA contains a central "bulge" (Doench J G et at, *Genes Dev.*, 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A.A, C:C, U:U). In a further embodiment, the "bulge" is centered at nucleotide positions 12 and 13 from the 5' end of the siRNA-like molecule.

In certain featured embodiments, the instant invention provides shRNAs capable of mediating RNA silencing of a target sequence (e.g., target mRNA) with enhanced selectivity. In contrast to siRNAs, shRNAs mimic the natural precursors of microRNAs (miRNAs) and enter at the top of the gene silencing pathway. For this reason, shRNAs are believed to mediate gene silencing more efficiently by being fed through the entire natural gene silencing pathway.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that, has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In shRNAs of the instant invention, one portion of the duplex stem is a nucleic acid sequence that is complementary (or antisense) to the target mRNA. One strand of the stem portion of the shRNA may be sufficiently complementary (e.g., antisense) to a target RNA (e.g., mRNA) sequence to mediate degradation or cleavage of the target RNA via RNA interference (RNAi). Thus, shRNAs include a duplex stem with two portions and a loop connecting the two stem portions. The antisense portion can be on the 5' or 3' end of the stem. The stem portions of a shRNA are about 15 to about 50 nucleotides in length. The two stem portions may be about 18 or 19 to about 21, 22, 23, 24, 25, 30, 35, 37, 38, 39, or 40 or more nucleotides in length. In other embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA).

The two portions of the duplex stem may be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs can be 2, 3, 4, 5, 6, 7, 8, 9, or more, e.g., 15 or 20, or more nucleotides in length.

A loop may consist of or comprise a "tetraloop" sequence. Exemplary tetraloop sequences include, but are not limited to, the sequences ONRA, where N is any nucleotide and R is a purine nucleotide, GGGG, and UUUU.

In certain embodiments, shRNAs of the invention include the sequences of a desired siRNA molecule described supra. In other embodiments, the sequence of the antisense portion of a shRNA can be designed essentially as described above or generally by selecting an 18, 19, 20, 21 nucleotide, or longer, sequence from within the target RNA, for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include in the duplex stem the 21-22 or so nucleotide sequences of the siRNA, siRNA-like duplex, or miRNA desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro.

In certain embodiments, shRNAs of the invention include miRNA sequences, optionally end-modified miRNA sequences, to enhance entry into RISC.

In other embodiments, the RNA silencing agents of the present invention include dual functional oligonucleotide tethers useful for the intercellular recruitment of a miRNA. Animal cells express a range of miRNAs, non-coding RNAs of approximately 22 nucleotides which can regulate gene expression at the post transcriptional or translational level. By binding a miRNA bound to RISC and recruiting it to a target mRNA, a dual functional oligonucleotide tether can repress the expression of genes involved e.g., in the arteriosclerotic process. The use of oligonucleotide tethers offers several advantages over existing techniques to repress the expression of a particular gene. First, the methods described herein allow an endogenous molecule (often present in abundance), an miRNA, to mediate RNA silencing; accordingly the methods described herein obviate the need to introduce foreign molecules (e.g., siRNAs) to mediate RNA silencing. Second, the RNA-silencing agents and, in particular, the linking moiety (e.g., oligonucleotides such as the 2'-O-methyl oligonucleotide), can be made stable and resistant to nuclease activity. As a result, the tethers of the present invention can be designed for direct delivery, obviating the need for indirect delivery (e.g., viral) of a precursor molecule or plasmid designed to make the desired agent within the cell. Third, tethers and their respective moieties, can be designed to conform to specific mRNA sites and specific miRNAs. The designs can be cell and gene product specific. Fourth, the methods disclosed herein leave the mRNA intact, allowing one skilled in the art to block protein synthesis in short pulses using the cell's own machinery. As a result, these methods of RNA silencing are highly regulatable.

The dual functional oligonucleotide tethers ("tethers") of the invention are designed such that they recruit miRNAs (e.g., endogenous cellular miRNAs) to a target mRNA so as to induce the modulation of a gene of interest. In certain embodiments, the tethers have the formula T-L-µ, wherein T is an mRNA targeting moiety, L is a linking moiety, and µ is an miRNA recruiting moiety. Any one or more moiety may be double stranded. However, each moiety may be single stranded.

Moieties within the tethers can be arranged or linked (in the 5' to 3' direction) as depicted in the formula T-L-μ (i.e., the 3' end of the targeting moiety linked to the 5' end of the linking moiety and the 3' end of the linking moiety linked to the 5' end of the miRNA recruiting moiety). Alternatively, the moieties can be arranged or linked in the tether as follows: μ-T-L (i.e., the 3' end of the miRNA recruiting moiety linked to the 5' end of the linking moiety and the 3' end of the linking moiety linked to the 5' end of the targeting moiety).

The mRNA targeting moiety, as described above, is capable of capturing a specific target mRNA. According to the invention, expression of the target mRNA is undesirable, and, thus, translational repression of the mRNA is desired. The mRNA targeting moiety should be of sufficient size to effectively bind the target mRNA. The length of the targeting moiety will vary greatly depending, in part, on the length of the target mRNA and the degree of complementarity between the target mRNA and the targeting moiety. In various embodiments, the targeting moiety is less than about 200, 100, 50, 30, 25, 20, 19, 18, 17, 16, 15, 14, 13, 12, 11, 10, 9, 8, 7, 6, or 5 nucleotides in length. In a particular embodiment, the targeting moiety is about 15 to about 25 nucleotides in length.

The miRNA recruiting moiety, as described above, is capable of associating with an miRNA. According to the invention, the miRNA may be any miRNA capable of repressing the target mRNA. Mammals are reported to have over 250 endogenous miRNAs (Lagos-Quintana et al. (2002) *Current Biol.* 12:735-739; Lagos-Quintana et al. (2001) *Science* 294:858-862; and Lim et al. (2003) *Science* 299:1540). In various embodiments, the miRNA may be any art-recognized miRNA.

The linking moiety is any agent capable of linking the targeting moieties such that the activity of the targeting moieties is maintained. Linking moieties may be oligonucleotide moieties including a sufficient number of nucleotides such that the targeting agents can sufficiently interact with their respective targets. Linking moieties have little or no sequence homology with cellular mRNA or miRNA sequences. Exemplary linking moieties include one or more 2'-0-methylnucleotides, e.g., 2'-0-methyladenosine, 2'-0-methylthymidine, 2'-0-methylguanosine or 2'-0-methyluridine.

In other aspects, any of the RNA silencing agents described supra may be designed such that they are capable of discriminatory RNA silencing. For example, RNA silencing agents (e.g., siRNAs) which discriminate between RNAs of related sequences may be designed. Such agents are capable of silencing a target mRNA (e.g., an mRNA associated with a disease-associated allelic polymorphism) while failing to substantially silence a related non-target mRNA (e.g., an mRNA associated with a wild-type allele corresponding to the disease allele). In certain embodiments, RNA silencing agents capable of discriminatory RNA silencing may be designed by including a nucleotide which forms a Watson-Crick base pair with an allelic polymorphism in the target mRNA (e.g., a single-nucleotide polymorphism (SNP)) but which does not form a Watson-Crick base pair but a mismatched or wobble base pair with the corresponding nucleotide in the target mRNA (e.g., wild type). For example, the RNA silencing agent may be designed such that a mismatch (e.g., a purine:purine mismatch) or wobble exists between the siRNA and the non-target mRNA (e.g., wild type mRNA) at the single nucleotide. The purine:purine pairing is selected, for example, from the group G:G, A:G, G:A and A:A pairing. Moreover, purine:pyrimidine pairing between the siRNA and the target mRNA (e.g., mutant mRNA) at the single nucleotide enhances single nucleotide specificity. The purine:pyrimidine pairing is selected, for example, from the group G:C, C.G, A:U, U:A, C:A, A:C, U:A and A:U pairing.

In other embodiments, the RNA silencing agents may be designed to discriminate between the non-target mRNA and the target mRNA by the introduction of a modified base positioned opposite the allelic polymorphism, such that the siRNA directs allele-specific cleavage of a mRNA including the polymorphism. The methods are described in International PCT Publication No. WO 04/046324, which is incorporated herein by reference. In certain embodiments, the modified base is selected from 5-bromo-uridine, 5-bromo-cytidine, 5-iodo-uridine, 5-iodo-cytidine, 2-amino-purine, 2-amino-allyl-purine, 6-amino-purine, 6-amino-allyl-purine, 2, 6-diaminopurine and 6-amino-8-bromo-purine. In an exemplary embodiment, the modified base is 5-bromo-uridine or 5-iodo-uridine and, e.g., the point mutation is an adenine. In another exemplary embodiment, the modified base is 2,6-diaminopurine and, e.g., the point mutation is a thymine.

In certain aspects, the invention features novel RNA silencing agents, e.g., novel small interfering RNAs (siR-NAs), that include a sense strand and an antisense strand, wherein the antisense strand has a sequence sufficiently complementary to a target mRNA sequence to direct target-specific RNA interference (RNAi) and wherein the sense strand and/or antisense strand is modified by the substitution of nucleotides with chemically modified nucleotides. In one embodiment, the sense strand and/or the antisense strand are modified with one or more internal chemical modifications. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or the antisense strand are modified at the 5' end and/or the 3' end. In one embodiment, the sense strand and/or the antisense strand are modified at both the 5' end and the 3' end. As used herein, the term "modified at the end" when used in reference to the 5' or 3' ends, refers to any nucleotide within 10 nucleotides of the first and last nucleotide, for example any nucleotide within 7 nucleotides of the first and last nucleotide. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the nucleotides. In yet another embodiment, the sense strand and/or antisense strand is modified by the substitution of all of the nucleotides. Within the RNAi agents employed in the methods of the invention, as few as one and as many as all nucleotides of the oligonucleotide can be modified. In some embodiments, the RNAi agent will contain as few modified nucleotides as are necessary to achieve a desired level of in vive stability and/or bioaccessibility while maintaining cost effectiveness.

Chemical modifications may lead to increased stability, e.g., increased or enhanced in vivo stability, compared to an unmodified RNAi agent or a label that can be used, e.g., to trace the RNAi agent, to purify an RNAi agent, or to purify the RNAi agent and cellular components with which it is associated. Such chemical modifications can also be used to stabilize the first (priming) strand of the siRNA or miRNA for enhancing RISC activity/RNAi responsiveness in a cell (or cell extract or organism) and improve its intracellular half-life for subsequent receipt of the second strand wherein RNAi/gene silencing can now progress. Modifications can also enhance properties such as cellular uptake of the RNAi agents and/or stability of the RNAi agents, can stabilize interactions between base pairs, and can maintain the structural integrity of the antisense RNAi agent-target RNA duplex. RNAi agent modifications can also be designed such that properties important for in vivo applications, in particular, human therapeutic applications, are improved without compromising the RNAi activity of the RNAi agents e.g., modifications to increase resistance of, e.g., siRNA, miRNA, or silencing miRNA molecules to nucleases. In certain embodiments, modified siRNA molecules of the invention can enhance the efficiency of target RNA inhibition as compared to a corresponding unmodified siRNA. In some embodiments, modified nucleotides do not affect the ability of the antisense strand to adopt A-form helix conformation when base-pairing with the target RNA sequence, e.g., an A-form helix conformation including a normal major groove when base-pairing with the target RNA sequence.

Chemical modifications generally include end-, sugar-, base- and/or backbone-modifications to the ribonucleotides (i.e., include modifications to the phosphate-sugar backbone).

In one embodiment, the RNAi agent of the invention comprises one or more (e.g., about 1, 2, 3, or 4) end modifications. For example, modification at the 5' end of an siRNA molecule comprises, for example, a 5'-propylamine group. Modifications of the 5' end may also include 5' terminal phosphate groups, such as those described by Formula I:

wherein each X and Y is independently O, S, N, alkyl, substituted alkyl, or alkylhalo; wherein each Z and W is independently O, S, N, alkyl, substituted alkyl, O-alkyl, S-alkyl, alkaryl, aralkyl, alkylhalo, or acetyl. In some embodiments, W, X, Y and Z are not all O. Modifications to the 3' OH terminus of an siRNA molecule can include, but are not limited to, 3'-puromycin, 3'-biotin (e.g., a photocleavable biotin), a peptide (e.g., a Tat peptide), a nanoparticle, a peptidomimetic, organic compounds (e.g., a dye such as a fluorescent dye), or a dendrimer. End modifications may be on the sense strand, on the antisense strand or both. In some embodiments, the 5' modifications are on the sense strand only.

In another embodiment, the RNAi agent of the invention may comprise one or more (e.g., about 1, 2, 3, 4, 5, 6, 7, 8, 9, 10, or more) sugar-modified nucleotides. Exemplary sugar modifications may include modifications represented by Formula II:

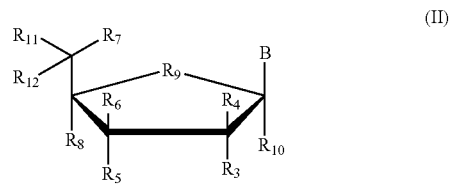

wherein each $R^3$, $R^4$, $R^5$, $R^6$, $R^7$, $R^8$, $R^{10}$, $R^{11}$ and $R^{12}$ is independently H, OH, alkyl, substituted alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, $ONO2$, $NO_2$, $N_3$, $NH_2$, aminoalkyl, aminoacid, aminoacyl, $ONH_2$, O-aminoalkyl, O-aminoacid, or O-aminoacyl, heterocycloalkyl, heterocycloalkaryl, aminoalkylamino, polyalklylamino, substituted silyl; $R^9$ is O, S, CH2, S=O, CHF, or $CF_2$, and B is a nucleosidic base. Sugar-modified nucleotides include, but are not limited to: 2'-fluoro modified ribonucleotides, 2'-OMe modified ribonucleotides, 2'-deoxy ribonucleotides, 2'-amino modified ribonucleotides and 2'-thio modified ribonucleotides. The sugar-modified nucleotide can be, for example, 2'-fluoro-cytidine, 2-fluoro-uridine, 2'-fluoro-adenosine, $2^1$-fluoro-guanosine, 2'-amino-cytidine, 2'-amino-uridine, 2'-amino-adenosine, 2'-amino-guanosine or 2'-amino-butyryl-pyrene~uridine. In one embodiment, the sugar-modified nucleotide is a 2-fluoro ribonucleotide. In some embodiments, when a 2'-deoxy ribonucleotide is present, it is upstream of the cleavage site referencing the antisense strand or downstream of the cleavage site referencing the antisense strand. The 2'-fluoro ribonucleotides can be in the sense and antisense strands. In some embodiments, the 2'-fluoro ribonucleotides are every uridine and cytidine. In other embodiments, the 2'-fluoro ribonucleotides are only present at the 3' and 5' ends of the sense strand, the antisense strand or both.

In another embodiment, the RNAi agent of the invention comprises one or more (e.g., about 1, 2, 3, 4, 5, 6, 7, 8, 9, 10, or more) nucleobase-modified nucleotides. Nucleobase-modified nucleotides useful in the invention include, but are not limited to: uridine and/or cytidine modified at the 5-position (e.g., 5-bromo-uridine, 5-(2-amino)propyl uridine, 5-amino-allyl-uridine, 5-iodo-uridine, 5-methyl-cytidine, 5-fluoro-cytidine, and 5-fluoro-uridine), ribo-thymidine, 2-aminopurine, 2,6-diaminopurine, 4-thiouridine, adenosine and/or guanosines modified at the 8 position (e.g., 8-bromo guanosine), deaza nucleotides (e.g., 7-deaza-adenosine), O- and N-alkylated nucleotides (e.g., N6-methyl adenosine) and non-nucleotide-type bases (e.g., deoxy-abasic, inosine, N3-methyluridine, N6, N6-dimethyl-adenosine, pseudouridine, purine ribonucleoside and ribavirin).

In another embodiment, the RNAi agent of the invention comprises one or more (e.g., about 1, 2, 3, 4, 5, 6, 7, 8, 9, 10, or more) backbone-modified nucleotides. For example, backbone modifications may include modifications represented by Formula III:

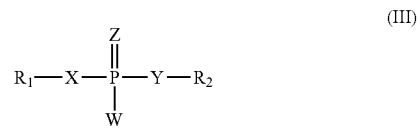

wherein each R1 and R2 is independently any nucleotide as described herein, each X and Y is independently O, S, N, alkyl, or substituted alkyl, each Z and W is independently O, S, N, alkyl, substituted alkyl, O-alkyl, S-alkyl, alkaryl, aralkyl, or acetyl. In some embodiments, W, X, Y, and Z are not all O. Exemplary backbone-modified nucleotides contain a phosphorothioate group or a phosphorodithioate. In another embodiment, a backbone modification of the invention comprises a phosphonoacetate and/or thiophosphonoacetate internucleotide linkage (see, e.g., Sheehan et al., 2003, *Nucleic Acids Res.,* 31, 4109-4118). The backbone-modifications can be within the sense strand, antisense strand, or both the sense and antisense strands. In some embodiments, only a portion of the internucleotide linkages are modified in one or both strands.

In other embodiments, all of the internucleotide linkages are modified in one or both strands. In one embodiment, the modified internucleotide linkages are at the 3' and 5' ends of one or both strands.

In another embodiment, the siRNA molecule of the invention may comprise one or more (e.g., about 1, 2, 3, 4, 5, 6, 7, 8, 9, 10, or more) crosslinks, e.g., a crosslink wherein the sense strand is crosslinked to the antisense strand of the siRNA duplex. Crosslinkers useful in the invention are those commonly known in the art, e.g., psoralen, mitomycin C, cisplatin, chloroethylnitrosoureas and the like. In one embodiment, the crosslink of the invention is a psoralen crosslink. The crosslink may be present downstream of the cleavage site referencing the antisense strand, and the crosslink may be present at the 5' end of the sense strand.

In another embodiment, the RNAi agent of the invention comprises a sequence wherein the antisense strand and target mRNA sequences comprise one or more (e.g., about 1, 2, 3, 4, 5, 6, 7, 8, 9, 10, or more) mismatches. In some embodiments, the mismatch is downstream of the cleavage site referencing the antisense strand, e.g., within 1-6 nucleotides from the 3' end of the antisense strand. In another embodiment, the nucleic acid molecule, e.g., RNAi agent, of the invention is an siRNA molecule that comprises a bulge, e.g., one or more (e.g., about 1, 2, 3, 4, 5, 6, 7, 8, 9, 10, or more) unpaired bases in the duplex siRNA. In some embodiments, the bulge is in the sense strand.

It is to be understood that any of the above combinations can be used in any combination to provide the modified RNAi agent of the present invention. For example, in some embodiments, the invention includes an siRNA, wherein the sense strand includes one or more (e.g., about 1, 2, 3, 4, 5, 6, 7, 8, 9, 10, or more) phosphorothioate internucleotide linkages, and/or one or more (e.g., about 1, 2, 3, 4, 5, 6, 7, 8, 9, 10 or more) 2'-deoxy, 2-O-methyl, and/or 2-fluoro sugar modifications, and/or one or more (e.g., about 1, 2, 3, 4, 5, 6, 7, 8, 9, 10 or more) base modified nucleotides, and/or an end-modification at the 3'-end, the 5'-end, or both the 3'- and 5'-ends of the sense strand.

In some embodiments, the invention includes an siRNA, wherein the antisense strand includes one or more (e.g., about 1, 2, 3, 4, 5, 6, 7, 8, 9, 10, or more) phosphorothioate internucleotide linkages, and/or one or more (e.g., about 1, 2, 3, 4, 5, 6, 7, 8, 9, 10 or more) 2'-deoxy, 2-O-methyl, and/or 2-fluoro sugar modifications, and/or one or more (e.g., about 1, 2, 3, 4, 5, 6, 7, 8, 9, 10 or more) base modified nucleotides, and/or an end-modification at the 3'-end, the 5'-end, or both the 3'- and 5'-ends of the antisense strand. In yet other embodiments, the invention includes an siRNA, wherein both the sense strand and the antisense strand include one or more (e.g., about 1, 2, 3, 4, 5, 6, 7, 8, 9, 10, or more) phosphorothioate internucleotide linkages, and/or one or more (e.g., about 1, 2, 3, 4, 5, 6, 7, 8, 9, 10 or more) 2'-deoxy, 2'-O-methyl, and/or 2'-fluoro sugar modifications, and/or one or more (e.g., about 1, 2, 3, 4, 5, 6, 7, 8, 9, 10 or more) base modified nucleotides, and/or an end-modification at the 3'-end, the 5'-end, or both the 3'- and 5'-ends of either or both the sense strand and/or the antisense strand.

Modified RNAi agents of the invention (i.e., duplex siRNA molecules) can be modified at the 5' end, 3' end, 5' and 3' end, and/or at internal residues, or any combination thereof. RNAi agent modifications can be, for example, end modifications, sugar modifications, nucleobase modifications, backbone modifications, and can contain mismatches, bulges, or crosslinks. Also included are 3' end, 5' end, or 3' and 5' and/or internal modifications, wherein the modifications are, for example, cross linkers, heterofunctional cross linkers and the like. RNAi agents of the invention also may be modified with chemical moieties (e.g., cholesterol) that improve the in vivo pharmacological properties of the RNAi agents.

In certain aspects of the present invention, the chemically modified siRNAs of the present invention are "terminally-modified siRNAs". That is, the siRNAs are modified at one or both of the 3' end and the 5' end of the sense and/or antisense strand. In certain embodiments, the chemically modified siRNAs are modified at both the 3' end and the 5' end of both the sense antisense strand. In some embodiments, the 3' end and/or the 5' end of the sense and/or antisense strands are end-modified such that 2 or 3 or 4 modified nucleotides are incorporated per end (e.g., within the 5-7 terminal nucleotides, e.g., within the duplex). In some embodiments, the 3' end and/or the 5' end of the sense and/or antisense strands are end-modified such that 2 or 3 or 4 2'-fluoro nucleotides, e.g., 2' fluorocytidine and/or 2' fluorouracil, are incorporated per end (e.g., within the 5-7 terminal nucleotides, e.g., within the duplex). In some embodiments, the 3' end and/or the 5' end of the sense and/or antisense strands are end-modified such that 2 or 3 or 4 internucleotide linkages are phosphorothioate linkages per end (e.g., between the 5-7 terminal nucleotides, e.g., within the duplex). In some embodiments, the modifications include any of the modifications described herein. In other embodiments, the modifications include phosphorothioate linkages. In still other embodiments, the modifications include 2'-sugar modifications. In still other embodiments, the modifications include 2'-fluoro nucleotide modifications. In yet other embodiments, the modifications include both phosphorothioate linkages and 2'-fluoro nucleotide modifications.

In various aspects, an agent for use in the method of the present invention is a polynucleotide, such as an antisense oligonucleotide or RNA molecule. In various aspects, the agent may be a polynucleotide, such as an antisense oligonucleotide or RNA molecule, such as anti-microRNA, microRNA mimic, dsRNA, siRNA, stRNA, and shRNA.

Polynucleotides of the present invention, such as antisense oligonucleotides and RNA molecules may be of any suitable length. For example, one of skill in the art would understand what length are suitable for antisense oligonucleotides or RNA molecule to be used to regulate gene expression. Such molecules are typically from about 5 to 100, 5 to 50, 5 to 45, 5 to 40, 5 to 35, 5 to 30, 5 to 25, 5 to 20, or 10 to 20 nucleotides in length. For example the molecule may be about 5, 10, 15, 16, 17, 18, 19, 20, 21, 22, 23, 24, 25, 26, 27, 28, 29, 30, 31, 32, 33, 34, 35, 40, 45 or 50 nucleotides in length. Such polynucleotides may include from at least about 15 to more than about 120 nucleotides, including at least about 16 nucleotides, at least about 17 nucleotides, at least about 18 nucleotides, at least about 19 nucleotides, at least about 20 nucleotides, at least about 21 nucleotides, at least about 22 nucleotides, at least about 23 nucleotides, at least about 24 nucleotides, at least about 25 nucleotides, at least about 26 nucleotides, at least about 27 nucleotides, at least about 28 nucleotides, at least about 29 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, at least about 100 nucleotides, at least about 110 nucleotides, at least about 120 nucleotides or greater than 120 nucleotides.

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. Depending on the use, however, a polynucleotide also can contain nucleotide analogs, including non-naturally occurring synthetic nucleotides or modified naturally occurring nucleotides. Nucleotide analogs are well known in the art and commercially available, as are polynucleotides containing such nucleotide analogs. The covalent bond linking the nucleotides of a polynucleotide generally is a phosphodiester bond. However, depending on the purpose for which the polynucleotide is to be used, the covalent bond also can be any of numerous other bonds, including a thiodiester bond, a phosphorothioate bond, a peptide-like bond or any other bond known to those in the art as useful for linking nucleotides to produce synthetic polynucleotides.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template.

As discussed above, in various embodiments antisense oligonucleotides or RNA molecules include oligonucleotides containing modifications. A variety of modification are known in the art and contemplated for use in the present invention. For example oligonucleotides containing modified backbones or non-natural internucleoside linkages are contemplated. As used herein, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

In various aspects modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Certain oligonucleotides having inverted polarity comprise a single 3' to 3' linkage at the 3'-most internucleotide linkage i.e., a single inverted nucleoside residue which may be abasic (the nucleobase is missing or has a hydroxyl group in place thereof). Various salts, mixed salts and free acid forms are also included.

In various aspects modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In various aspects, oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. In various aspects, oligonucleotides may include phosphorothioate backbones and oligonucleosides with heteroatom backbones. Modified oligonucleotides may also contain one or more substituted sugar moieties. In some embodiments oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_m CH_3$, $O(CH_2)_nOCH_3$, $O(CH_2)_nNH_2$, $O(CH_2)_nCH_3$, $O(CH_2)_nONH_2$ and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, N3, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Another modification includes 2'-methoxyethoxy ($2'OCH_2CH_2OCH_3$, also known as 2'-O-(2-methoxyethyl) or 2'-MOE).

In related aspects, the present invention includes use of Locked Nucleic Acids (LNAs) to generate antisense nucleic acids having enhanced affinity and specificity for the target polynucleotide. LNAs are nucleic acid in which the 2'-hydroxyl group is linked to the 3' or 4' carbon atom of the sugar ring thereby forming a bicyclic sugar moiety. The linkage is preferably a methelyne (—CH$_2$—), group bridging the 2' oxygen atom and the 4' carbon atom wherein n is 1 or 2.

Other modifications include 2'-methoxy(2'-O—CH$_3$), 2'-aminopropoxy(2'-OCH$_2$CH$_2$CH$_2$NH$_2$), 2'-allyl (2'-CH—CH—CH$_2$), 2'-O-allyl (2'-O—CH$_2$—CHCH$_2$), 2'-fluoro (2'-F), 2'-amino, 2'-thio, 2'-Omethyl, 2'-methoxymethyl, 2'-propyl, and the like. The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazi-n-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrimido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases are known in the art. Certain of these nucleobases are particularly useful for increasing the binding affinity of the oligomeric compounds described herein. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2 C and are presently preferred base substitutions, even more particularly when combined with 2'-O-methoxyethyl sugar modifications.

Another modification of the antisense oligonucleotides described herein involves chemically linking to the oligonucleotide one or more moieties or conjugates which enhance the activity, cellular distribution or cellular uptake of the oligonucleotide. The antisense oligonucleotides can include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Conjugate moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., dihexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylaminocarbonyloxycholesterol moiety.

In other aspects, RNA silencing agents may be modified according to methods described in the art (Amarzguioui et. al., *Nucleic Acids. Res.*, (2003) 31: 589-95; Chiu and Rana, *RNA* (2003), 9: 1034-48; Chiu and Rana, *Mol. Cell* (2002), 10: 549-61); Morrissey et al., *Nature Biotechnol.* (2005), 23: 2002-7), each of which is incorporated by reference herein. In one embodiment, RNA silencing agent may be conjugated to cholesterol (see, e.g., Soutschek, et al., *Nature* (2004), 432: 173-8).

In some embodiments, the RNAi agent of the instant invention may also contain a nuclear localization/nuclear targeting signal(s). Such modifications may be made exclusive of, or in addition to, any combination of other modifications as described herein. Nuclear targeting signals include any art-recognized signal capable of effecting a nuclear localization to a molecule, including, for example, NLS signal sequence peptides.

Oligonucleotide RNAi agents may be produced enzymatically or by partial/total organic synthesis. In one embodiment, an RNAi agent, e.g., siRNA, is prepared chemically. Methods of synthesizing RNA and DNA molecules are known in the art, in particular, the chemical synthesis methods as described in Verma and Eckstein (1998) *Annul Rev. Biochem.* 67:99-134. RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the RNA molecules, e.g., RNAi oligonucleotides, can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) *Methods Enzymol* 180:51-62). The RNA may be dried for storage or dissolved in an aqueous solution. The solution may contain buffers or salts to inhibit annealing, and/or promote stabilization of the single strands.

In one embodiment, siRNAs are synthesized either in vivo, in situ, or in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the siRNA. Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses siRNA from a recombinant construct may be produced by introducing the construct into a zygote, an embryonic stem cell, or another multipotent cell derived from the appropriate organism.

Expression levels of target and any other surveyed RNAs and proteins may be assessed by any of a wide variety of well-known methods for detecting expression of non-transcribed nucleic acid, and transcribed nucleic acid or protein. Non-limiting examples of such methods include RT-PCR of RNA followed by size separation of PCR products, nucleic acid hybridization methods, e.g., northern blots and/or use of nucleic acid arrays; nucleic acid amplification methods; immunological methods for detection of proteins; protein purification methods; and protein function or activity assays.

RNA expression levels can be assessed by preparing mRNA/cDNA (I.e., a transcribed polynucleotide) from a cell, tissue or organism, and by hybridizing the mRNA/cDNA with a reference polynucleotide which is a complement of the assayed nucleic acid, or a fragment thereof. cDNA can, optionally, be amplified using any of a variety of polymerase chain reaction or in vitro transcription methods prior to hybridization with the complementary polynucleotide, it may be not amplified. Expression of one or more transcripts can also be detected using quantitative PCR to assess the level of expression of the transcript(s).

In other embodiments, a nucleic acid molecule employed in a delivery complex of the invention is a nucleic acid molecule other than an RNA silencing agent. In certain embodiments, the nucleic acid molecules may comprise any of the chemical modifications discussed supra.

In one embodiment, a nucleic acid molecule employed in the invention is an antisense nucleic acid molecule that is complementary to a target mRNA or to a portion of the mRNA, or a recombinant expression vector encoding the antisense nucleic acid molecule. Antisense nucleic acid molecules are generally single-stranded DNA, RNA, or DNA/RNA molecules which may comprise one or more nucleotide analogs. The use of antisense nucleic acids to downregulate the expression of a particular protein in a cell is well known in the art (see e.g., Weintraub, H. et al, Antisense RNA as a molecular tool for genetic analysis, *Reviews—Trends in Genetics*, Vol. 1(1) 1986; Askari, F. K. and McDonnell, W. M. (1996) *N. Eng. J. Med* 334:316-318; Bennett, M. R. and Schwartz, S. M. (1995) *Circulation* 92:1981-1993; Mercola, D. and Cohen, J. S. (1995) *Cancer Gene Ther.* 2:47-59; Rossi, J. J. (1995) *Br. Med Bull.* 51:217-225; Wagner, R. W. (1994) *Nature* 372:333-335). An antisense nucleic acid molecule comprises a nucleotide sequence that is complementary to the target mRNA sequence and accordingly is capable of hydrogen bonding to the mRNA. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). An antisense nucleic acid may be designed so as to be complementary to a region preceding or spanning the initiation codon in the 3' untranslated region of an mRNA.

Given the known nucleotide sequence of a target mRNA, antisense nucleic acids of the invention can be designed according to the rules of Watson and Crick base pairing. The antisense nucleic acid molecule can be complementary to the entire coding region of an mRNA, but may be antisense to only a portion of the coding or noncoding region of an mRNA. For example, the antisense oligonucleotide can be complementary to the region surrounding the translation start site of a target mRNA. An antisense oligonucleotide can be, for example, about 5, 10, 15, 20, 25, 30, 35, 40, 45, 50, 60, 70, 80, 100, 500, 1000 nucleotides or more in length. In some embodiments, the antisense oligonucleotide may be as long as, or longer than, the length of the mRNA that is targeted.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylino sine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. To inhibit expression in cells, one or more antisense oligonucleotides can be used.

Alternatively, an antisense nucleic acid can be produced biologically using an expression vector into which all or a portion of a cDNA has been subcloned in an antisense orientation (i.e., nucleic acid transcribed from the inserted nucleic acid will be of an antisense orientation to a target nucleic acid of interest). Regulatory sequences operatively linked to a nucleic acid cloned in the antisense orientation can be chosen which direct the expression of the antisense RNA molecule in a cell of interest, for instance promoters and/or enhancers or other regulatory sequences can be chosen which direct constitutive, tissue specific or inducible expression of antisense RNA. The antisense expression vector is prepared according to standard recombinant DNA methods for constructing recombinant expression vectors, except that the cDNA (or portion thereof) is cloned into the vector in the antisense orientation. The antisense expression vector can be in the form of, for example, a recombinant plasmid, phagemid or attenuated virus. The antisense expression vector can be introduced into cells using a standard transfection technique.

The antisense nucleic acid molecules of the invention are typically administered to a subject or generated in situ such that they hybridize with or bind to cellular mRNA and/or genomic DNA encoding a protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of antisense molecules, vector constructs in which the antisense nucleic acid molecule is placed under the control of a strong pol H or pol IE promoter.

In one particular embodiment, antisense oligonucleotides may be employed which are complementary to one or more of the RNA silencing agents (e.g., miRNA molecules) described supra. The anti-miRNA oligonucleotides may be DNA or RNA oligonucleotides, or they may be comprised of both ribonucleotide and deoxyribonucleotides or analogs thereof. In certain embodiments, the anti-miRNA oligonucleotides comprise one or more (e.g., substantially all) 2' O-methyl ribonucleotides. Such molecules are potent and irreversible inhibitors of miRNA-mediated silencing and are therefore useful for modulating RNA silencing both in vitro and in vivo. In vivo methodologies are useful for both general RNA silencing modulatory purposes as well as in therapeutic applications in which RNA silencing modulation (e.g., inhibition) is desirable. For example, insulin secretion has y been shown to be regulated by at least one miRNA (Poy et al. 2004), and a role for miRNAs has also been implicated in spinal muscular atrophy (SMA; Mourelatos et al. 2002).

In yet another embodiment, a nucleic acid molecule employed in the invention is an a-anomeric nucleic acid molecule. An a-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). Such a nucleic acid molecule can also comprise a 2'-O-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an nucleic acid molecule employed in the invention is a ribozyme. Ribozymes are catalytic RNA molecules having extensive secondary structure and which intrinsically capable of cleaving a single-stranded nucleic acid, such as an mRNA, to which they have a complementary region. Thus, ribozymes (e.g., hammerhead ribozymes (described in Haseihoffand Gerlach (1988) *Nature* 334:585-591)) can be used to catalytically cleave mRNA transcripts to thereby inhibit translation mRNAs. A ribozyme having specificity e.g., for a RCK (or a RCK ortholog or RCK interactor)-encoding nucleic acid can be designed based upon the nucleotide sequence of the cDNA. For example, a derivative of a Tetrahymena L-19 IVS RNA can be constructed in which the nucleotide sequence of the active site is complementary to the nucleotide sequence to be cleaved in a target mRNA. See, e.g., Cech et al. U.S. Pat. No. 4,987,071 and Cech et al. U.S. Pat. No. 5,116,742. Alternatively, a target mRNA can be used to select a catalytic RNA having a specific ribonuclease activity from a pool of RNA molecules. See, e.g., Bartel, D. and Szostak, J. W. (1993) *Science* 261:1411-1418.

Alternatively, gene expression can be inhibited by targeting nucleotide sequences complementary to the regulatory region of a target gene to form triple helical structures that prevent transcription of a gene in target cells. See generally, Helene, C. (1991) *Anticancer Drug Des.* 6(6):569-84; Helene, C. et al. (1992) *Ann. N.Y. Acad Sc.* 660:27-36; and Maher, L J. (1992) *Bioassays* 14(12):807-15.

In other embodiments, a nucleic acid molecule of the invention is a vector, e.g., an expression vector containing a nucleic acid encoding a gene product (or portion thereof) or RNA silencing agent. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, adeno-associated viruses, retroviral vectors, and lentiviruses), which serve equivalent functions.

In certain aspects, a vector of the invention encodes an RNA silencing agent described supra, e.g., small hairpin RNAs (shRNAs). Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides. Brummelkamp et al. (2002), *Science*, 296, 550-553; Lee et al. (2002) supra; Miyagishi and Taira (2002), *Nature Biotechnol.*, 20, 497-500; Paddison et al. (2002), supra; Paul (2002), supra; Sui (2002) supra; Yu et al. (2002), supra. Such expression constructs may include one or more inducible promoters, RNA Pol mI promoter systems such as U6 snRNA promoters or HI RNA polymerase III promoters, or other promoters known in the art. The constructs can include one or both strands of the RNA silencing agent. Expression constructs expressing both strands can also include loop structures linking both strands, or each strand can be separately transcribed from separate promoters within the same construct. Each strand can also be transcribed from a separate expression construct, Tuschl (2002), supra.

In one aspect, the present invention provides for the delivery of pharmaceutical agents via a nanotransporter to the desired target, e.g., a cell, or tissue.

The term "pharmaceutical agent," as used herein, refers to compounds having pharmaceutical activity. Examples of pharmaceutical agents for use with the nanotransporters of the present invention include, but are not limited to polynucleotides, proteins, polypeptides, peptides, chemotherapeutic agents, antibiotics, etc.

In certain embodiments, a pharmaceutical agent employed in a delivery complex of the invention is antibody. The term "antibody" as used herein refers to immunoglobulin molecules and immunologically active portions of immunoglobulin molecules, i.e., molecules that contain an antigen binding site which specifically binds (immunoreacts with) an antigen. Examples of immunologically active portions of immunoglobulin molecules include F(ab) and F(ab')2 fragments which can be generated by treating the antibody with an enzyme such as pepsin. Either polyclonal or monoclonal antibodies that bind target antigen may be employed in the methods of the invention.

The term "monoclonal antibody" or "monoclonal antibody composition", as used herein, refers to a population of antibody molecules that contain only one species of an antigen binding site capable of immunoreacting with a particular epitope of target antigen. A monoclonal antibody composition thus typically displays a single binding affinity for a particular target antigen with which it immunoreacts.

Polyclonal antibodies can be prepared by immunizing a suitable subject with a target antigen or immunogen, respectively. The antibody titer in the immunized subject can be monitored over time by standard techniques, such as with an enzyme linked immunosorbent assay (ELISA) using immobilized target antigen. If desired, the antibody molecules can be isolated from the mammal (e.g., from the blood) and further purified by well-known techniques, such as protein A chromatography to obtain the IgO fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256: 495-497) (see also, Brown et al. (1981) *J. Immunol.* 21:S39-A6; Brown et al. (1980) *J. Biol. Chem.* 255:4980-83; Yeh et al. (1976) *PNAS* 76:2927-31; and Yeh et al. (1982) *Int. J. Cancer* 29:269-75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77-96) or trioma techniques.

The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) Yale *J. Biol Med*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a target antigen, and the culture supernatants of the resulting hybridoma cells are screened to identify a hybridoma producing a monoclonal antibody that binds target antigen.

Any of the many well-known protocols used for fusing lymphocytes and immortalized cell lines can be applied for the purpose of generating a monoclonal antibody (see, e.g., G. Galfre et al. (1977) *Nature* 266:55052; Gefter et al. *Somatic Cell Genet.*, cited supra; Lerner, Yale *J. Biol. Med.*, cited supra; Kenneth, *Monoclonal Antibodies*, cited supra). Moreover, the ordinarily skilled worker will appreciate that there are many variations of such methods which also would be useful.

Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/0-Ag 14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind target antigen, e.g., using a standard ELISA assay.

Alternative to preparing monoclonal antibody-secreting hybridomas, a monoclonal antibody can be identified and isolated by screening a recombinant combinatorial immunoglobulin library (e.g., an antibody phage display library) with target antigen to thereby isolate immunoglobulin library members that bind target antigen, respectively. Kits for generating and screening phage display libraries are commercially available (e.g., the Pharmacia Recombinant Phage Antibody System, Catalog No. 27-9400-01; and the Stratagene SurjfZP™ Phage Display Kit, Catalog No. 240612). Additionally, examples of methods and reagents particularly amenable for use in generating and screening antibody display library can be found in, for example, Ladner et al. U.S. Pat. No. 5,223,409; Rang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod Hybridomas* 3:81-85; Huse et al. (1989) *Science* 246:1275-1281; Griffiths et al. (1993) *EMBO J* 12:725-734; Hawkins et al. (1992) *J. Mol. Biol.* 226:889-896; Clarkson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc. Acid Res.* 19:4133-4137; Barbas et al. (1991) *PNAS* 88:7978-7982; and McCafferty et al. *Nature* (1990) 348:552-554.

In certain embodiments, a pharmaceutical agent employed in a delivery complex of the invention is a drug moiety. The term "drug moiety" as used herein refers to small molecules or active portions thereof which have art-recognized therapeutic properties. Exemplary drug moieties include anti-inflammatory, anticancer, anti-infective (e.g., anti-fungal, antibacterial, anti-parasitic, anti-viral, etc.), and anesthetic therapeutic agents.

In one exemplary embodiment, the drug moiety is an anti-cancer agent. Exemplary anti-cancer agents include, but are not limited to, cytostatics, enzyme inhibitors, gene regulators, cytotoxic nucleosides, tubulin binding agents, hormones and hormone antagonists, anti-angiogenesis agents, and the like. Exemplary cytostatic anti-cancer agents include alkylating agents such as the anthracycline family of drugs (e.g., adriamycin, cyclosporin-A, chloroquine), DNA synthesis inhibitors (e.g., methotrexate, 5-fluorouracil, ganciclovir), DNA-intercalators or cross-linkers (e.g., bleomycin, carboplatin, cyclophosphamide, cisplatin), DNA-RNA transcription regulators (e.g., actinomycin D). Exemplary cytotoxic nucleoside anti-cancer agents include, for example, adenosine arabinoside, cytarabine, cytosine arabinoside, 5-fluorouracil, fludarabine, floxuridine, florafur, and 6-mercaptopurine.

Exemplary anti-cancer tubulin binding agents include taxoids (e.g., paclitaxel, docetaxel, taxane). Exemplary anti-cancer hormones and hormone antagonists, include corticosteroids (e.g., prednisone), progestins (e.g., hydroxyprogesterone or medroprogesterone), estrogens (e.g., diethylstilbestrol), antiestrogens (e.g., tamoxifen), androgens (e.g., testosterone), aromatase inhibitors (e.g., aminogluthetimide), 17-(allylamino)-17-demethoxygeldanamycin, 4-amino-1,8-naphthalimide, apigenin, brefeldin A, cimetidine, dichloromethylene-diphosphonic acid, leuprolide (leuprorelin), luteinizing hormone-releasing hormone, pifithrin-a, rapamycin, sex hormone-binding globulin, and thapsigargin.

As an alternative or in addition to the pharmaceutical agents described above, the delivery complexes of the invention may comprise therapeutic peptides (e.g., insulin), biological response modifiers, enzymes, or fragments thereof. Exemplary biological response modifiers include hormones, cytokines, chemokines, growth factors, and clotting factors. In fact delivery complexes may comprise any compound or composition, which, when present in an effective amount, reacts with and/or affects a tissue, living cell, and/or organism or traverses a biological space, e.g., a blood brain barrier, such that the therapeutic agent or pay load can have its mode of action. It is understood that depending on the nature of the active substance, the active substance can either be active in a biological space, at the cell surface, in the cell, or have its activity, such as with DNA, RNA, protein, or peptide after being introduced into the cell.

Examples of biologically active substances include, but are not limited to, nucleic acids such as DNA, cDNA, RNA (full length mRNA, ribozymes, antisense RNA, RNAi siRNA, miRNA, decoys), oligodeoxynucleotides (phosphodiesters, phosphothioates, phosphoramidites, and all other chemical modifications), oligonucleotide (phosphodiesters, etc.) or linear and closed circular plasmid DNA; carbohydrates, proteins and peptides (e.g., peptides for cellular delivery and transport, peptide for specific receptors, peptides that can cross the blood brain barrier, including recombinant proteins such as for example cytokines (e.g., NGF, G-CSF, GM-CSF), enzymes, vaccines (e.g., HBsAg, gp120); vitamins, prostaglandins, drugs such as local anesthetics (e.g., procaine), antimalarial agents (e.g., chloroquine), compounds which need to cross the blood-brain barrier such as anti-parkinson agents (e.g., leva-DOPA), adrenergic receptor antagonists (e.g., propanolol), anti-neoplastic agents (e.g., doxorubicin), antihistamines, biogenic amines (e.g., dopamine), antidepressants (e.g., desipramine), anticholinergics (e.g., atropine), antiarrhythmics (e.g., quinidine), antiemetics (e.g., chloroprimamine) and analgesics (e.g., codeine, morphine) or small molecular weight drugs such as cisplatin which enhance transfection activity, or prolong the life time of DNA in and outside the cells. In one exemplary embodiment, the delivery complex includes Amantadine.

Nucleic acid molecules, e.g., RNA silencing agents (e.g., novel chemically-modified RNA Silencing agents of the invention), can be associated with (i.e., operably linked to) a nanotransporter by any techniques and/or approaches known in the art, described herein, and/or as can be developed by one of skill in the art. In some embodiments, the association may involve covalent bonds, dipole interactions, electrostatic forces, hydrogen bonds, ionic bonds, van der Waals forces, and/or other bonds that can conjugate the nucleic acid to the nanotransporter.

In one embodiment, the nucleic acid molecule, e.g., an RNA silencing agent, e.g., an siRNA, is conjugated to the core of the nanotransporter, for example via a linker. A "linking moiety" as used herein refers to any moiety capable of linking a nucleic acid molecule, e.g., siRNA, to a nanotransporter. Any linking moiety known in the art may be used in the present invention. A linking moiety useful in this invention may comprise any bi-functional compound, for example a bifunctional maleimide compound, e.g., sulfosuccinimidyl-4-(p-maleimidophenyl)-butyrate.

The nucleic acid molecule may be associated or conjugated to the nanotransporter by generally known methods. In one embodiment, the nucleic acid molecule is associated with the nanotransporter by mixing the nucleic acid molecule with the nanotransporter. In another embodiment, the nucleic acid molecule is covalently bonded to the nanotransporter.

In some embodiments, the nucleic acid molecule is associated with the core via ionic bonds. In exemplary embodiments, the core of the nanotransporter is a low molecular weight polylysine dendrimer, to which dioleolyl can be also attached. In one embodiment, this complex is formed by mixing the DiOleoyl-LDG3 with siRNA. In another embodiment, the siRNA is covalently conjugated to the DiOleoyl-LDG3 complex via the amino groups on the LDG3 branches.

The core of the nanotransporter may be any molecule capable of association with a nucleic acid molecule, e.g., siRNA, and at least one functional surface group, for example the core may be DiOleoyl LDG3. In an exemplary embodiment, the core of the nanotransporter is a nanotube. Nanotube-siRNA conjugates can be formed in a similar manner as the methods described above.

In yet another embodiment, the nanotransporter of the invention is HBOLD. Without wishing to be bound by any particular theory, it is believed that the nanotransporters of the invention, e.g., HBOLD, are non-toxic to cells.

The HBOLD constructs have also been found to be as effective as standard transfection agents in the delivery of RNA silencing agents to target cells. In particular, the HBOLD constructs had a similar effectiveness as standard transfection agents in silencing expression of Apo B in hepatocytes.

In certain aspects, the present invention provides for the delivery of pharmaceutical agents via a nanotransporter of the invention to a desired target, e.g., a cell, or tissue. The term "pharmaceutical agent," as used herein, refers to compounds (e.g., compounds other than the nucleic acid molecules identified supra) having pharmaceutical activity. Examples of pharmaceutical agents for use with the nanotransporters of the present invention include, but are not limited to polynucleotides, proteins, polypeptides, peptides, chemotherapeutic agents, antibiotics, etc.

Pharmaceutical agents can be conjugated to the nanotransporter by any techniques and/or approaches known in the art, described herein, and/or as can be developed by one of skill in the art. In some embodiments, the association may involve covalent bonds, dipole interactions, electrostatic forces, hydrogen bonds, ionic bonds, van der Waals forces, and/or other bonds that can conjugate the pharmaceutical agent to the nanotransporter.

In one embodiment, the target mRNA of the invention specifies the amino acid sequence of a cellular protein (e.g., a nuclear, cytoplasmic, transmembrane, or membrane-associated protein). In another embodiment, the target mRNA of the invention specifies the amino acid sequence of an extracellular protein (e.g., an extracellular matrix protein or secreted protein). As used herein, the phrase "specifies the amino acid sequence" of a protein means that the mRNA sequence is translated into the amino acid sequence according to the rules of the genetic code. The following classes of proteins are listed for illustrative purposes: developmental proteins (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene-encoded proteins (e.g., ABLI, BCLI, BCL2, BCL6, CBFA2, CBL, CSFIR, ERBA, ERBB, EBRB2, ETSI, ETSI, ETV6, FOR, FOS, FYN, HCR, HRAS, JUN, KRAS, LCK, LYN, MDM2, MLL, MYB, MYC, MYCLI, MYCN, NRAS, PIM I, PML, RET, SRC, TALI, TCL3, and YES); tumor suppressor proteins (e.g., APC, BRCA1, BRCA2, MADH4, MCC, NF I, NF2, RB I, TP53, and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextriinases, DNA and RNA polymerases, galactosidases, glucanases, glucose oxidases, granule-bound starch synthases, OTPases, helicases, hernicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases).

In a one aspect of the invention, the target mRNA molecule of the invention specifies the amino acid sequence of a protein associated with a pathological condition. For example, the protein may be a pathogen-associated protein (e.g., a viral protein involved in immunosuppression of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen. Alternatively, the protein may be a tumor-associated protein or an autoimmune disease-associated protein.

In one embodiment, the target mRNA molecule of the invention specifies the amino acid sequence of an endogenous protein (i.e., a protein present in the genome of a cell or organism). In another embodiment, the target mRNA molecule of the invention specified the amino acid sequence of a heterologous protein expressed hi a recombinant cell or a genetically altered organism. In another embodiment, the target mRNA molecule of the invention specified the amino acid sequence of a protein encoded by a transgene (i.e., a gene construct inserted at an ectopic site in the genome of the cell). In yet another embodiment, the target mRNA molecule of the invention specifies the amino acid sequence of a protein encoded by a pathogen genome which is capable of infecting a cell or an organism from which the cell is derived.

By inhibiting the expression of such proteins, valuable information regarding the function of the proteins and therapeutic benefits which may be obtained from the inhibition may be obtained.

The nanotransporter, e.g., the HBOLD nanotransporter, of the invention may be used to target specific genes of interest, that is, genes associated with metabolic disorders including high cholesterol levels, obesity, and diabetes. In one embodiment, the HBOLD nanotransporter is associated with gene-specific siRNA molecule and is used to knock down or silence target genes associated with cholesterol production, including, but not limited to, apolipoprotein B (ApoB). ApoB is the main apolipoprotein of chylomicrons and low density lipoproteins (LDL). ApoB is found in the plasma in two main isoforms, apoB-48 and apoB-100, synthesized by the gut and the liver, respectively.

The intestinal (apoB-48) and hepatic (apoB-100) forms of apoB are coded by a single gene and by a single mRNA transcript. The nucleotide and amino acid sequence of human ApoB can be found in GenBank record 014502152, the entire contents of which are incorporated by reference herein. Nanotransporter s of the invention may be conjugated to siRNA corresponding to the RNA sequence of the apoB gene, including apoB-100, apoB-48, or both apoB-100 and apoB-48.

The apoB1OO mature peptide is encoded by nucleotides 210-13817 of the above-mentioned sequence, and the apoB-48 mature peptide is encoded by nucleotides 210-6665 of the above-mentioned sequence.

Silencing of the apoB gene may also be used to treat metabolic disorders associated with aberrant glucose transport (e.g., diabetes), obesity, increasing metabolism (e.g., fatty acid metabolism), and increasing brown fat. ApoB protein is a candidate target gene siRNA therapy for lipid-based diseases.

In another embodiment, the nanotransporter is associated with gene-specific siRNA and is used to treat metabolic disorders associated with aberrant glucose transport (e.g., diabetes) and obesity by knocking down or silencing nuclear receptor interacting protein 140 (RTP140 or NRJP1 for Nuclear Receptor-interacting Protein 1).

RTP 140 is a corepressor which can inhibit the transcriptional activity of a number of nuclear receptors. RIP 140 is a nuclear protein containing approximately 1158 amino acids, with a size of approximately 128 kDa. RIP140 binds to nuclear receptors via LXXLL motifs, wherein L is leucine and X is any amino acid (Heery et al., *Nature*, 387(6634): 733-6, 1997). Ten LXXLL motifs are found in the RTP140 sequence. RTP140 also interacts with histone deacetylases and with C-terminal binding protein (CTBP) via a PXDLS motif found in the RIP 140 sequence. The nucleotide and amino acid sequence of human RIP140 can be found in GenBank record GI 57232745, the entire contents of which are incorporated by reference herein. Nanotransporters of the invention may be conjugated to siRNA molecules which target the RNA sequence of REP 140.

The RTP140 mature peptide is encoded by nucleotides 335-381 of the above-mentioned sequence, and the apoB-48 mature peptide is encoded by nucleotides 210-6665 of the above-mentioned sequence.

Examples of other genes associated with metabolic diseases and disorders include, genes for dyslipidemia (e.g., liver X receptors (e.g., LXRcc and LXRp (Genback Accession No. NM.sub.-007121)), farnesoid X receptors (FXR) (Genbank Accession No. NM.sub.~005123), sterol-regulatory element binding protein (SREBP), Site-1 protease (SIP), 3-hydroxy-3-methylglutary-1 coenzyme-A reductase (HMG coenzyme-A reductase), Apolipoprotein (ApoB), and Apolipoprotein (ApoE)) and gene associated with diabetes (e.g., Glucose 6-phosphatase) (see, e.g., Forman et al., *Cell* 81:687 (1995); Seol et al., *Mol. Endocrinol.* 9:72 (1995), Zavacki et al., *PNAS USA* 94:7909 (1997); Sakai et al., *Cell* 85:1037-1046 (1996); Duncan et al., *J. Biol. Chem.* 272: 12778-12785 (1997); Willy et al., *Genes Dev.* 9(9):1033-45 (1995); Lehmann et al., *J. Biol. Chem.* 272(6):3137-3140 (1997); Janowski et al., *Nature* 383:728-731 (1996); Pet et al., *Cell* 93:693-704(1998)).

The present invention provides for both prophylactic and therapeutic methods of treating a subject at risk of (or susceptible to) a disorder or having a disorder associated with aberrant or unwanted target gene expression or activity. "Treatment", or "treating" as used herein, is defined as the application or administration of a therapeutic agent (e.g., nucleic acid molecule, and/or a pharmaceutical agent) to a patient, or application or administration of a therapeutic agent to an isolated tissue or cell line from a patient, who has a disease or disorder, a symptom of disease or disorder or a predisposition toward a disease or disorder, with the purpose to cure, heal, alleviate, delay, relieve, alter, remedy, ameliorate, improve or affect the disease or disorder, the symptoms of the disease or disorder, or the predisposition toward disease.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with the nucleic acid molecules and/or pharmaceutical agents of the present invention or target nucleic acid molecules and/or pharmaceutical agents according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one embodiment, the invention provides methods for preventing in a subject, a disease or condition associated with an aberrant or unwanted target gene expression or activity, by administering to the subject a therapeutic agent (e.g., a nucleic acid molecule, and/or a pharmaceutical agent). Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject. The appropriate agent can be determined based on screening assays described herein.

Another aspect of the invention pertains to methods of modulating target gene expression, protein expression or activity for therapeutic purposes. Accordingly, in an exemplary embodiment, the modulatory method of the invention involves contacting a cell capable of expressing the target gene with a therapeutic agent (e.g., a nucleic acid molecule and/or pharmaceutical agent) that is specific for the target gene or protein (e.g., is specific for the mRNA encoded by the gene or specifying the amino acid sequence of the protein) such that expression or one or more of the activities of target protein is modulated. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

The therapeutic agents (e.g., nucleic acid molecules and/or pharmaceutical agents) of the invention can be administered to individuals to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physol.* 23(10-11): 983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofiirans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/HI drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a target gene polypeptide of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a therapeutic agent of the present invention can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a therapeutic agent, as described herein.

Therapeutic agents can be tested in an appropriate animal model. For example, an siRNA (or expression vector or transgene encoding same) as described herein can be used in an animal model to determine the efficacy, toxicity, or side effects of treatment with the agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

In certain aspects, the invention provides an improved method of treating diseases by providing a more effective means by which to deliver agents (e.g., RNA silencing agents) for treatment of such diseases. For example, the invention provides delivery complexes including an RNA silencing agent to treat a disorder by targeting relevant disease-associated target genes (e.g., a gain-of-function disorder target genes), such that expression of the target gene is silenced. The compositions of the invention can act as novel therapeutic agents for controlling one or more of neurologic disorders, cellular proliferative and/or differentiative disorders, disorders associated with bone metabolism, immune disorders, hematopoietic disorders, cardiovascular disorders, liver disorders, viral diseases, pain or metabolic disorders.

The delivery complexes of the invention are surprisingly effective when administered in low doses to a subject (e.g., a mammal, e.g., a human). In particular, the delivery complexes of the invention require only small amounts of RNA silencing agent in order to silence disease-related genes (e.g., endogenous disease-related genes) in a clinically acceptable and therapeutically affordable manner. In certain embodiments, delivery complexes are administered at a dose which provides an effective dose of about 1 to about 50 mg/kg of RNA silencing agent to the subject. In other embodiments, the delivery complexes are administered at an effective dose that provides an effective dose of about 1 to about 10 mg/kg of RNA silencing agent to the subject. In further embodiments, the delivery complexes are administered at an effective dose that provides about 1 to about 5 mg/kg of RNA silencing agent to the subject (e.g., 5 mg/kg, 4 mg/kg. 3 mg/kg, 2.5 mg/kg. 1.25 mg/kg, 1 mg/kg, or less).

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer," "hyperproliferative," and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair. The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoictic neoplastic disorders" includes diseases involving hyperplastic/neoplastic cells of hematopoietic origin, e.g., arising from myeloid, lymphoid or erythroid lineages, or precursor cells thereof. The diseases may arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in OncolHemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

In general, the compositions of the invention are designed to target genes associated with particular proliferative disorders. Examples of such genes associated with proliferative disorders that can be targeted include activated ras, p53, BRCA-1, and BRCA-2.

Other specific genes that can be targeted are those associated with amyotrophic lateral sclerosis (ALS; e.g., superoxide dismutase-1 (SOD1)); Huntington's disease (e.g., huntingtin), Parkinson's disease (parkin), and genes associated with autosomal dominant disorders.

In certain embodiments, the neurological disorder is a polyglutamine disorder. The term "polyglutamine disorder" as used herein, refers to any disease or disorder characterized by an expanded of a $(CAG)_n$ repeats at the 5' end of the coding region (thus encoding an expanded polyglutamine region in the encoded protein). In one embodiment, polyglutamine disorders are characterized by a progressive degeneration of nerve cells. Examples of polyglutamine disorders include but are not limited to: Huntington's disease, spino-cerebellar ataxia type 1, spino-cerebellar ataxia type 2, spino-cerebellar ataxia type 3 (also known as Machado-Joseph disease), and spino-cerebellar ataxia type 6, spino-cerebellar ataxia type 7 and dentatoiubral-pallidoluysian atrophy.

The compositions of the invention can be used to treat a variety of immune disorders, in particular those associated with overexpression of a gene or expression of a mutant gene. Examples of hematopoietic disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure, coronary artery disease, valvular disease, arrhythmias, and cardiomyopathies.

Disorders which may be treated by methods described herein include, but are not limited to, disorders associated with an accumulation in the liver of fibrous tissue, such as that resulting from an imbalance between production and degradation of the extracellular matrix accompanied by the collapse and condensation of preexisting fibers.

Additionally, molecules of the invention can be used to treat viral diseases, including but not limited to hepatitis B, hepatitis C, herpes simplex virus (HSV), HIV-AEDS, poliovirus, and smallpox virus. Molecules of the invention are engineered as described herein to target expressed sequences of a virus, thus ameliorating viral activity and replication. The molecules can be used in the treatment and/or diagnosis of viral infected tissue. Also, such molecules can be used in the treatment of virus-associated carcinoma, such as hepatocellular cancer.

Metabolic disorders affect how the body processes substances needed to carry out physiological functions. A number of metabolic disorders share certain characteristics, i.e., they are associated the insulin resistance, lack of ability to regulate blood sugar, weight gain, and increase in body mass index. Examples of metabolic disorders include diabetes and obesity, as well as increased serum cholesterol levels. Examples of diabetes include type 1 diabetes mellitus, type 2 diabetes mellitus, diabetic neuropathy, peripheral neuropathy, diabetic retinopathy, diabetic ulcerations, retinopathy ulcerations, diabetic macrovasculopathy, and obesity. Identification or selection of a subject in need of treatment can be accomplished by any skilled medical practitioner or researcher using art-recognized diagnostic skills or techniques.

In one embodiment, the invention includes a method of decreasing cholesterol levels by silencing a target gene associated with increased cholesterol, wherein the nanotransporter of the invention is conjugated to a RNA silencing agent (e.g., an siRNA) to form a delivery complex capable of efficiently targeting the target gene. In one embodiment the target gene is apoB. ApoB-100 participates in the transport and delivery of endogenous plasma cholesterol (Davidson and Shelness, *Annu. Rev. Nutr.,* 2000, 20, 169-193). Elevated plasma levels of the ApoB-100-containing lipoprotein Lp(a) are associated with increased risk for atherosclerosis and its manifestations, which may include hypercholesterolemia (Seed et al., *N. Engl. J. Med,* 1990, 322, 1494-1499). Furthermore, elevated plasma levels of the ApoB-100-containing lipoprotein Lp(a) are associated with increased risk for atherosclerosis and its manifestations, which may include hypercholesterolemia (Seed et al., *N. Engl. J. Med,* 1990, 322, 1494-1499). The invention provides a method of lowering serum cholesterol by administering an HBOLD conjugated siRNA to a subject having increased or high levels of cholesterol relative to those accepted as being physiologically normal.

In another embodiment, the invention includes a method of treating obesity by silencing a target gene associated with obesity. Obesity increases a person's risk of illness and death due to diabetes, stroke, coronary artery disease, hypertension, high cholesterol, and kidney and gallbladder disorders. Obesity may also increase the risk for some types of cancer, and may be a risk factor for the development of osteoarthritis and sleep apnea. Obesity can be treated with the siRNA conjugated nanotransporter of the invention alone or in combination with other metabolic disorders, including diabetes.

An obese subject is a subject, e.g., a human subject, who has been diagnosed as being obese (or would be diagnosed as being obese) by a skilled medical practitioner or researcher. Tests utilized in obesity diagnosis include Body Mass Index (BMI)-Calculated by dividing the subject's weight in kilograms by their height in meters squared. A BMI of 25 to 29.9 is considered overweight and 30 or higher is considered obese. (Source: Centers for Disease Control and Prevention and National Heart, Lung, and Blood Institute); Waist Circumference, Saggital Diameter, and Waist-To-Hip Ratio Simple measurements that estimate the amount of fat deposited in the skin and inside the abdominal cavity. Waist circumferences that exceed 100 centimeters (39 inches) in men and 90 centimeters (35 inches) in women are associated with an increased risk of heart disease; Skinfold Caliper—Most fat is deposited beneath the skin. This test measures fat just beneath the skin, but cannot measure fat accumulated inside the abdomen; Water Displacement Tests—Fat is buoyant; other body tissues are not. Determining how well the subject floats provides an estimated ratio of fat to body mass.

An example of a gene which might be targeted by a delivery complex (e.g., a delivery complex including an RNA silencing agent) for the treatment of obesity is RIP 140. As described in Leonardsson et al. (2004) *PNAS* 101:8437, deletion of the RTP140 gene in mice by genetic knockout resulted in the lack of fat accumulation even when mice were fed a high fat diet.

In another embodiment, the invention provides a method of treating diabetes, including diabetes type 2, by silencing a target gene associated with diabetes or insulin regulation. Diabetes includes the two most common types of the disorder, namely type I diabetes and type II diabetes, which both result from the body's inability to regulate insulin. Insulin is a hormone released by the pancreas in response to increased levels of blood sugar (glucose) in the blood.

The term "type 1 diabetes," as used herein, refers to a chronic disease that occurs when the pancreas produces too little insulin to regulate blood sugar levels appropriately. Type 1 diabetes is also referred to as insulin-dependent diabetes mellitus, IDDM, juvenile onset diabetes, and diabetes—type L Type 1 diabetes represents is the result of a progressive autoimmune destruction of the pancreatic-cells with subsequent insulin deficiency.

The term "type 2 diabetes," refers to a chronic disease that occurs when the pancreas does not make enough insulin to keep blood glucose levels normal, often because the body does not respond well to the insulin. Type 2 diabetes is also referred to as noninsulin-dependent diabetes mellitus, NDDM, and diabetes-type II can be diagnosed by the administration of a glucose tolerance test. Clinically, diabetes is often divided into several basic categories. Primary examples of these categories include, autoimmune diabetes mellitus, non-insulin-dependent diabetes mellitus (type 1 NDDM), insulin-dependent diabetes mellitus (type 2 IDDM), non-autoimmune diabetes mellitus, non-insulin-dependent diabetes mellitus (type 2 NIDDM), and maturity-onset diabetes of the young (MODY). A further category, often referred to as secondary, refers to diabetes brought about by some identifiable condition which causes or allows a diabetic syndrome to develop. Examples of secondary categories include, diabetes caused by pancreatic disease, hormonal abnormalities, drug- or chemical-induced diabetes, diabetes caused by insulin receptor abnormalities, diabetes associated with genetic syndromes, and diabetes of other causes (see e.g., Harison's (1996) $14^{th}$ ed., New York, McGraw-Hill).

Diabetes is often treated with diet, insulin dosages, and various medications described herein. Accordingly, the siRNA associated nanotransporter of the invention may also be administered in combination with agents commonly used to treat metabolic disorders and pain commonly associated with diabetes.

A diabetic subject is a subject, e.g., a human subject, who has been diagnosed as having diabetes (or would be diagnosed as having diabetes) by a skilled medical practitioner or researcher. Tests utilized in diabetes diagnosis include the fasting plasma glucose (FPG)test and the glucose tolerance test, e.g., the 75-g oral glucose tolerance test (OGTT). Exemplary criteria for the diagnosis of diabetes are set forth below.

| Normoglycemia | IFG or IGT[‡] | Diabetes* |
|---|---|---|
| FPG <100 mg/dl | FPG >110 | FPG >126 mg/dl |
| 2-h $PG^f$ <140 mg/dl | and <126 mg/dl(IFG) | 2-h $PG^†$ >200 mg/dl |
| | 2-h $PG^f$ >140 | Symptoms of diabetes and |
| | and <200 mg/dl (IGT) | casual plasma glucose |
| | | concentration >200 mg/dl |

[‡]Midrange values indicating impaired glucose tolerance (IGT), or impaired fasting glucose (IFG).
*A diagnosis of diabetes may be confirmed, on a subsequent day, by measurement of FPG, 2-h PG, or random plasma glucose (if symptoms are present). Fasting is defined as no caloric intake for at least 8 hours.
[†]This test requires the use of a glucose load containing the equivalent of 75 g anhydrous glucose dissolved in water. 2-hour PG, 2-hour postload glucose.

An insulin resistant subject is a subject, e.g., a human subject, who has been diagnosed as being insulin resistant (or would be diagnosed as being insulin resistant) by a skilled medical practitioner or researcher. An insulin resistant subject can be identified, for example, by determining fasting glucose and/or insulin levels in the subject. In one embodiment, an insulin resistant subject has a fasting glucose level of less than 110 mg/dL and has a fasting insulin level of greater that 30 mU/L.

An example of a gene which to be targeted by a delivery complex of the invention (e.g., a nanotransporter associated with a target-specific siRNA) for the treatment of diabetes is RIP 140.

The invention also provides a method of treating metabolic disorders wherein the disorder is treated without immunostimulating the recipient subject. For example, by modifying an RNA silencing agent (e.g., an siRNA) with a HBOLD nanotransporter, an interferon response can be reduced or eliminated in a subject having a metabolic disorder undergoing treatment with the RNA silencing agent. Thus, the method of treating a metabolic disorder using the chemically modified RNA silencing agent of the invention provides an improvement over other therapies as it bypasses immunostimulation in the recipient.

The methods of the invention are also suitable for use in methods to identify and/or characterize potential pharmacological agents, e.g., identifying new pharmacological agents from a collection of test substances and/or characterizing mechanisms of action and/or side effects of known pharmacological agents.

Thus, the present invention also relates to a system for identifying and/or characterizing pharmacological agents acting on at least one target protein including (a) a eukaryotic cell or a eukaryotic non-human organism capable of expressing at least one endogenous target gene coding for the so target protein, (b) at least one composition (e.g., a RNA silencing agent or a delivery complex including same) of inhibiting the expression of the at least one endogenous target gene, and (c) a test substance or a collection of test substances wherein pharmacological properties of the test substance or the collection are to be identified and/or characterized. Further, the system as described above comprises: (d) at least one exogenous target nucleic acid coding for the target protein or a variant or mutated form of the target protein wherein the exogenous target nucleic acid differs from the endogenous target gene on the nucleic acid level such that the expression of the exogenous target nucleic acid is substantially less inhibited by the composition than the expression of the endogenous target gene.

The test compounds of the present invention can be obtained using any of the numerous approaches in combinatorial library methods known in the art, including biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad Set U.S.A.* 90:6909; Erb et al. (1994) *Proc. Natl. Acad Set USA* 91:11422; Zuckermann et al. (1994) *J. Med Chem.* 31:261%; Cho et al. (1993) *Science* 261:1303; Carrell et al. (1994) *Angew. Chem. Int. Ed EngL* 33:2059; Carell et al. (1994) *Angew. Chem. Int. Ed Engl.* 33:2061; and in Gallop et al. (1994) *J. Med Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et a. (1990) *Proc. Natl. Acad Sci.* 87:6378-6382); (Felici (1991) *J. Mol Biol* 222:301-310); (Ladner supra)).

In a certain embodiment, the library is a natural product library, e.g., a library produced by a bacterial, fungal, or yeast culture. In another embodiment, the library is a synthetic compound library.

Another use for the siRNA molecules of the present invention (or vectors or transgenes encoding same) is a functional analysis to be carried out in eukaryotic cells, or eukaryotic non-human organisms, mammalian cells or organisms and human cells, e.g., cell lines such as HeLa or 293 or rodents, e.g., rats and mice. By administering a suitable siRNA molecules which is sufficiently complementary to a target mRNA sequence to direct target-specific RNA interference, a specific knockout or knockdown phenotype can be obtained in a target cell, e.g., in cell culture or in a target organism.

Thus, a further subject matter of the invention is a eukaryotic cell or a eukaryotic non-human organism exhibiting a target gene-specific knockout or knockdown phenotype including a fully or at least partially deficient expression of at least one endogenous target gene wherein the cell or organism is transfected with at least one vector including DNA encoding a siRNA molecule capable of inhibiting the expression of the target gene. It should be noted that the present invention allows a target-specific knockout or knockdown of several different endogenous genes due to the specificity of the RNA silencing agent.

Gene-specific knockout or knockdown phenotypes of cells or non-human organisms, particularly of human cells or non-human mammals may be used in analytic to procedures, e.g., in the functional and/or phenotypical analysis of complex physiological processes such as analysis of gene expression profiles and/or proteomes. The analysis may be carried out by high throughput methods using oligonucleotide based chips.

The invention pertains to uses of the any of the above-described nanotransporters or RNA silencing agents for therapeutic treatments as described infra. Accordingly, the nano transporters of the present invention can be incorporated into pharmaceutical compositions suitable for administration. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition may be sterile and should be fluid to the extent that easy syringability exists. It should be stable under the conditions of manufacture and storage and may be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it may include isotonic agents, for example, sugars, polyalcohols such as manito], sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The compounds can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am J. Health Syst. Pharm. 53(2), 151-160, erratum at Am. J. Health Syst. Pharm. 53(3), 325 (1996).

The compounds can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the LD50 of the dose lethal to 50% of the nonulation^ and the ED50 of the dose therapeutically effective in 50% of the population). The dose ratio between toxic and therapeutic effects is the therapeutic index and it can be expressed as the ratio LD50/ED50. Compounds which exhibit high therapeutic indices. While compounds that exhibit toxic side effects may be used, care should be taken to design a delivery system that targets such compounds to the site of affected tissue in order to minimize potential damage to uninfected cells and, thereby, reduce side effects.

A therapeutically effective amount of a composition containing a compound of the invention (e.g., a siRNA, candidate siRNA derivative, modified siRNA, etc.) (i.e., an effective dosage) is an amount that inhibits expression of the polypeptide encoded by the target gene by at least 30 percent. Higher percentages of inhibition, e.g., 45, 50, 75, 85, 90 percent or higher may be achieved in certain embodiments. Exemplary doses include milligram or microgram amounts of the molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. The compositions can be administered one time per week for between about 1 to 10 weeks, e.g., between 2 to 8 weeks, or between about 3 to 7 weeks, or for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments.

It is furthermore understood that appropriate doses of a composition depend upon the potency of composition with respect to the expression or activity to be modulated. When one or more of these molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The data obtained from the cell culture assays and animal studies can be used in formulating a range of dosage for use in humans. The dosage of such compounds lies within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

Physical methods of introducing the compositions (e.g., nanotransporters, RNA silencing agents, or delivery complexes) of the present invention include injection of a solution containing the composition, bombardment by particles covered by the composition, or electroporation of cell membranes in the presence of the composition. Where the composition comprises a nucleic acid molecule, a viral construct packaged into a viral particle would accomplish both efficient introduction of an expression construct into the cell and transcription of a nucleic acid molecule encoded by the expression construct. Other methods known in the art for introducing nucleic acids to cells may be used, such as lipid-mediated carrier transport, chemical-mediated transport such as calcium phosphate, and the like. Thus the nucleic acid (e.g., RNA silencing agent) may be introduced along with components that perform one or more of the following activities: enhance nucleic acid uptake by the cell, inhibit annealing of strands, stabilize the strands, or otherwise increase inhibition of the target gene.

Compositions may be directly introduced into the cell (i.e., intracellularly); or introduced extracellularly into a cavity, interstitial space, into the circulation of an organism. Vascular or extravascular circulation, the blood or lymph system, and the cerebrospinal fluid are sites where the compositions may be introduced.

The cell with the target gene may be derived from or contained in any organism, including animals including vertebrate animals. Examples of vertebrate animals include, but are not limited to, fish, mammal, cattle, goat, pig, sheep, rodent, hamster, mouse, rat, primate, and human. The agents of the instant invention are especially suited for use in humans.

Depending on the particular target gene and the dose of composition delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

Quantitation of the amount of gene expression allows one to determine a degree of inhibition which is greater than 10%, 33%, 50%, 90%, 95% or 99% as compared to a cell or organism not treated according to the present invention. Lower doses of injected material and longer times after administration of the composition may result in inhibition in a smaller percentage of inhibition (e.g., at least 10%, 20%, 50%, 75%, 90%, or 95% inhibition). Quantitation of gene expression may show similar amounts of inhibition at the level of accumulation of target mRNA or translation of target protein. As an example, the efficiency of inhibition may be determined by assessing the amount of gene product, for example in a cell or sample derived from a treated organism; mRNA may be detected with a hybridization probe having a nucleotide sequence outside the region used for the inhibitory double-stranded RNA, or translated polypeptide may be detected with an antibody raised against the polypeptide sequence of that region.

The composition may be introduced in an amount which allows delivery of at least one molecule (e.g., at least one copy of RNA) per cell. Higher doses (e.g., at least 5, 10, 100, 500 or 1000 copies per cell) of material may yield more effective inhibition; lower doses may also be useful for specific applications.

All references, patents or applications, U.S. or foreign, cited in the application are hereby incorporated by reference as if written herein in their entireties. Where any inconsistencies arise, material literally disclosed herein controls.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLE 1

Experimental Materials and Methodologies

The following materials and methods were used.
Oligonucleotides.

Custom-made RNAs were purchased from Dharmacon (Lafayette, Colo.) and consisted of 23-24 nucleotides length with modifications as specified: chemically modified anti-miR-122 (CM): 5'-AC$^F$AAAC$^F$AC$^F$C$^F$AUUGUCACA-CUCCA-3' SEQ ID NO:1); chemically modified mismatch anti-miR-122 (MM): 5'-UCAC$^F$AAC$^F$CUCC$^F$UA-GAAAGAOUAGA-3' (SEQ ID NO: 2). The superscript letter F represents 2'-O-F modified nucleotides. The complexes were prepared by mixing CM or MM anti-miR with iNOP-7 at a ratio of 1:10 (w/w) in HEPES saline or Opti-MEM culture medium (Invitrogen, Carlsbad, Calif.) and incubating at room temperature for 20 minutes.

In Vitro Silencing of miR-122.

Huh-7 cells (kindly provided by John Taylor, Fox Chase Cancer Center) were maintained at 37° C. with 5% $CO_2$ in DMEM with High Glucose culture medium (Invitrogen, Carlsbad, Calif.) supplemented with 10% fetal bovine serum, 100 U mL$^{-1}$ penicillin and 100 μg mL$^{-1}$ streptomycin. Cells were regularly passaged and plated in 6-well culture plates for 16 h before transfection at 70% confluency. Cells were transfected with 1 mL well$^{-1}$ of complex for 4 h at 37° C. Efficiency of silencing was determined by northern blotting as described below.

Dual Luciferase Assay.

The miR-122 luciferase constructs were engineered by inserting the full 23 bp sequence complementary to the mature miR-122 into the 3'-UTR of pGL3-Control (Promega, Madison Wis.). Huh-7 cells were seeded in 24-well culture plates and transfected with 0.1 μg miR-122 pGL3-Control plasmid and 0.015 μg pRL-TK plasmid (Promega, Madison Wis.) for normalization using iNOP-7. After 4 h of transfection, cells were treated with complete media. Cells were lysed 48 hours later, unless otherwise indicated, and luciferase activity was measured using the Dual-Luciferase Reporter Assay System (Promega, Madison Wis.).

In Vivo Silencing of miR-122.

All animal procedures were approved by the Institutional Animal Care and Use Committee (University of Massachusetts Medical School). Six- to eight-week-old male C57BL/6 mice (Charles River Laboratories, Wilmington, Mass.) were maintained under a 12 hour dark cycle in a pathogen-free animal facility. Mice were administrated with either phosphate buffered saline pH 7.4 (PBS) or iNOP-7 complexes (as indicated) at 2 mg kg$^{-1}$ body weight in 0.2 ml per injection as bolus injection via the lateral tail vein at 0 hours, 12 hours and 36 hours. Measurements of miRNA or mRNA levels in tissues were performed 24 hours after the last injection unless indicated otherwise. Liver and plasma were collected and stored in −80° C. until analysis.

Northern Blotting.

RNA from cell culture or mouse livers was homogenized in TRIZOL (Invitrogen, Carlsbad, Calif.) and isolated according to the manufacturer's instructions. Total RNA was separated on a 14% acrylamide/20% formamide/8 M urea gel, then electroblotted onto Hybond-XL nylon membrane (GE Healthcare, Piscataway, N.J.). The probe with γ$^{32}$P-labelled oligonucleotides for miRNA or rRNA was hybridized to the membrane at 42° C. The blots were visualized by scanning in a FLA-5000 scanner (Fujifilm, Stamford, Conn.).

Quantitative Real-Time PCR.

To determine regulations of mRNA levels in mouse tissues after anti-miR treatment, total RNA was extracted with TRIZOL (Invitrogen, Carlsbad, Calif.) and treated with TORBO DNA-free kit (Applied Biosystems, Foster City, Calif.) before quantification. In preparation for quantitative PCR, total RNA (400 ng) was reverse transcribed by using SuperScript II (Invitrogen, Carlsbad, Calif.) and random primers according to the manufacturer's protocol. The expression of mRNA was measured using ABsolute QPCR SYBR green mix (ThermoFisher Scientific, Epsom, Surrey, UK) normalized to GAPDH according to the manufacturer's instructions. Quantitative PCR was performed by using a Chromo4 Real-Time PCR Detection System (BioRad, Hercules, Calif.).

Measurement of Total Cholesterol Levels in Plasma.

Plasma cholesterol was measured by Cholesterol E kit according to the manufacturer's instructions (Wako, Richmond, Va.).

In Vivo Interferon Induction.

To assess for any nonspecific immune response to injected iNOP-containing anti-miR, mouse liver tissue RNA was analyzed for expression of the IFN-inducible genes by quantitative RT-PCR.

Statistical Analysis.

Results are given as means: SD. Statistical analyses are performed with Student's t-test, and the null hypothesis was rejected at the 0.05 level.

EXAMPLE 2

Silencing Potency of iNOP-7 Containing Chemically Modified Anti-miR-122

Figure 1B:
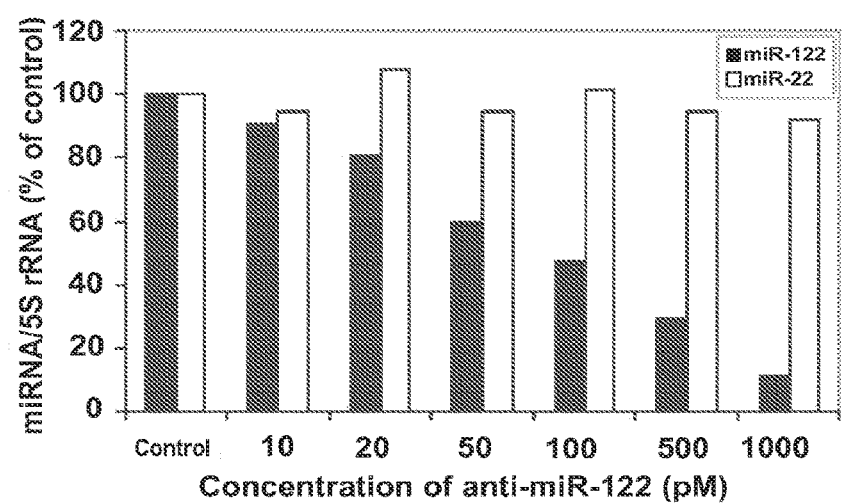

The silencing potency of iNOP-7 containing chemically modified anti-miR-122 was first evaluated in Huh-7 cells. The cells were transfected by iNOP-7 containing anti-miR-122 and analyzed the miR-122 by Northern blotting: Huh-7 cells were transfected by iNOP-7 containing anti-miR-122 at varying concentrations as indicated for 4 hours. Total RNA was isolated from cells 24 hours after transfection and separated on 14% polyacrylamide gels. iNOP-7 efficiently delivered anti-miR-122 into the cells and specifically silenced miR-122 in a dose-dependent manner. The endogenous miR-122 was slightly reduced by 10 pM of anti-miR-122 compared with nontransfected control and ~90% of miR-122 was silenced at 1 nM, which is at least 50 times lower than 2'-OMe and/or locked nucleic acid (LNA) modified anti-miR inhibitors transfected by Lipofectamine 2000. These results suggest that iNOP-7 can efficiently deliver chemically modified anti-miR to cytoplasm and the released anti-miR results in lowering the miR-122 levels in cell. Furthermore, the expression level of miR-22 was unaffected by the transfection, indicating that the anti-miR silencing was miRNA specific (FIG. 1B) and Northern blotting (as described above).

EXAMPLE 3

Specific Anti-miRNA Effectiveness

Figure 2:
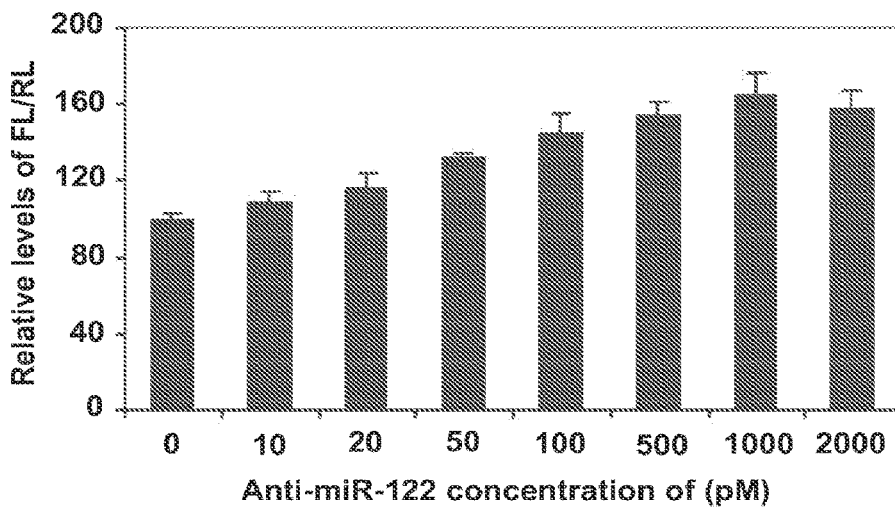
FIG. 2 illustrates the determination of the inhibition of miR-122 by iNOP-7 in vitro by dual luciferase assays. Huh-7 cells were transfected with miR-122 luciferase construct containing sequence complementary to the mature miR-122 into the 3'-UTR and varying amounts of anti-miR oligonucleotides using iNOP-7 for 4 hours. Cells were lysed 48 hours later, and luciferase activities were measured using the Dual-Luciferase Reporter Assay System as described previously (Chu and Rana 2006; Chu and Rana 2008).

To evaluate the specific anti-miRNA effectiveness, perfectly complementary miR-122 binding sites were incorporated into the 3'-UTR of a luciferase sensor plasmid as previously reported. When the reporter was transfected into Huh-7 cells, the endogenously expressed miR-122 strongly repressed the luciferase sensor expression by binding with perfect complementarity and causing cleavage of the mRNA. Introduction of anti-miR-122 by iNOP-7 prevented this miR-122-mediated repression, resulting in increased luciferase expression (FIG. 2). The results are inversely consistent with the silencing effect of endogenous miR-122 by iNOP-7 containing anti-miR-122 detected by Northern blotting (as described in Example 1). Total RNA was isolated from cells 24 hours after transfection and separated on 14% polyacrylamide gels. Membrane was probed for miR-122 and miR-22, respectively. 5S rRNA is shown as a loading control. Northern blots of miR-122 and miR-22 (as described in Example 1) were analyzed by densitometry and normalized to 5S rRNA.

EXAMPLE 4

In Vivo Silencing of iNOP-7 Containing Chemically Modified Anti-miR-122

Figure 3A:
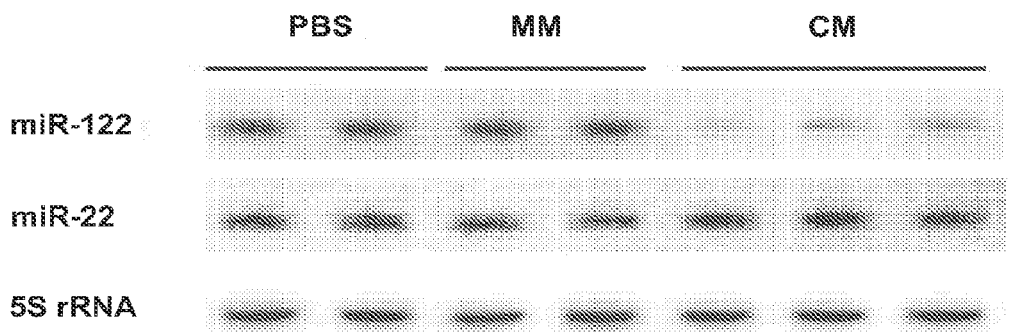
FIGS. 3A and 3B illustrate the specific silencing of miR-122 in mice treated with iNOP-7 assembled with chemically modified anti-miR-122. Quantification of reduced miR-122 levels in mice after treatment with iNOP-7 containing anti-miR-122 is also depicted. (A) Mice were injected with 2 mg kg$^{-1}$ of iNOP-7 containing chemically modified anti-miR-122, mismatched chemically modified anti-miR-122 or PBS. Total RNA was isolated from mouse liver 24 hours after last injection. Samples were separated in 14% polyacrylamide gel and membrane was probed for miR-122, miR-22, and 5S rRNA. 5S rRNA is shown as a loading control. (B) Quantification of reduced miR-122 levels in mice after treatment with iNOP-7 containing anti-miR-122. Northern blots of miR-122 and miR-22 (panel a) were analyzed by densitometry after normalized to 5S rRNA. Data are expressed as a percent of control (2 or 3 animals).
Figure 3B:
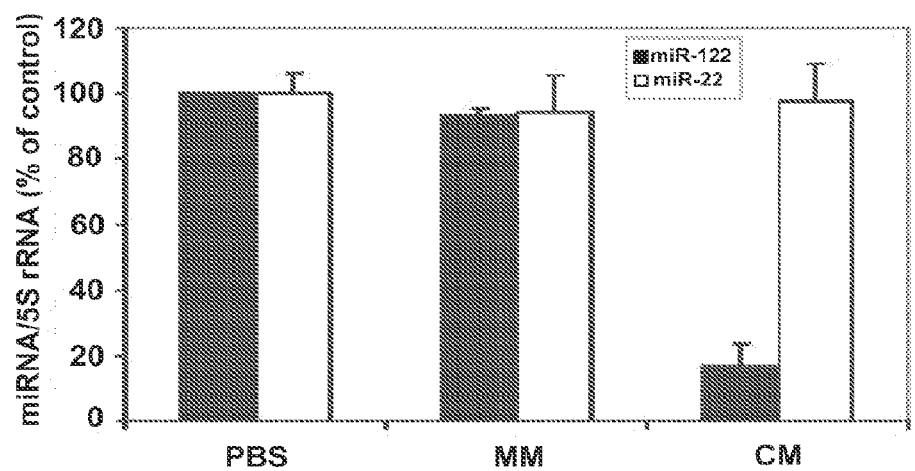

The ability of iNOP-7 to deliver anti-miR-122 to its target and silence miR-122 in vivo was next determined. Mice were injected via tail vein with iNOP-7 complexed to either chemically modified anti-miR-122 or its mismatch on three consecutive days, and samples of liver and plasma were analyzed. miR-122 was significantly lower in liver tissue from mice treated with 2 mg kg$^{-1}$ iNOP-7 containing chemically modified anti-miR-122 (83.2±6.4%, n=3 animals) than in livers from control mice (FIG. 3). The effects of anti-miR-122 were found to be specific because mice injected with iNOP-7 containing mismatched anti-miR-122 has no effect on miR-122. Furthermore, the expression of miR-22 was unaffected in mice treated with anti-miR-122 and its mismatch, suggesting that silencing was miRNA specific.

EXAMPLE 5

In Vivo Duration of Silencing of miRNA-22

The duration of silencing that could be achieved after the injection of iNOP-7 containing chemically modified anti-miR-122 was also tested. Mice were injected with 2 mg kg$^{-1}$ of iNOP-7 containing chemically modified anti-miR-122 via tail vein, isolating liver tissues at various times after injection, and analyzing liver for miR-122 levels. At day 1, miR-122 level was significantly decreased (over 80% compared to PBS control mice), and the effect lasted up to nine days, indicating that silencing of miRNA by iNOP-7 containing chemically modified anti-miR-122 is long lasting effects. The duration of silencing miR-122 in mice treated with iNOP-7 containing chemically modified anti-miR-122 has been shown. Mice were injected with 2 mg kg$^{-1}$ of iNOP-7 containing chemically modified anti-miR-122 at 0 hours, 12 hours and 36 hours. Total RNA was isolated from mouse livers at different days as indicated after last injection as well as from livers of mice administrated with PBS. Samples were separated in 14% polyacrylamide gel and membrane was probed for miR-122. Ethidium bromide staining of tRNA is shown as a loading control.

EXAMPLE 6

In Vivo Efficacy of miRNA-122 Inhibition

Figure 4A:
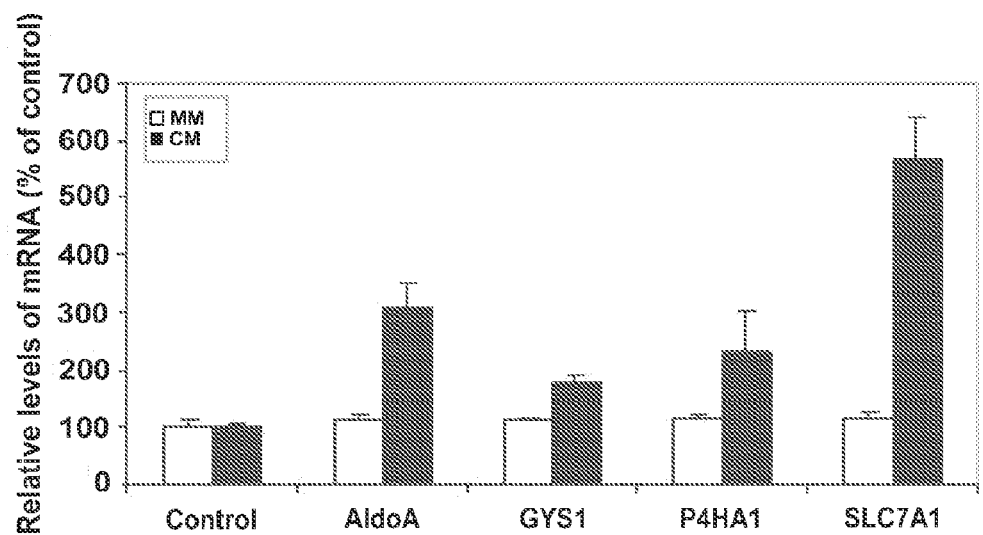
FIGS. 4A, 4B and 4C illustrate regulations of gene expression by anti-miR-122-iNOP-7 treatment in mice. Mice were injected with 2 mg kg$^{-1}$ of iNOP-7 containing chemically modified anti-miR-122, mismatched chemically modified anti-miR-122, or PBS. Total RNA was isolated from mouse liver 24 hours after last injection. mRNA levels were up-regulated (A) or down-regulated (B) in liver 24 hours after last injection. Values represent the mean±SD of tissue samples for 2 liver regions (3 animals). Data are expressed as percent of PBS treated mice. AldoA: aldolase 1, A isoform; GYSI: glycogen synthase 1; P4HA1: procollagen-proline, 2-oxoglutarate 4-dioxygenase (proline 4-hydroxylase), alpha 1 polypeptide; SLC7A1: solute carrier family 7 (cationic amino acid transporter, y+ system), member 1; ACACB: acetyl-Coenzyme A carboxylase beta; Acas2: acetyl-coenzyme A synthetase 2; ApoB: apolipoprotein B; FASN: fatty acid synthase; HMGCR: 3-hydroxy-3-methylglutaryl-Coenzyme A reductase; SCD1: stearoyl-Coenzyme A desaturase 1. (C) Total cholesterol in plasma after anti-miR-122 treatment of mice. Mice were injected with 2 mg kg$^{-1}$ of iNOP-7 containing chemically modified anti-miR-122, mismatched chemically modified anti-miR-122 and PBS on three consecutive days. Plasma was collected at 24 hours after last injection and total cholesterol was measured by Cholesterol E kit from Wako (n=3 animals). * p<0.05
Figure 4B:
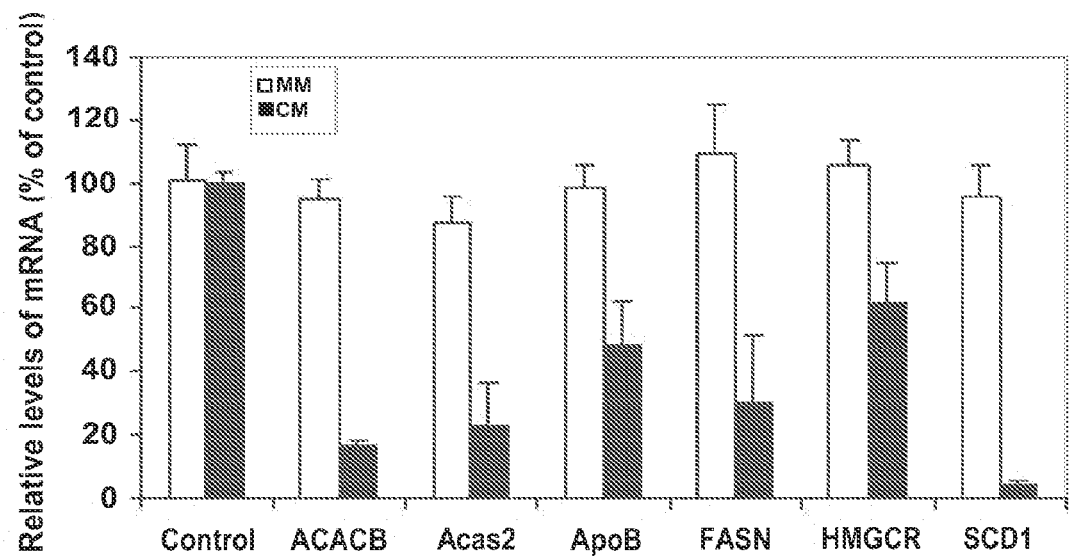

MicroRNA can regulate the mRNA levels of their targets in 3'-UTR and pharmacological silencing miRNAs using iNOP-7 containing chemically modified anti-miR-122 might therefore lead to the regulation of many mRNAs. To demonstrate the efficacy of the miRNA inhibition in vivo, the levels of a set of miR-122 target mRNAs identified previously were evaluated in quantitative RT-PCR (FIG. 4). Four often target mRNAs were increased in the anti-miR-122 treated mice, among which SLC7A1 mRNA was most sensitive to miR-122 inhibition (fold increase 5.7±0.7) (FIG. 4A). The other six mRNAs were downregulated after the inhibition of miR-122 and SCD1 was decreased to 4.3±1.7% of control after the inhibition (FIG. 4B). No target mRNA changes were observed in mice treated with mismatched anti-miR-122, demonstrating specific inhibition of miR-122 activity in liver.

EXAMPLE 7

Physiological Effects of mRNA-122 Silencing on Cholesterol Metabolism

Figure 4C:
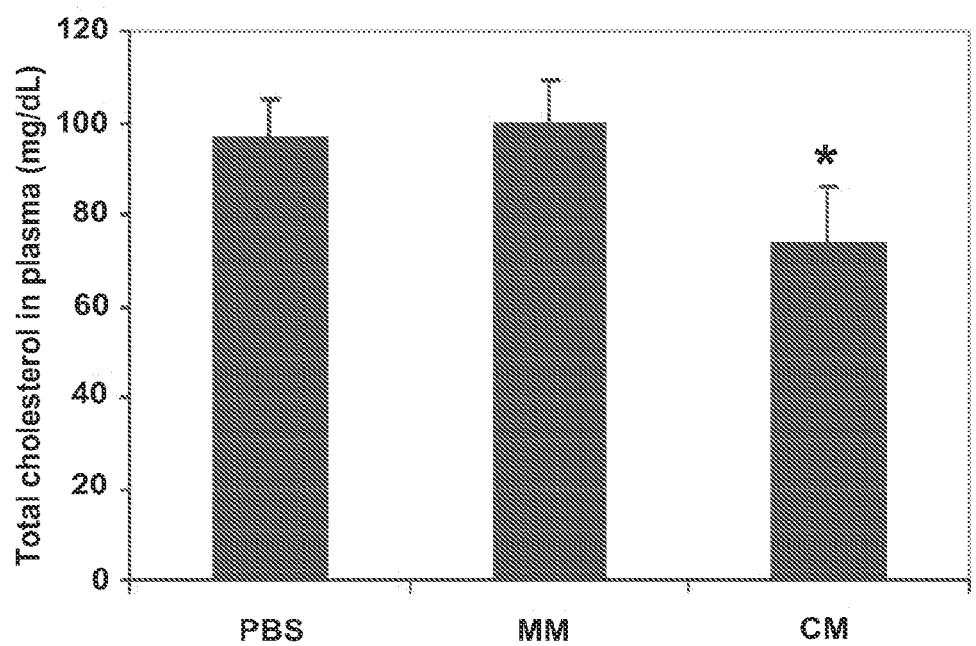

To investigate the physiological effects of miR-122 silencing on cholesterol metabolism, the total plasma cholesterol levels in mice 24 hours after the last injection were measured. Chemically modified anti-miR-122 mediated regulation of gene expression in liver caused the reduction of total cholesterol in plasma (26.3-12.5%) as shown in FIG. 4C. Cholesterol levels were unchanged in mice receiving control treatments or treated with iNOP-7 containing chemically modified, mismatched anti-miR-122. This result demonstrates that iNOP-7-mediated targeting of miR-122 could provide a clinically significant new approach to reducing cholesterol levels in patients with hypercholesterolemia.

EXAMPLE 8

In Vivo Evaluation of Immune Response to and Toxicity of iNOP-7 Containing Chemically Modified Anti-miR-122

Figure 5:
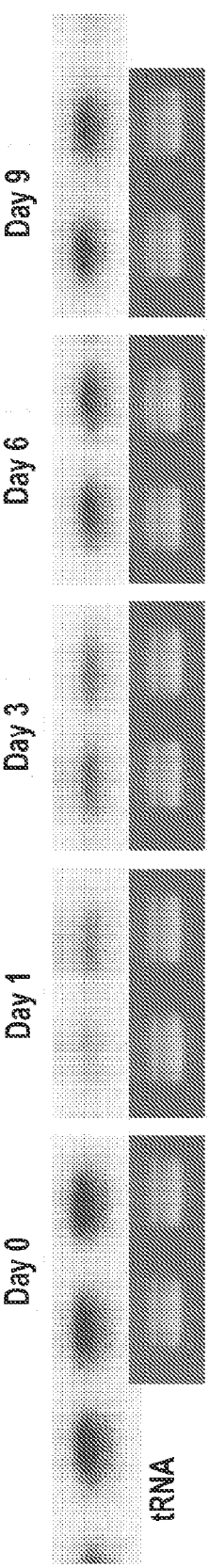
FIG. 5 illustrates the duration of silencing miR-122 in mice treated with iNOP-7 containing chemically modified anti-miR-122. Mice were injected with 2 mg kg$^{-1}$ of iNOP-7 containing chemically modified anti-miR-122 at 0 hours, 12 hours, and 36 hours. Total RNA was isolated from mouse livers at different days as indicated after last injection as well as from livers of mice administered with PBS. Samples were separated in 14% polyacrylamide gel and membrane was probed for miR-122. Ethidium bromide staining of tRNA is shown as a loading control.

To address the concern of eliciting a nonspecific immune response by injecting animals with iNOP-7 containing chemically modified anti-miR-122, liver tissue RNA was assessed by quantitative PCR for the induction of the interferon inducible genes IFIT1 (interferon-induced protein with tetratricopeptide repeats 1), STAT 1 (signal transducers and activators of transcription 1) and OAS1 (2',5'-oligoadenylate synthetase 1). The results show that injecting mice with iNOP-7 containing either chemically modified or mismatched anti-miR-122 did not alter the expression of these genes in the liver, suggesting iNOP-7 treatment did not induce an immune response in mice (FIG. 5). Anti-miR-122 was well tolerated after injection of 2 mg kg$^{-1}$ of chemically modified anti-miR-122 complexed with iNOP-7 on three consecutive days; no alterations in overall health, body weight and food intake were detected. Together, these data indicate that iNOP-7 containing chemically modified anti-miR-122 participates in regulation of the cholesterol biosynthetic pathway and that silencing of a miRNA can be achieved without apparent toxicities.

EXAMPLE 9

Tissue Specific Delivery of RNAi by Modified iNOPS

A series of surface modifications to the dendrimers were undertaken to produce new iNOPs for tissue-specific delivery of RNAi. These modifications were designed to increase tissue distribution and decrease cytotoxicity. As shown in Scheme I below, ten functional groups were prepared, including groups having a biodegradable linkage inside the spacer (an ester bond in A and B, and a disulfide bond in C) in order to facilitate the release of siRNA cargo upon exposure to the cytoplasm. Other modifications include functional groups designed to enhance either endosomal escape (E) or in vivo uptake (J).

about 2.5, as calculated from the difference between the molecular weight of iNOP-7 and the resulting iNOP-7Lac obtained from MALDI-TOF mass analysis. iNOP-7 showed 10 distinct peaks, with 5814.9 being the most abundant one, corresponding to a generation 4 poly-L-lysine dendrimer bearing 7 lipid chains. iNOP-7Lac gave broader distribution in MALDI-TOF mass spectrum, with most abundant peak showing at approximately 6,600 and a smaller peak at around 3,300 representing M+2H*. TAT peptide (J) was

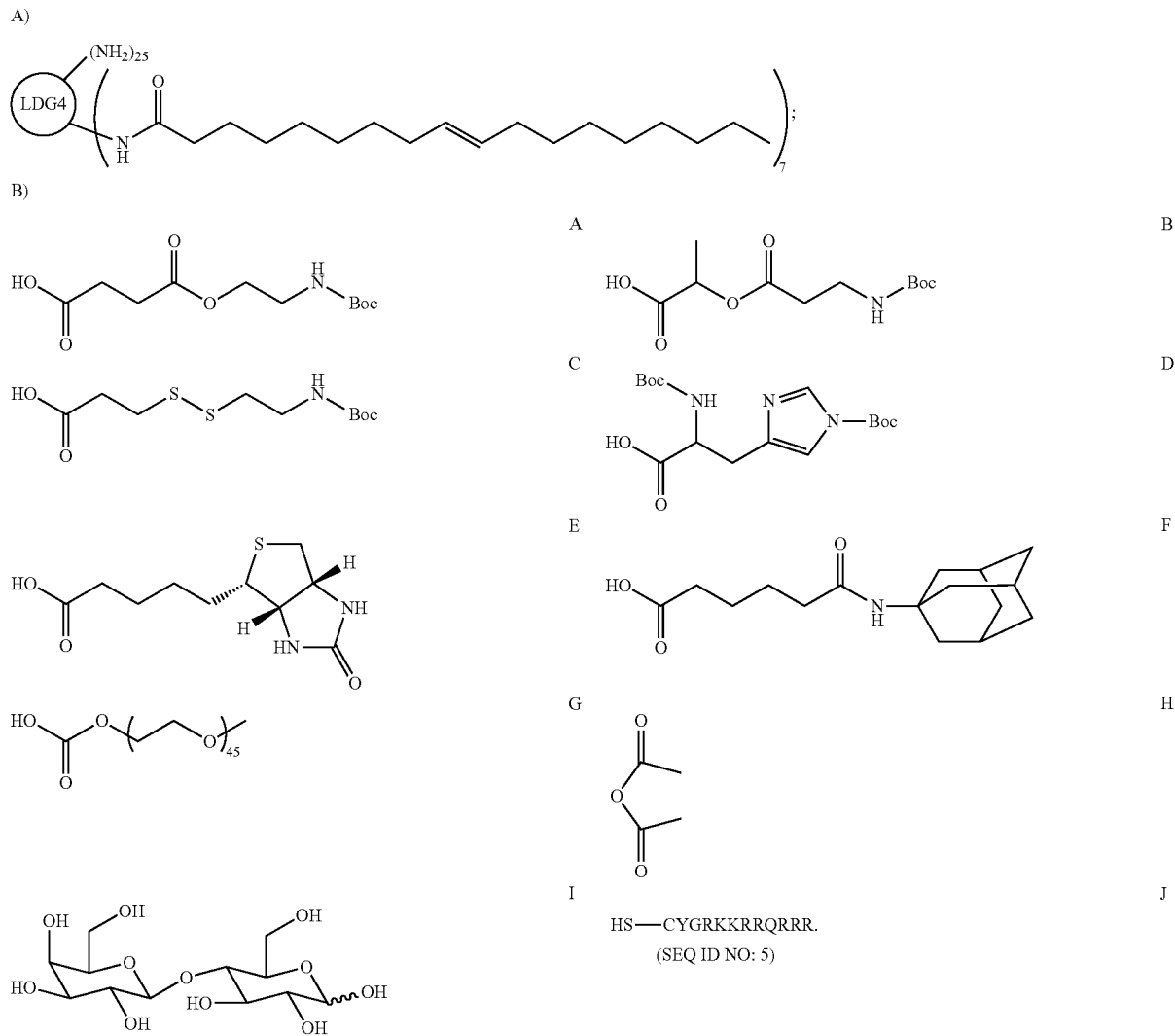

Structure of A) iNOP-7; and B) reacting groups that were used for generating iNOP-7 derivatives: A, iNOP-7E; B, iNOP-7LE; C, iNOP-7DS; D, iNOP-7His; E, iNOP-7Bio; F, iNOP-7AD; G, iNOP-7PEG; H, iNOP-7A; I, iNOP-7Lac; J, iNOP-7TAT.

As shown in Scheme I, part B, functional groups A-H were each conjugated to iNOP-7 through amide bonds using BOP as a condensing agent. Groups A-D were used in excess to ensure complete substitution on the surface of the dendrimer, while Groups E-J were reacted in a controlled ratio of 1:2-5 to conserve amino groups. The resulting iNOP-7 derivatives were either treated with TFA to deprotect the anime (Groups A-D), or used for siRNA delivery without further treatment (Groups E-J). Lactose (I) was coupled to iNOP-7 through reductive amination. A feeding ratio of 1:3 (iNOP-7 to lactose) gave a degree of substitution (DS) of reacted to succinimidyl 4-[p-maleimidophenyl]butyrate (SMPB) modified iNOP-7 through Michael Addition. MALDI-TOF mass spectrum of resulting iNOP-7TAT indicated that 1-4 peptides were successfully conjugated.

iNOP-7 and its derivatives readily forms nanoparticles upon mixing with siRNA in buffers. Under the same formulating conditions different iNOP-7 derivatives show different size distributions, ranging from 50 nm to 220 nm. The influence of particle size, charge density and surface modification of iNOP-7 derivatives on their siRNA delivery efficiency in different tissues was further explored. Table 1 provides the size distribution profiles as determined by dynamic light scattering.

TABLE 1

| iNOP-7s | Size (nm) |
|---|---|
| iNOP-7 | 163 |
| iNOP-7A | 183 |
| iNOP-7DS | 138 |
| iNOP-7E | 170 |
| iNOP-7LE | 176 |
| iNOP-7His | 186 |
| iNOP-7AD | 173 |
| iNOP-7Bio | 193 |
| iNOP-7Lac | 230 |
| iNOP-7TAT | 158 |
| iNOP-7PEG | 48 |

To determine whether iNOP derivatives could deliver siRNA to its target, FL83B cells were treated with iNOP derivatives complexed with apoB siRNA and analyzed apoB mRNA levels by quantitative polymerase chain reaction (qRT-PCR). Stability of the siRNA component of the iNOP derivatives was enhanced through use of chemically modified siRNA sequences targeting apoB according to modification rules established in previous studies. All iNOP derivatives containing apoB siRNA silenced apoB mRNA expression (75%-90%) in FL83B cells relative to controls. Such reduced apoB mRNA levels were not due to iNOP derivative-induced cell toxicity, as confirmed by a modified MTS cell viability assay. These results demonstrate that modified iNOP derivatives efficiently transport siRNA into cells with minimal toxicity.

Figure 6:
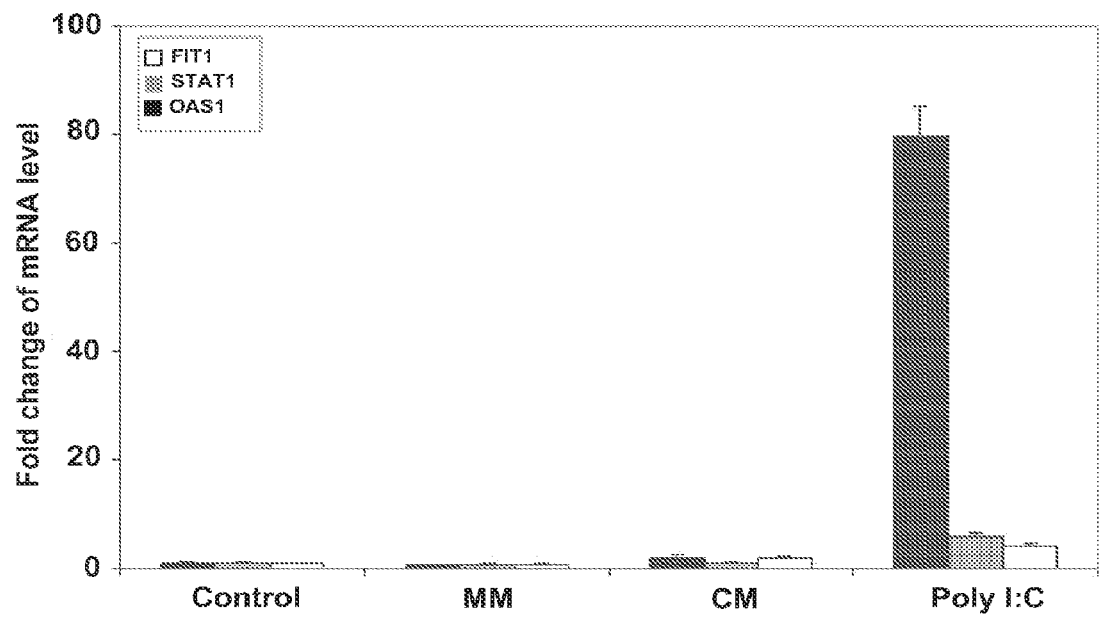
FIG. 6 illustrates the immune response of iNOP-7 in mice. iNOP-7 treatment does not induce the interferon responsive genes in mouse liver. Expression of the genes was analyzed in liver of mice 24 hours after the injection with 2 mg kg$^{-1}$ iNOP-7 containing either chemically modified siRNA (CM) or mismatched siRNA (MM). Values represent the mean±SD of tissue samples for 2 liver regions (3 animals). Data are expressed as percent of PBS treated mice. As positive control, animals were injected with 250 μg of poly I:C to induce interferon responses.

We next examined apoB siRNA tissue distribution in iNOP derivative-injected mice by Northern analysis of total RNA isolated from mouse liver, spleen, lung and kidney. As illustrated in FIG. 6, our results show that the guide strand was present mainly in liver, spleen and lung 48 h after injection. Surprisingly, some iNOP derivatives delivered siRNA preferentially to specific organs. For example, guide strand RNA was predominantly detected in liver in mice injected with iNOP-7Lac. Increased amounts of guide strand siRNA were also found in liver of animals treated with iNOP-7E and iNOP-7LE, both of which contain a degradable ester bond on the surface, indicating that more easily biodegradable iNOP derivatives may facilitate siRNA cargo release in organs like liver where levels of digestive enzymes (such as esterase) are high. On the other hand, elevated levels of guide strand siRNA were detected in the spleen of mice injected with iNOP7PEG, while iNOP-7AD and iNOP-7TAT delivered siRNA at similar levels in liver, spleen and lung.

Since iNOP-7Lac can specifically target liver, it was chosen to further evaluate its siRNA delivery efficiency in vitro and in vivo. As shown in Table 2, iNOP-7Lac delivered siRNAs to both human and mouse cell lines in high efficiency that is comparable to commercial transfection agent lipofectamine 2000.

TABLE 2

In vitro Gene Silencing Efficiency (mRNA level[a]) of iNOP-7Lac

| Target gene[b] | Cell line | Negative control[c] | Lipofectamine 2000 | iNOP-7Lac[d] |
|---|---|---|---|---|
| DDB1 | Hep3B | 100% | 10% | 5% |
| DDB1 | Huh7 | 100% | 20% | 20% |
| ApoB | FL83B | 100% | 10% | 8% |
| Cdk9 | MEF | 100% | 20% | 25% |
| Trp53 | MEF | 100% | 5% | 9% |

[a]Quantified by qRT-PCR.
[b]Final concentration of siRNA for transfection is 50 nM.
[c]Mismatch siRNA complexed with iNOP-7Lac as negative control.
[d]Final concentration for transfection is 1.0 nM.

Figure 7:
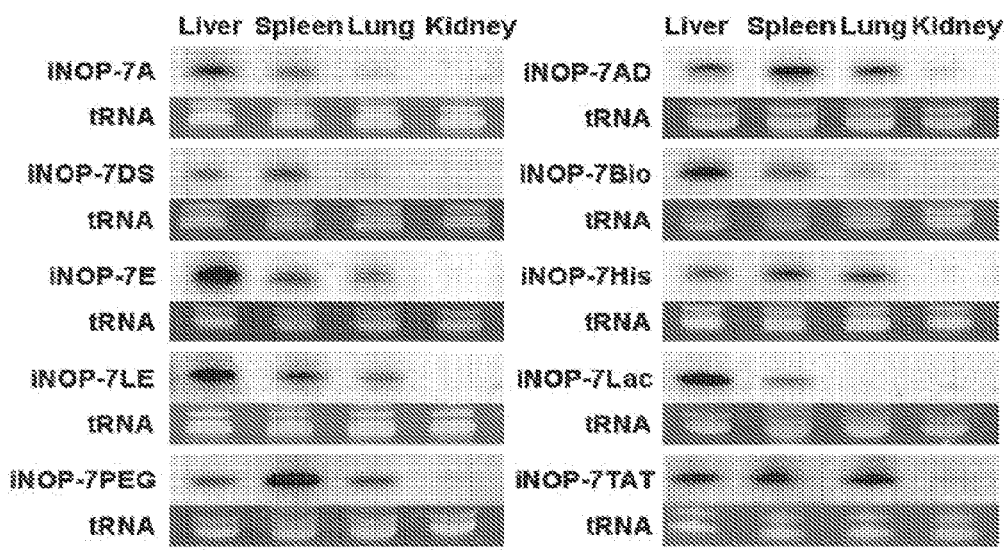
FIG. 7 illustrates the biodistribution of apoB guide strand siRNA delivered by iNOP derivatives in mouse tissues after intravenous (i.v.) injection. Northern blots of total RNA (~10 ug) isolated from different mouse tissues 48 h after i.v. injection of 1 mg kg−1 iNOP-7s. Ethidium bromide staining of tRNA is shown as a loading control.
Figure 8A:
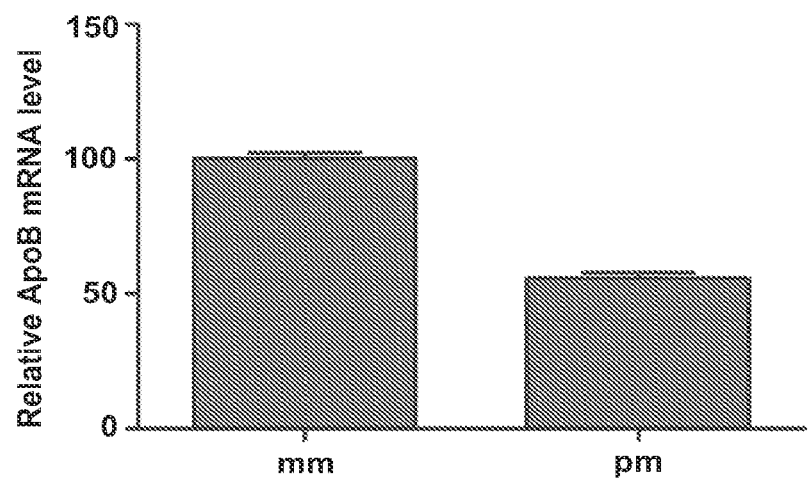
FIGS. 8A and 8B illustrates the following: A) in vivo silencing of mouse liver apoB by iNOP-7Lac compiexed to perfect match siRNA (pm). A mismatch (mm) siRNA compiexed to iNOP-7Lac was injected as a negative control. B) In vivo silencing of Cdk9 by iNOP-7 or iNOP-7TAT. A graph showing Cdk9 is silenced in the liver, spleen and lung of mice 48 h after treatment with CM Cdk9 siRNA compiexed to iNOP-7 or iNOP-7TAT (n=3 mice/group). Data are expressed as meantSEM relative to control.
Figure 8B:
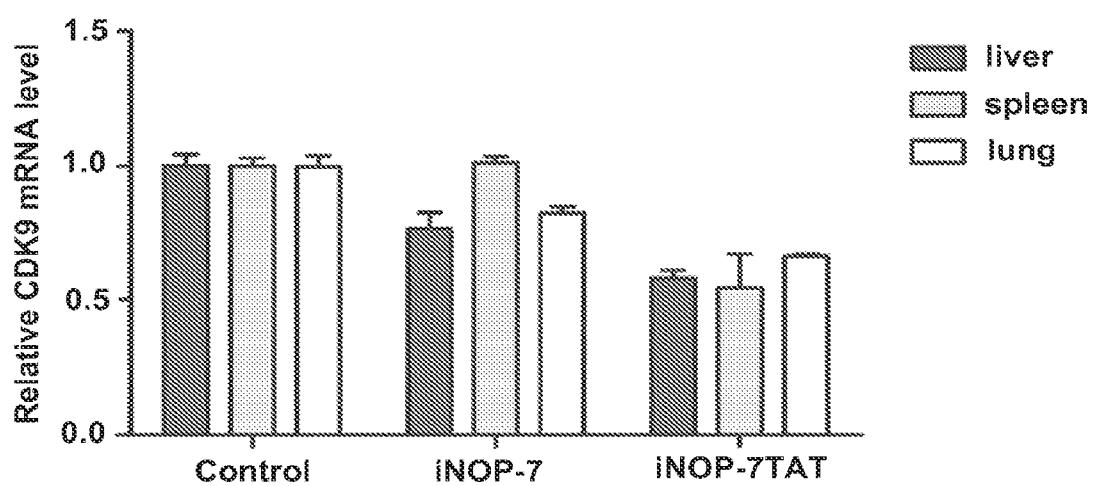
Figure 9:
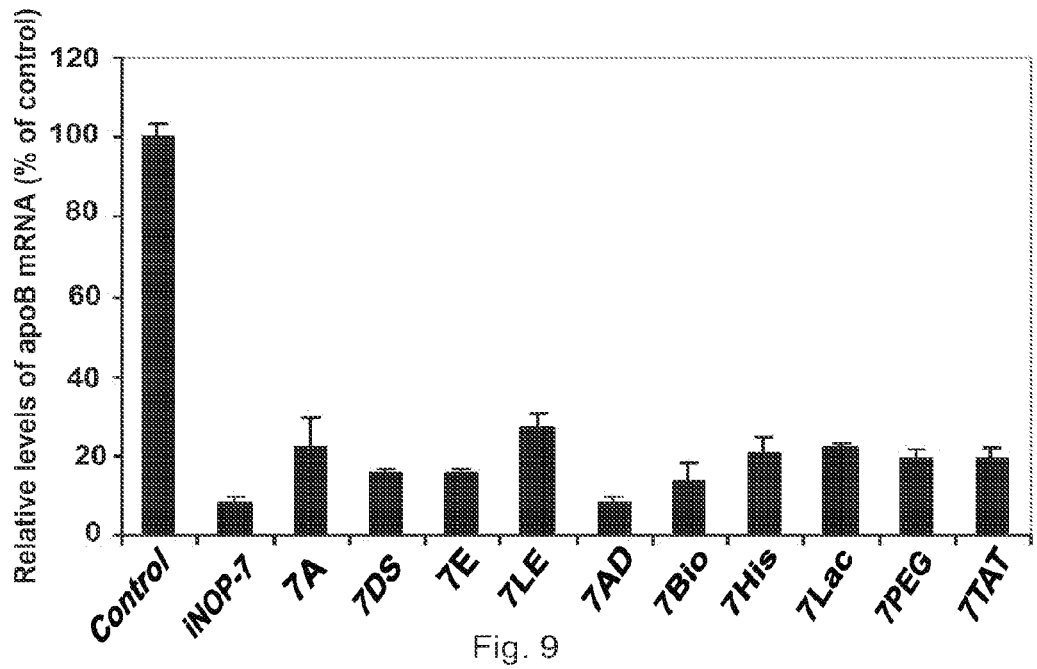
FIG. 9 illustrates the in vitro silencing of apoB mRNA using iNOP-7s. iNOP-7s specifically silences apoB in FL83B cells. Cells were treated for 4 hours with iNOP-7s containing unmodified siRNA complexed with respective nanoparticles. ApoB mRNA levels are expressed as percent of control (no transfection). Each value represents the mean+/−SD of duplicate cultures from two representative experiments.
Figure 10:
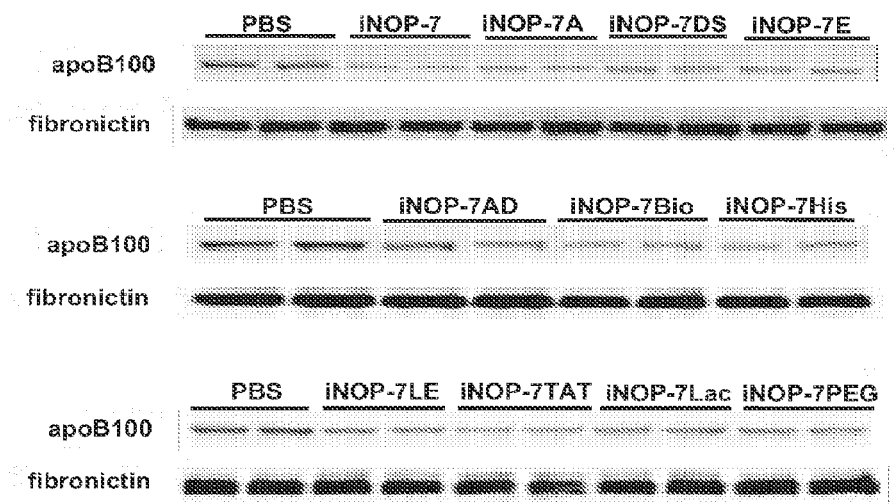
FIG. 10 illustrates the silencing of apoB100 in plasma of mice treated with iNOP-7s. ApoB protein levels were reduced in plasma of mice injected with iNOP-7s. ApoB100 protein expression levels were measured at 48 hours after injection of 1 mg/kg of iNOP07s containing chemically modified siRNA. Total protein loading was confirmed by assessing plasma fibronectin levels.
Figure 11:
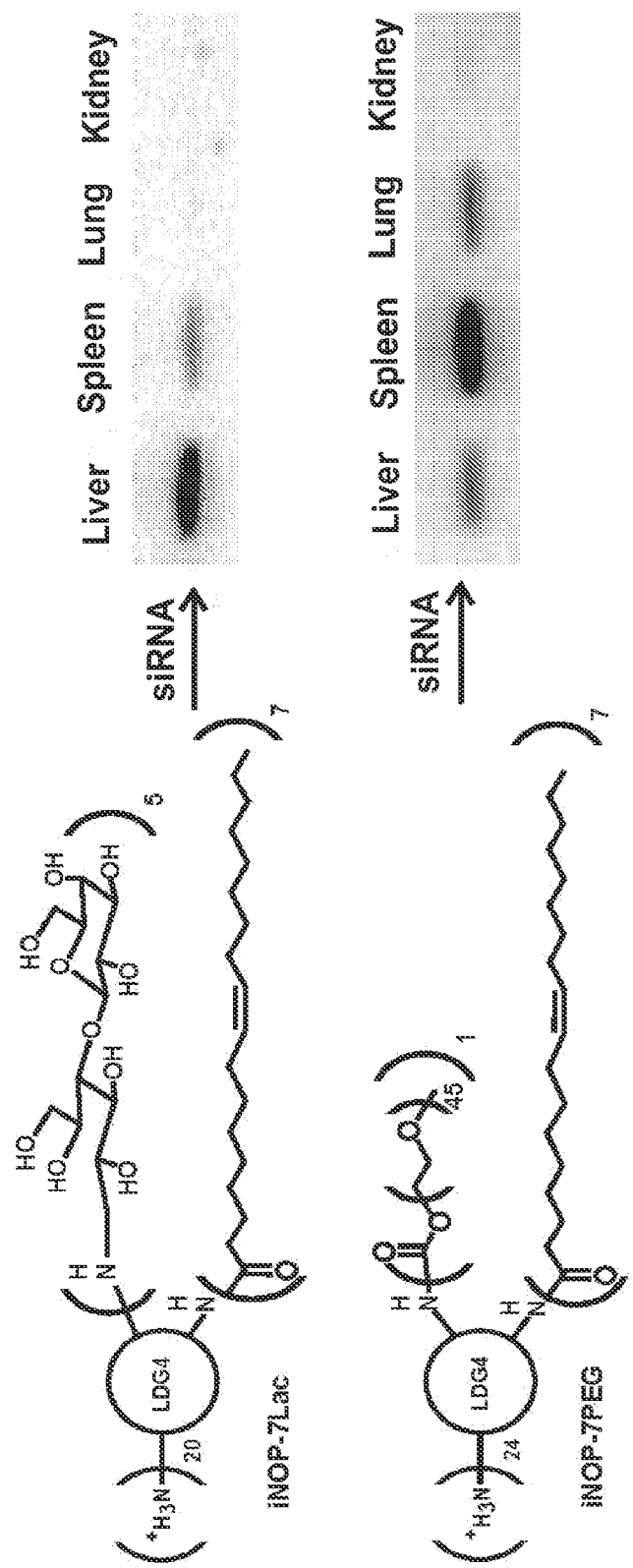
FIG. 11 illustrates interfering nanoparticles (iNOP) made of poly-1-lysine dendrimers having been modified with various functional groups to investigate targeted in vivo RNAi. By analyzing quantitative and systematic RNAi in mice, several novel iNOPs with distinguishing tissue-targeting capabilities were discovered. For example, guide strand of apoB siRNA was found predominantly in liver or spleen by using iNOP-7 Lac or iNOP-7PEG, respectively.

For in vive experiments, iNOP-7Lac was mixed with either chemically modified mismatch siRNA, or perfect match siRNA against mouse apoB. As shown in FIG. 7A, intravenous injection (i.v.) of a dose of 1.0-2.0 mg/kg to C57BL/6 mice caused 50% decreased apoB mRNA level and measured plasma levels of apoB100 protein by immunoblot 48 h after i.v. injection. As shown in FIG. 8, serum levels of apoB100 were found to be decreased to 45%-50% of control levels, whereas levels of an unrelated protein fibronectin were unaffected. These results show that iNOP7-Lac complexed to chemically modified siRNA efficiently silence apoB expression in vivo. Remarkably, these iNOP-7Lac-mediated silencing activities required only ~2.0 mg kg siRNA, a therapeutically feasible dose.

To further evaluate in vivo RNAi by iNOP-7 derivatives in tissues other than liver, Cdk9 was chosen as an alternative target. Unlike apoB which is exclusively expressed in liver and small intestine, Cdk9 is widely expressed throughout the body. Since iNOP-7TAT showed most significant RNAi and tissue distribution in preliminary screening, we used it as a representative iNOP for delivery of Cdk9 siRNA in C57BL/6 mice. A single injection of 1.25 mg kg−1 iNOP-7TAT containing CM Cdk9 siRNA exhibited widespread distribution of siRNA in liver, spleen and lung. Guide strand of Cdk9 siRNA was also detected in heart, adipose tissue and skeletal muscle. Significantly, mRNA level of Cdk9 in liver, spleen and lung decreased by 42%, 46% and 34%, respectively, showing stronger RNAi compared to the prototype iNOP-7 compiexed to CM Cdk9 siRNA (FIG. 7 B).

Size and stability of nanoparticles are crucial for successful in vivo siRNA delivery. Although smaller nanoparticles are preferable over larger ones, an iNOP derivative with a diameter of 48 nm (iNOP-7PEG) was not superior to others in delivery efficiency, possibly because of the PEG chains, which make the particle smaller, also increase its hydrophilicity, thereby decreasing cellular uptake. To facilitate siRNA release from iNOP upon entering cells, degradable iNOP derivatives were tested for siRNA delivery efficiency. iNOP-7E, iNOP-7LE and iNOP-7DS easily released siRNA cargo when incubated with esterase or glutathione (data not shown) in vitro. However, these iNOP derivatives could not increase apoB knockdown in liver, suggesting that stability may not be a crucial element in the case of those derivatives. However, modification of iNOP-7 with a well-known cell penetrating peptide TAT remarkably increased RNAi in multiple organs including lung, which is a hard-to-target organ.

Together, these findings demonstrate that iNOP derivative-mediated siRNA delivery can provide a clinically significant new approach for RNAi therapy. Notably, iNOP derivatives containing chemically modified siRNA did not activate an immune response. Table 3 provides an analysis of liver enzymes, which indicates that the iNOP derivatives were non-toxic. These results demonstrate that further development of iNOP derivative strategy could be applied to create tissue-specific RNAi therapies.

TABLE 3*

|  | ALT (IUL-1) | AST (IUL-1) |
|---|---|---|
| Control | 27 + 9 | 60 + 10 |
| iNOP-7 | 30 + 1 | 66 + 26 |
| iNOP-7A | 30 + 1 | 97 + 4 |
| iNOP-7DS | 18 + 5 | 56 + 18 |
| iNOP-7E | 28 + 1 | 61 + 26 |
| iNOP-7LE | 18 + 6 | 48 + 7 |
| iNOP-7AD | 21 ± 10 | 59 + 20 |
| iNOP-7Bio | 29 + 6 | 102 + 24 |
| iNOP-7His | 13 + 10 | 63 + 11 |
| iNOP-7Lac | 12 + 9 | 68 + 10 |
| iNOP-7PEG | 31 ± 10 | 92 + 18 |
| iNOP-7TAT | 29 + 4 | 76 + 16 |

*Liver enzyme activities in the plasma of mice treated with iN0P-7s. The liver enzyme activities were measured from the plasma of mice treated with intravenous injection of 1 mg kg"1 iNOP-7s containing chemically modified siRNA. The plasma was collected at 48 h after the injection.

Experimental Procedures

I. Synthesis of Functional Groups

A: was synthesized according to the literature procedures.

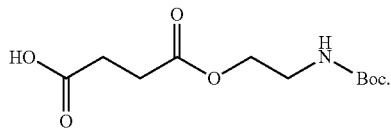

B was prepared as follows:

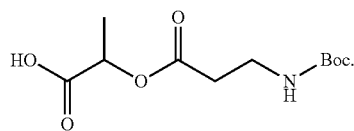

A mixture of Boc-P-Ala (1.07 g, 5.6 mmol), benzyl-S-lactate (1.01 ml) and EDC (1.19 g) in 20 ml dichloromethane was stirred overnight. The solvent was removed and the syrup was suspended in ethyl acetate, followed by washing with 0.5M HCl solution, 5% sodium bicarbonate and water. After filtration the solution was concentrated and the product was purified by silica gel column chromatography to give 1.73 g oil. $^1$H NMR (CDCl3, ppm): δ 1.43 (m, 9H), 1.53 (d, 3H), 2.60 (t, 2H), 3.44 (t, 2H), 4.82 (b, 1H), 10.2-10.5 (b, 1H). MS (ESI) calcd for $C_{11}H_{19}NO_6$ (M+Na+) 284.3, found: 284.1.

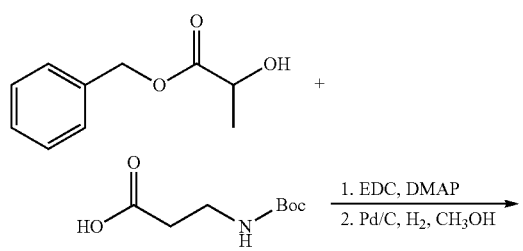

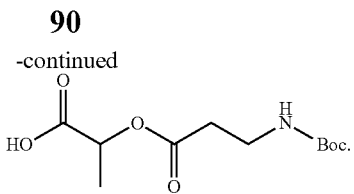

C: was synthesized according to the literature procedures:

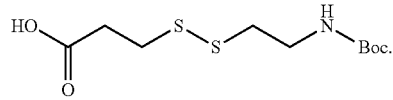

F was prepared as follows:

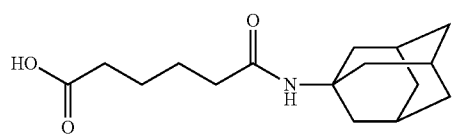

To a solution of 1-adamantanamine (400 mg, 2.6 mmol) and triethylamine (404 µl) in dichloromethane (5 ml) was added dropwise methyl adipoyl chloride (452 µl, 2.8 mmol) in 3 ml dichloromethane. After the suspension was stirred at r.t. for 2 hr, the precipitate was removed by filtration, and the solution was concentrated. The syrup was applied to a silica gel column, and eluted with ethyl acetate and hexane (8:3) to give 0.68 g white powder (yield 89%). The methyl group was removed using a NaOH solution to give 0.49 g white powder. $^1$H NMR (DMSO-d6, ppm): δ 1.42 (m, 4H), 1.57 (t, 6H), 1.88 (m, 6H), 1.96 (t, 5H), 2.16 (t, 2H), 7.21 (s, 1H), 11.97 (b, 1H). MS (ESI) calcd for $C_{16}H_{25}NO_3$ (M+Na+) 302.3, found: 302.1.

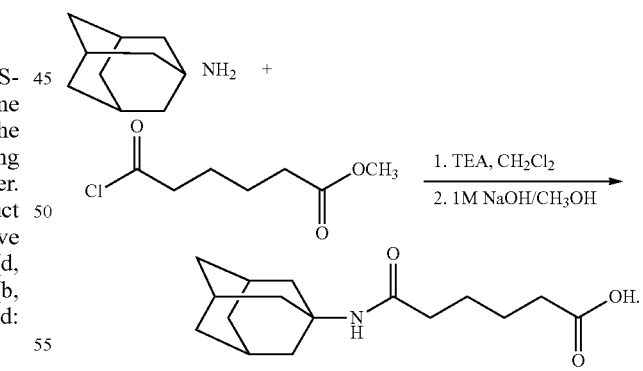

II. Conjugation of Spacers to Lipid Functionalized Polylysine Dendrimer OLD7

Synthesis of 07E: a mixture of OLD7 (20 mg, 3.4 µmol), A (137 mg, µmol) and DIEA (0.49 ml, 2.8 mmol) was suspended in 0.6 ml DMF under nitrogen atmosphere. After the suspension was cooled to 0° C., BOP (221 mg, mmol) was added. The reaction was performed at 0° C. for 30 min and then at room temperature for 24 h. The solvent was removed under reduced pressure, and the obtained syrup was washed repeatedly with ethyl acetate. The product was further purified by re-precipitation from methanol-ethyl acetate system to give a white powder. After TFA deprotection, 34 mg of white powdery OLD7E was obtained.

Synthesis of 07DS: a mixture of OLD7 (16 mg, 2.7 jAmol), C (38 mg, ^mol) and DIEA (25(xl) was suspended in 1.5 ml DMF under nitrogen atmosphere. After the suspension was cooled to 0° C., BOP (61 mg, mmol) was added. The reaction was performed at 0° C. for 30 min and then at room temperature for 24 h. The solvent was removed under reduced pressure, and the obtained syrup was washed repeatedly with ethyl acetate. The product was further purified by re-precipitation from methanol-ethyl acetate system to give a white powder. After TFA deprotection, 20 mg of white powdery 07DS was obtained.

Synthesis of 07LE: a mixture of OLD7 (25 mg, μmol), B (58 mg, μmol) and DIEA (36 μl) was suspended in 3.0 ml DMF under nitrogen atmosphere. After the suspension was cooled to 0° C., BOP (95 mg, mmol) was added. The reaction was performed at 0° C. for 30 min and then at room temperature for 24 h. The solvent was removed under reduced pressure, and the obtained syrup was washed repeatedly with ethyl acetate. The product was further purified by re-precipitation from methanol-ethyl acetate system to give a white powder. After TFA deprotection, 64 mg of white powdery 07LE was obtained.

Synthesis of 07AD: 07 (21 mg, 3.6 μmol), F (3.0 mg) and DIEA (30 μl) was suspended in 0.5 ml DMF under nitrogen atmosphere. After the suspension was cooled to 0° C., BOP (8 mg, mmol) was added. The reaction was performed at 0° C. for 30 min and then at room temperature for 24 h. The solvent was removed under reduced pressure, and the obtained syrup was washed repeatedly with ethyl acetate. The product was further purified by re-precipitation from methanol-ethyl acetate system to give 23 mg white powdery 07AD.

Synthesis of 07His: a mixture of OLD7 (63 mg, 11 μmol), DiBoc-His-OH DCHA (234 mg, 436 μmol) and DIEA (93 μl) was suspended in 3.0 ml DMF under nitrogen atmosphere. After the suspension was cooled to 0° C., BOP (193 mg, mmol) was added. The reaction was performed at 0° C. for 30 min and then at room temperature for 24 h. The solvent was removed under reduced pressure, and the obtained syrup was washed repeatedly with ethyl acetate. The product was further purified by re-precipitation from methanol-ethyl acetate system to give a white powder. After TFA deprotection, 64 mg of white powdery 07His was obtained.

Synthesis of 07Lac: 07 (12 mg), I (p-D-lactose, 2.4 mg) and borane-pyridine complex (1 μl) were suspended in 1 ml 0.05 M borate buffer. The mixture was stirred at 50° C. After 6 days the solution was moved to a tube and dialysized against distilled water for 3 days. A white powder (11.6 mg) was obtained by freeze-drying.

Synthesis of 07A: to a water solution of 07 (76 mg) was added H (acetic anhydride, 24.7 mg) in 1 ml ethyl acetate. The mixture was stirred vigorously for 30 min, followed by removing organic solvent under reduced pressure. The aqueous solution was freeze-dried to give a white powdery 07A (80 mg).

Synthesis of 07Tat: to a solution of 07 (3.7 mg, 0.42 μmol) in PBS pH 7.6 was added sulfo-SMPB (1.0 mg, 2.1 μnmol), followed by stirring at room temperature for 1 hr. The solution was passed through a desalting column equilibrated with PBS, and the obtained solution was mixed with J (TAT peptide, 4.5 mg). The mixture was stirred for 7 hr, passed through desalting column and freeze-dried (8 mg).

Synthesis of 07Bio: to a DMF water solution of 07 (20 mg) was added NHS-biotin (5 mg) in DMF. The mixture was stirred at r.t. for overnight. The product was purified by desalting column and freeze-dried to give 18 mg white powder.

Synthesis of 07PEG: to a solution of 07 (50 mg) and TEA (35 μl) in 2 ml DMF was added dropwise mPEG-4-nitrophenyl chloroformate (16 mg) with vigorous stirring. The reaction proceeded at r.t. for overnight. The solvent was removed and ethyl acetate was added to the syrup. The obtained solid was washed repeatedly with ethyl acetate to give 38 mg white powdery 07PEO.

III. Biological Experiment Methods

Preparation of iNOP-7 derivatives. All siRNAs used in in vivo studies were chemically synthesized using silyl ethers to protect 5'-hydroxyls and acid-labile orthoesters to protect 2'-hydroxyls (2'-ACE) (Dharmacon, Lafayette, Colo.). After deprotection and purification, siRNA strands were annealed as described previously (Chiu and Rana 2003):

ApoB siRNA (ORF position 10049-10071):

UM sense
(SEQ ID NO: 7)
5'-GUCAUCACACUGAAUACCAAU-3',

UM antisense
(SEQ ID NO: 8)
5'-AUUGGUAUUCAGUGUGAUGACAC-3';

CM sense
(SEQ ID NO: 9)
5'-G*U$^F$C$^F$AU$^F$C$^F$ACACUGAAUAC$^F$*CFAA*U$^F$-propylamine-3', CM antisense
(SEQ ID NO: 11)
5'-AU$^F$U$^F$GGUAUUCAGUGUGAU$^F$GAC$^F$*A*C-3';

CM-mm sense
(SEQ ID NO: 11)
5'-G*U$^F$GAU$^F$C$^F$AGACUCAAUAC$^F$GAA*U$^F$-propylarnine-3';

CM-mm antisense
(SEQ ID NO: 15)
5'-AUFU$^F$CGUAUUGAGUCUGAU$^F$CAC$^F$*A*C-3'.

Cdk9 siRNA:
CM sense
(SEQ ID NO: 17)
5'-G*AAC$^F$C$^F$U$^F$AAUUGAGAUU$^F$U$^F$G$^F$U$^F$*U$^F$*U-3'

CM antisense
(SEQ ID NO: 19)
5'-ACAAAU$^F$C$^F$UCAAUUAGGU$^F$U$^F$C$^F$*U$^F$U-3'

The superscript letter F represents 2'-0-F modified nucleotides; asterisk represents phosphorothioate linkage. iNOP-7 derivatives were prepared by mixing siRNA and modified poly-L-lysine dendrimers in 150 mM sucrose or Opti-MEM culture medium (Invitrogen, Carlsbad, Calif.) and incubating at room temperature for 20 min to complex siRNA with nanoparticles.

For in vitro experiment, siGENOME Non-Targeting siRNA (from Dharmacon) was used as negative control. DDBI siRNA sequence is as following:

Sense 5'-G UUU UUG GCA AUC AAC AGO dTdT-3' (SEQ ID NO: 21)

Antisense 5'-CCU GUU GAU UGC CAA AAA CdTdT-3' (SEQ ID NO: 22); A siGENOME SMART POOL targeting mouse Trp53 was used.

In Vitro RNAi Activity of iNOP-7 derivatives. FL83B (mouse hepatocytes) cells were maintained at 37° C. with 5% CO2 in F-12K culture medium (ATCC, Manassas, Va.) supplemented with 10% fetal bovine serum, 100 U mL"1 penicillin and 100 ^g mL"1 streptomycin. Cells were regularly passaged and plated in 6-well culture plates for 16 h before transfection at 70% confluency. Cells were transfected with 1 mL per well of complex (siRNA-nanoparticles) for 4 h at 37° C. Efficiency of RNAi was determined as described previously (Soutschek, Akine et al. 2004) (Chiu, Ali et al. 2004). In Vivo Silencing. All animal procedures were approved by the Institutional Animal Care and Use Committee (University of Massachusetts Medical School). Six- to eight-week-old male C57BL/6 mice (Charles River Laboratories, Wilmington, Mass.) were maintained under a 12 h dark cycle in a pathogen-free animal facility. Mice were administrated with either phosphate buffered saline pH 7.4 (PBS) or iNOP-7 derivatives containing mismatch siRNA or perfect match siRNA at 1 mg kg"1 as bolus intravenous injection via the lateral tail vein. Forty-eight hours after the injection, liver, spleen, kidney, lung and plasma were collected and stored in −80° C. until analysis.

Quantitative PCR. To determine mRNA levels in cell culture or mouse tissues after siRNA treatment, total RNA was extracted with TRIZOL (Invitrogen, Carlsbad, Calif.) and treated with TORBO DNA-free kit (Applied Biosystems, Foster City, Calif.) before quantification. In preparation for quantitative PCR, total RNA (400 ng) was reverse transcribed by using Superscript II (Invitrogen, Carlsbad, Calif.) and random primers according to the manufacturer's protocol. The expression of mRNA was measured using ABsolute QPCR SYBR green mix (ThermoFisher Scientific, Epsom, Surrey, UK) normalized to GAPDH according to the manufacturer's instructions. Quantitative PCR was performed by using a Chromo4 Real-Time PCR Detection System (BioRad, Hercules, Calif.).

Western Blotting. Separation of serum proteins was accomplished by electrophoresis on 6% polyacrylamide/SDS gels. The separated proteins were electrophoretically transferred to PVDF membrane followed by incubation with a 1:1,000 dilution of goat polyclonal anti-ApoB antibody (Santa Cruz Biotechnology, Santa Cruz, Calif.). The blot was then incubated with a 1:2,000 dilution of donkey anti-goat antibody conjugated to horseradish peroxidase (Santa Cruz Biotechnology, Santa Cruz, Calif.), and antibody binding was detected by using an enhanced chemiluminescent detection kit (PerkinElmer, Waltham, Mass.). As a control, fibronectin was visualized by immunoblot using a polyclonal rabbit anti-fibronectin antibody (Sigma-Aldrich, St. Louis, Mo.).

Measurement of Lipid Profile in Plasma. Serum levels of ALT, AST, cholesterol, lipoproteins, triglycerides and glucose were measured by using automated systems at the Kronos Science Laboratories (Phoenix, Ariz.).

Northern Blotting. RNA from mouse tissues was homogenized in TRIZOL (Invitrogen, Carlsbad, Calif.) and isolated according to the manufacturer's instructions. Total RNA was separated on a 14% acrylamide/20% formamide/8 M urea gel, then electroblotted onto Hybond-XL nylon membrane (GE Healthcare, Piscataway, N.J.). The probe with y-32P-labelled oligonucleotides for antisense of siRNA was hybridized to the membrane at 42° C. The blots were visualized by scanning in a FLA-5000 scanner (Fujifilm, Stamford, Conn.).

In Vivo Interferon Induction. To assess for any nonspecific immune response to injected siRNA complexed with nanoparticles, mouse liver RNA was analyzed for expression of the IFN-inducible genes by quantitative RT-PCR. Serum levels of mouse IFN-a were measured by using a sandwich ELISA kit according to the manufacturer's instructions (PBL Biomedical, Piscataway, N.J.) (Marques and Williams 2005).

All references cited herein are hereby incorporated by reference in their entireties, whether previously specifically incorporated or not.

Although the invention has been described with reference to the above example, and to Attachment 1, the entire content of which is incorporated by reference in its entirety, it will be understood that modifications and variations are encompassed within the spirit and scope of the invention. Accordingly, the invention is limited only by the following claims.

What is claimed is:

1. A composition comprising a nanotransporter interfering nanoparticle-7 (iNOP-7) having a polylysine dendrimer generation 4 (LDG4) core conjugated to a lipid functional group having the following structure:

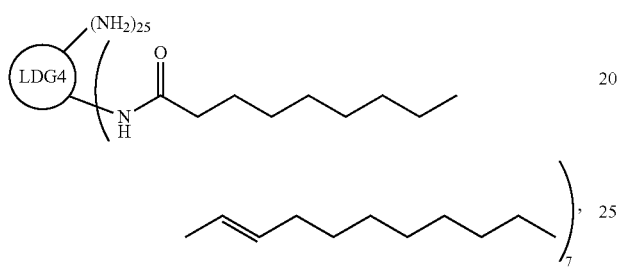

wherein the iNOP-7 is functionalized with any of functional surface groups A-I by being conjugated to iNOP-7 through an amide bond formed via an $NH_2$ group of the iNOP7:

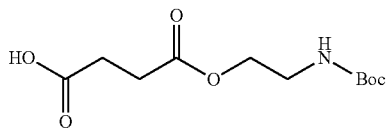 A

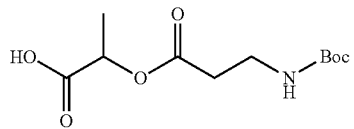 B

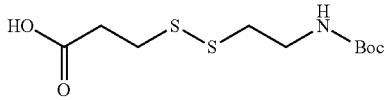 C

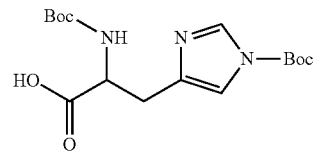 D

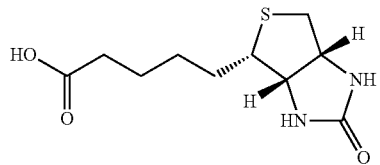 E

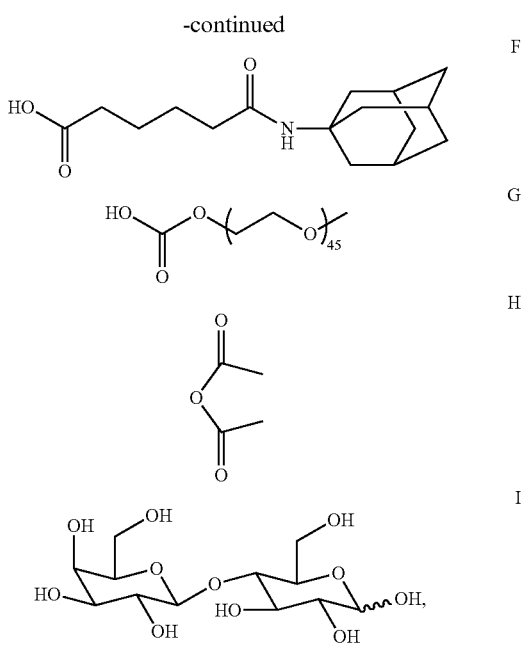

wherein A forms iNOP-7E; B forms iNOP-7LE; C forms iNOP-7DS; D forms iNOP-7His; E-forms iNOP-7Bio; F forms iNOP-7AD; G forms iNOP-7PEG; H forms iNOP-7A; and I forms iNOP-7Lac, wherein the iNOP-7 is associated with a sense strand oligonucleotide molecule.

2. The composition of claim 1, wherein the oligonucleotide comprises DNA.

3. The composition of claim 1, wherein the oligonucleotide comprises RNA.

4. The composition of claim 3, wherein the RNA is selected from the group consisting of microRNA mimic, anti-microRNA, dsRNA, siRNA, or shRNA.

5. The composition of claim 3, wherein the RNA is chemically modified.

6. The composition of claim 5, wherein the chemical modification comprises a 2'-O—F, 2'-Ome, 2'MOE, 2'-H, 2'-amino, 4-thioU or 6-thioG modification of one or more nucleotides, introduction of one or more phosphorothioate linkages, introduction of one or more locked nucleotides, or a combination thereof.

7. The composition of claim 1, wherein the oligonucleotide is about 5-60 nucleotides in length.

8. The composition of claim 7, wherein the oligonucleotide is about 7-36 nucleotides in length.

9. A method of delivering an oligonucleotide to a cell comprising contacting the cell with a nanotransporter interfering nanoparticle-7 (iNOP-7) associated with a sense oligonucleotide, the iNOP-7 having a polylysine dendrimer generation 4 (LDG4) core conjugated to a lipid functional group having the following structure:

wherein the iNOP-7 is functionalized with any of functional surface groups A-I by being conjugated to iNOP-7 through an amide bond formed via an NH₂ group of the iNOP7:

A

B

C

D

E

F

G

H

I wherein A forms iNOP-7E; B forms iNOP-7LE; C forms iNOP-7DS; D forms iNOP-7His; E-forms iNOP-7Bio; F forms iNOP-7AD; G forms iNOP-7PEG; H forms iNOP-7A; and I forms iNOP-7Lac.

10. The method of claim 9, wherein the oligonucleotide comprises DNA.

11. The method of claim 9, wherein the oligonucleotide comprises RNA.

12. The method of claim 11, wherein the RNA is selected from the group consisting of microRNA mimic, anti-microRNA, dsRNA, siRNA, or shRNA.

13. The method of claim 11, wherein the RNA is chemically modified.

14. The method of claim 13, wherein the chemical modification comprises a 2'-O—F, 2'-Ome, 2'MOE, 2'-H, 2'-amino, 4-thioU or 6-thioG modification of one or more nucleotides, introduction of one or more phosphorothioate linkages, introduction of one or more locked nucleotides, or a combination thereof.

15. The method of claim 9, wherein the oligonucleotide is about 5-60 nucleotides in length.

16. The method of claim 15, wherein the oligonucleotide is about 7-36 nucleotides in length.

17. The method of claim 9, wherein the method is performed in vivo.

18. The method of claim 9, wherein the method is performed in vitro.

19. The method of claim 9, wherein the cell is mammalian.

20. The method of claim 19, wherein the mammal is a human, mouse, rat, dog, monkey or ape.

21. The method of claim 9, wherein the cell is an embryonic stem cell or induced pluripotent stem cell.

* * * * *

UNITED STATES PATENT AND TRADEMARK OFFICE
CERTIFICATE OF CORRECTION

PATENT NO. : 9,878,050 B2
APPLICATION NO. : 15/374679
DATED : January 30, 2018
INVENTOR(S) : Tariq M. Rana Page 1 of 1

It is certified that error appears in the above-identified patent and that said Letters Patent is hereby corrected as shown below:

In the Specification

In Column 1, Lines 18 through 21, please replace:
"This invention was made with government support under Grant Nos. NS060856 and AI41404 awarded by the National Institutes of Health. The government has certain rights in this invention."

With:
"This invention was made with government support under NS060856 and AI041404 awarded by the National Institutes of Health. The government has certain rights in the invention."

Signed and Sealed this
Sixth Day of April, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 22

<210> SEQ ID NO 1
<211> LENGTH: 23
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: 2'-O-F modified nucleotide
<220> FEATURE:
<221> NAME/KEY: misc_feature
<222> LOCATION: (6)..(6)
<223> OTHER INFORMATION: 2'-O-F modified nucleotide
<220> FEATURE:
<221> NAME/KEY: misc_feature
<222> LOCATION: (8)..(9)
<223> OTHER INFORMATION: 2'-O-F modified nucleotide

<400> SEQUENCE: 1
acaaacacca uugucacacu cca                                            23
```

-continued

```
<210> SEQ ID NO 2
<211> LENGTH: 24
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)..(4)
<223> OTHER INFORMATION: 2'-O-F modified nucleotide
<220> FEATURE:
<221> NAME/KEY: misc_feature
<222> LOCATION: (7)..(7)
<223> OTHER INFORMATION: 2'-O-F modified nucleotide
<220> FEATURE:
<221> NAME/KEY: misc_feature
<222> LOCATION: (11)..(11)
<223> OTHER INFORMATION: 2'-O-F modified nucleotide

<400> SEQUENCE: 2
ucacaaccuc cuagaaagag uaga                                              24

<210> SEQ ID NO 3
<211> LENGTH: 23
<212> TYPE: RNA
<213> ORGANISM: Artificial Sequence
<220> FEATURE:
<223> OTHER INFORMATION: Synthetic construct

<400> SEQUENCE: 3
acaaacacca uugucacacu cca                                               23

<210> SEQ ID NO 4
<211> LENGTH: 24
<212> TYPE: RNA
<213> ORGANISM: Artificial Sequence
<220> FEATURE:
<223> OTHER INFORMATION: Synthetic construct

<400> SEQUENCE: 4
ucacaaccuc cuagaaagag uaga                                              24

<210> SEQ ID NO 5
<211> LENGTH: 12
<212> TYPE: PRT
<213> ORGANISM: Artificial Sequence
<220> FEATURE:
<223> OTHER INFORMATION: Synthetic construct

<400> SEQUENCE: 5

Cys Tyr Gly Arg Lys Lys Arg Arg Gln Arg Arg Arg
1               5                   10

<210> SEQ ID NO 6
<211> LENGTH: 5
<212> TYPE: PRT
<213> ORGANISM: Artificial Sequence
<220> FEATURE:
<223> OTHER INFORMATION: Synthetic construct

<400> SEQUENCE: 6

Cys Asn Gly Arg Cys
1               5

<210> SEQ ID NO 7
<211> LENGTH: 21
<212> TYPE: RNA
<213> ORGANISM: Artificial Sequence
<220> FEATURE:
```

```
<223> OTHER INFORMATION: Synthetic construct

<400> SEQUENCE: 7
gucaucacac ugaauaccaa u                                              21

<210> SEQ ID NO 8
<211> LENGTH: 23
<212> TYPE: RNA
<213> ORGANISM: Artificial Sequence
<220> FEATURE:
<223> OTHER INFORMATION: Synthetic construct

<400> SEQUENCE: 8
auugguauuc agugugauga cac                                            23

<210> SEQ ID NO 9
<211> LENGTH: 21
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(3)
<223> OTHER INFORMATION: 2'-O-F modified nucleotide
<220> FEATURE:
<221> NAME/KEY: misc_feature
<222> LOCATION: (5)..(6)
<223> OTHER INFORMATION: 2'-O-F modified nucleotide
<220> FEATURE:
<221> NAME/KEY: misc_feature
<222> LOCATION: (17)..(18)
<223> OTHER INFORMATION: phosphorothioate linkage
<220> FEATURE:
<221> NAME/KEY: misc_feature
<222> LOCATION: (17)..(18)
<223> OTHER INFORMATION: 2'-O-F modified nucleotide
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: 2'-O-F modified nucleotide

<400> SEQUENCE: 9
gucaucacac ugaauaccaa u                                              21

<210> SEQ ID NO 10
<211> LENGTH: 21
<212> TYPE: RNA
<213> ORGANISM: Artificial Sequence
<220> FEATURE:
<223> OTHER INFORMATION: Synthetic construct

<400> SEQUENCE: 10
gucaucacac ugaauaccaa u                                              21

<210> SEQ ID NO 11
<211> LENGTH: 23
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
```

```
<222> LOCATION: (2)..(3)
<223> OTHER INFORMATION: 2'-O-F modified nucleotide
<220> FEATURE:
<221> NAME/KEY: misc_feature
<222> LOCATION: (18)..(18)
<223> OTHER INFORMATION: 2'-O-F modified nucleotide
<220> FEATURE:
<221> NAME/KEY: misc_feature
<222> LOCATION: (21)..(21)
<223> OTHER INFORMATION: 2'-O-F modified nucleotide
<220> FEATURE:
<221> NAME/KEY: misc_feature
<222> LOCATION: (21)..(22)
<223> OTHER INFORMATION: phosphorothioate linkage
<220> FEATURE:
<221> NAME/KEY: misc_feature
<222> LOCATION: (22)..(23)
<223> OTHER INFORMATION: phosphorothioate linkage

<400> SEQUENCE: 11
auugguauuc agugugauga cac                                           23

<210> SEQ ID NO 12
<211> LENGTH: 23
<212> TYPE: RNA
<213> ORGANISM: Artificial Sequence
<220> FEATURE:
<223> OTHER INFORMATION: Synthetic construct

<400> SEQUENCE: 12
auugguauuc agugugauga cac                                           23

<210> SEQ ID NO 13
<211> LENGTH: 21
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (2)..(2)
<223> OTHER INFORMATION: 2'-O-F modified nucleotide
<220> FEATURE:
<221> NAME/KEY: misc_feature
<222> LOCATION: (5)..(6)
<223> OTHER INFORMATION: 2'-O-F modified nucleotide
<220> FEATURE:
<221> NAME/KEY: misc_feature
<222> LOCATION: (17)..(17)
<223> OTHER INFORMATION: 2'-O-F modified nucleotide
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: 2'-O-F modified nucleotide

<400> SEQUENCE: 13
gugaucagac ucaauacgaa u                                             21

<210> SEQ ID NO 14
<211> LENGTH: 21
<212> TYPE: RNA
<213> ORGANISM: Artificial Sequence
<220> FEATURE:
<223> OTHER INFORMATION: Synthetic construct
```

-continued

```
<400> SEQUENCE: 14
gugaucagac ucaauacgaa u                                              21

<210> SEQ ID NO 15
<211> LENGTH: 23
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(3)
<223> OTHER INFORMATION: 2'-O-F modified nucleotide
<220> FEATURE:
<221> NAME/KEY: misc_feature
<222> LOCATION: (18)..(18)
<223> OTHER INFORMATION: 2'-O-F modified nucleotide
<220> FEATURE:
<221> NAME/KEY: misc_feature
<222> LOCATION: (21)..(21)
<223> OTHER INFORMATION: 2'-O-F modified nucleotide
<220> FEATURE:
<221> NAME/KEY: misc_feature
<222> LOCATION: (21)..(22)
<223> OTHER INFORMATION: phosphorothioate linkage
<220> FEATURE:
<221> NAME/KEY: misc_feature
<222> LOCATION: (22)..(23)
<223> OTHER INFORMATION: phosphorothioate linkage

<400> SEQUENCE: 15
auucguauug agucugauca cac                                            23

<210> SEQ ID NO 16
<211> LENGTH: 23
<212> TYPE: RNA
<213> ORGANISM: Artificial Sequence
<220> FEATURE:
<223> OTHER INFORMATION: Synthetic construct

<400> SEQUENCE: 16
auucguauug agucugauca cac                                            23

<210> SEQ ID NO 17
<211> LENGTH: 21
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (4)..(6)
<223> OTHER INFORMATION: 2'-O-F modified nucleotide
<220> FEATURE:
<221> NAME/KEY: misc_feature
<222> LOCATION: (16)..(20)
<223> OTHER INFORMATION: 2'-O-F modified nucleotide
<220> FEATURE:
<221> NAME/KEY: misc_feature
<222> LOCATION: (19)..(20)
<223> OTHER INFORMATION: phosphorothioate linkage
<220> FEATURE:
<221> NAME/KEY: misc_feature
<222> LOCATION: (20)..(21)
<223> OTHER INFORMATION: phosphorothioate linkage

<400> SEQUENCE: 17
gaaccuaauu gagauuuguu u                                              21
```

```
<210> SEQ ID NO 18
<211> LENGTH: 21
<212> TYPE: RNA
<213> ORGANISM: Artificial Sequence
<220> FEATURE:
<223> OTHER INFORMATION: Synthetic construct

<400> SEQUENCE: 18
gaaccuaauu gagauuuguu u                                             21

<210> SEQ ID NO 19
<211> LENGTH: 21
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (6)..(7)
<223> OTHER INFORMATION: 2'-O-F modified nucleotide
<220> FEATURE:
<221> NAME/KEY: misc_feature
<222> LOCATION: (17)..(20)
<223> OTHER INFORMATION: 2'-O-F modified nucleotide
<220> FEATURE:
<221> NAME/KEY: misc_feature
<222> LOCATION: (19)..(20)
<223> OTHER INFORMATION: phosphorothioate linkage

<400> SEQUENCE: 19
acaaaucuca auuagguucu u                                             21

<210> SEQ ID NO 20
<211> LENGTH: 21
<212> TYPE: RNA
<213> ORGANISM: Artificial Sequence
<220> FEATURE:
<223> OTHER INFORMATION: Synthetic construct

<400> SEQUENCE: 20
acaaaucuca auuagguucu u                                             21

<210> SEQ ID NO 21
<211> LENGTH: 21
<212> TYPE: DNA
<213> ORGANISM: Artificial Sequence
<220> FEATURE:
<223> OTHER INFORMATION: Synthetic construct: DNA/RNA sequence
<220> FEATURE:
<221> NAME/KEY: misc_feature
<222> LOCATION: (20)..(21)
<223> OTHER INFORMATION: n is deoxythymidine

<400> SEQUENCE: 21
guuuuuggca aucaacaggn n                                             21

<210> SEQ ID NO 22
<211> LENGTH: 21
<212> TYPE: DNA
<213> ORGANISM: Artificial Sequence
<220> FEATURE:
<223> OTHER INFORMATION: Synthetic construct: DNA/RNA sequence
<220> FEATURE:
<221> NAME/KEY: misc_feature
```

```
<222> LOCATION: (20)..(21)
<223> OTHER INFORMATION: n is deoxythymidine

<400> SEQUENCE: 22
ccuguugauu gccaaaaacn n                                              21
```